United States Patent
Collins et al.

(10) Patent No.: US 11,639,326 B2
(45) Date of Patent: May 2, 2023

(54) CONTINUOUS FLOW SYNTHESIS OF IBUPROFEN

(71) Applicant: SRI INTERNATIONAL, Menlo Park, CA (US)

(72) Inventors: Nathan Collins, San Mateo, CA (US); Jeremiah Malerich, San Jose, CA (US); Judy Szeto, Daly City, CA (US); Joseph A. Kozocas, Fremont, CA (US)

(73) Assignee: SRI International, Menlo Park, CA (US)

( * ) Notice: Subject to any disclaimer, the term of this patent is extended or adjusted under 35 U.S.C. 154(b) by 598 days.

(21) Appl. No.: 16/500,687

(22) PCT Filed: Apr. 6, 2018

(86) PCT No.: PCT/US2018/026506
§ 371 (c)(1),
(2) Date: Oct. 3, 2019

(87) PCT Pub. No.: WO2018/187717
PCT Pub. Date: Oct. 11, 2018

(65) Prior Publication Data
US 2021/0114962 A1 Apr. 22, 2021

Related U.S. Application Data

(60) Provisional application No. 62/482,550, filed on Apr. 6, 2017.

(51) Int. Cl.
C07C 51/08 (2006.01)
C07C 253/16 (2006.01)
(Continued)

(52) U.S. Cl.
CPC .............. C07C 51/08 (2013.01); C07C 17/16 (2013.01); C07C 29/143 (2013.01); C07C 45/46 (2013.01);
(Continued)

(58) Field of Classification Search
None
See application file for complete search history.

(56) References Cited

U.S. PATENT DOCUMENTS 5,266,723 A 11/1993 Hanna et al.
5,380,927 A * 1/1995 Paradies ................ A61K 9/146
562/864

(Continued)

FOREIGN PATENT DOCUMENTS

EP 3606660 2/2020
JP 2020-520298 7/2020
(Continued)

OTHER PUBLICATIONS

U.S. Appl. No. 62/482,550, filed Apr. 6, 2017, Nathan Collins.
(Continued)

Primary Examiner — Amy C Bonaparte
(74) Attorney, Agent, or Firm — Dicke, Billig & Czaja, PLLC

(57) ABSTRACT

This disclosure generally relates to methods of making ibuprofen, naproxen, and derivatives thereof. This disclosure also generally relates to compounds made by the disclosed methods. This abstract is intended as a scanning tool for purposes of searching in the particular art and is not intended to be limiting of the present invention.

16 Claims, 45 Drawing Sheets

(51) Int. Cl.
*C07C 253/14* (2006.01)
*C07C 17/16* (2006.01)
*C07C 29/143* (2006.01)
*C07C 303/28* (2006.01)
*C07C 45/46* (2006.01)
*C07C 57/30* (2006.01)
*C07C 255/01* (2006.01)

(52) U.S. Cl.
CPC .......... *C07C 253/14* (2013.01); *C07C 253/16* (2013.01); *C07C 303/28* (2013.01); *C07C 57/30* (2013.01); *C07C 255/01* (2013.01)

(56) References Cited

U.S. PATENT DOCUMENTS

| 2005/0014132 | A1 | 1/2005 | Kaddurah-Daouk et al. |
| 2012/0022705 | A1 | 1/2012 | Ludwig |
| 2012/0094366 | A1 | 4/2012 | Ludwig |
| 2012/0164743 | A1 | 6/2012 | Aota et al. |
| 2014/0010734 | A1 | 1/2014 | Ludwig |

FOREIGN PATENT DOCUMENTS

| WO | WO 2017/029494 A1 | 2/2017 |
| WO | WO 2018/187717 | 10/2018 |
| WO | WO 2018/187745 | 10/2018 |

OTHER PUBLICATIONS

U.S. Appl. No. 62/482,515, filed Apr. 6, 2017, Jin-Ping Lim.
U.S. Appl. No. 16/496,834, filed Apr. 6, 2018, Jin-Ping Lim.
PCT, PCT/US2018/026506 (WO 2018/187717), Apr. 6, 2018, Nathan Collins (SRI International).
AU, 2018250317, Apr. 6, 2018, Jin-Ping Lim (SRI International).
CN, 2018800316477 (CN 110650797A), Apr. 6, 2018, Jin-Ping Lim (SRI International).
EP, 18781821.6 (EP 3606660), Apr. 6, 2018, Jin-Ping Lim (SRI International).
JP, 2019-554832 (JP 2020-520298), Apr. 6, 2018, Jin-Ping Lim (SRI International).
PCT, PCT/US2018/026557 (WO 2018/187745), Apr. 6, 2018, Jin-Ping Lim (SRI International).
Wang (2014) "Synthesis and Crystal Structure of [a-(2,4-Difluorophenyl)-a-(1H-1,2,4-triazole-1-ylmethyl)-1H-1,2,4-triazole-1-ethanol]Cu(II) Complex" *Asian J. Chem.* 26(24): 8593-8595.
International Search Report and Written Opinion dated Oct. 11, 2018 by the International Searching Authority for International Application No. PCT/US2018/026506, filed on Apr. 6, 2018, and published as WO 2018/187717 dated Oct. 11, 2018 (Applicant—SRI International) (21 Pages).
International Preliminary Report on Patentability dated May 21, 2018 the International Searching Authority for International Application No. PCT/US2018/026506, filed on Apr. 6, 2018, and published as WO 2018/187717 dated Oct. 11, 2018 (Applicant—SRI International) (8 Pages).
International Search Report and Written Opinion dated Jun. 21, 2018 by the International Searching Authority for International Application No. PCT/US2018/026557, filed on Apr. 6, 2018, and published as WO 2018187745 dated Oct. 10, 2018 (Applicant—SRI International) (18 Pages).
International Preliminary Report on Patentability dated May 30, 2018 by the International Searching Authority for International Application No. PCT/US2018/026557, filed on Apr. 6, 2018, and published as WO 2018187745 dated Oct. 10, 2018 (Applicant—SRI International) (11 Pages).

\* cited by examiner

- 95% CONVERSION BY HPLC
- 80% CONVERSION BY NMR
- 55% YIELD AFTER SiO2 (~3.8 g + 1 g AVAILABLE)

- EtOH, iPrOH, MeCN-CARBOXYLIC ACID:AMIDE (1:1)
- DMSO-CARBOXYLIC ACID

- CHCl₃-CARBOXYLIC ACID:AMIDE (85:15)
- TOLUENE-CARBOXYLIC ACID:AMIDE (80:20)

| Solvent | Count | | Solvent | Count |
|---|---|---|---|---|
| MeCN | 318 | | ClCH2CH2Cl | 6 |
| CH2Cl2 | 295 | | AcOR | 5 |
| THF | 183 | | Me(CH2)4Me | 5 |
| H2O | 153 | | O=S(CD3)2 | 5 |
| DMSO | 105 | | Me2CHOH | 4 |
| REACTIONS NOT CONTAINING INFORMATION FOR THIS ANALYSIS | 98 | | CCl4 | 3 |
| DMF | 98 | | PrOR | 3 |
| MeOH | 97 | | AcOMe | 2 |
| PhMe | 60 | | CD3C6D5 | 2 |
| CHCl3 | 50 | | Et3H | 2 |
| 359845-21-8 | 39 | | Me(CH2)8Me | 2 |
| EtOH | 33 | | t-BuOMe | 2 |
| BENZENE | 22 | | (Me2H)3P=O | 1 |
| Me2CO | 17 | | (MeOCH2CH2)2O | 1 |
| CD2Cl2 | 16 | | AcNMe2 | 1 |
| Et2O | 16 | | C5D5H | 1 |
| AcOEt | 15 | | C6D6 | 1 |
| CDCl3 | 14 | | D2O | 1 |
| DIOXANE | 13 | | F3CCH2OH | 1 |
| NMP | 8 | | H2 | 1 |
| C5H5N | 7 | | o-DICHLOROBENZENE | 1 |
| CD3CN | 6 | | PhF | 1 |

FIG. 28

CONTINUOUS FLOW SYNTHESIS OF IBUPROFEN

CROSS-REFERENCE TO RELATED APPLICATIONS

This Application is a national stage filing under 35 U.S.C. § 371 of International Application No. PCT/US2018/026506, filed on Apr. 6, 2018, which claims the benefit of U.S. Provisional Application No. 62/482,550, filed on Apr. 6, 2017, the contents of which are incorporated herein by reference in their entireties.

STATEMENT REGARDING FEDERALLY SPONSORED RESEARCH

This invention was made with government support under Contract No. W911NF-16-C-0051 awarded by the United States Army. The government has certain rights in the invention.

BACKGROUND

Ibuprofen is an analgesic and non-steroidal anti-inflammatory drug (NSAID) that is the active pharmaceutical ingredient (API) in Advil, Motrin, and other similar pain relievers. The conventional synthesis of ibuprofen, also known as the Boots process, involves six steps and the waste materials produced required downstream treatments for disposal. An alternative synthesis was later proposed that simplified the process to only three steps (i.e., the BASF process). However, the final step requires an expensive, heavy catalyst. Likewise, naproxen is an analgesic NSAID that is the active pharmaceutical ingredient (API) in Aleve, Naprosyn, and other similar pain relievers. The conventional Syntex synthesis involves five steps, including a chiral resolution (i.e., a separation based on chirality).

Despite the widespread use of ibuprofen and naproxen, a streamlined synthesis that relies on inexpensive reagents has thus far remained elusive. Further, efficient stereospecific routes have remained elusive. Therefore, there remains a need for the development of concise synthetic routes to ibuprofen and naproxen that minimize waste, are stereospecific, and/or are high yielding. These needs and others are met by the present invention.

SUMMARY OF THE INVENTION

In accordance with the purpose(s) of the invention, as embodied and broadly described herein, the invention, in one aspect, relates to methods of making ibuprofen, naproxen, and derivatives thereof, and compounds produced by a disclosed method.

Disclosed are methods for preparing a cyano compound having a structure represented by a formula:

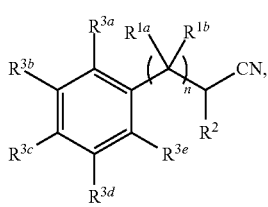

wherein n is selected from 0, 1, 2, 3, and 4; wherein each of $R^{1a}$ and $R^{1b}$, when present, is independently selected from hydrogen and C1-C4 alkyl; wherein $R^2$ is selected from hydrogen and C1-C4 alkyl; and wherein each of $R^{3a}$, $R^{3b}$, $R^{3c}$, $R^{3d}$, and $R^{3e}$ is independently selected from hydrogen, halogen, —OH, —NH$_2$, —NO$_2$, —CN, C1-C4 alkyl, and C1-C4 alkoxy; or wherein any two of $R^{3a}$, $R^{3b}$, $R^{3c}$, $R^{3d}$, and $R^{3e}$ together comprise a structure represented by a formula:

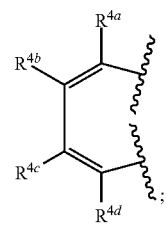

and
wherein each of $R^{4a}$, $R^{4b}$, $R^{4c}$, and $R^{4d}$, when present, is independently selected from hydrogen, halogen, —OH, —NH$_2$, —NO$_2$, —CN, C1-C4 alkyl, and C1-C4 alkoxy, the method comprising the steps of: (a) reducing a carboxyl compound having a structure represented by a formula:

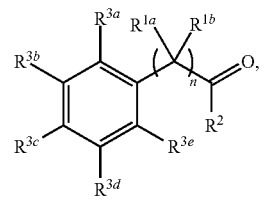

thereby producing an alcohol having a structure represented by a formula:

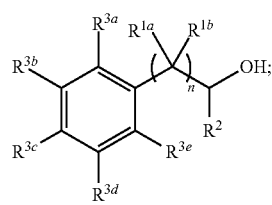

(b) converting a hydroxyl group on the alcohol to a leaving group, thereby producing a compound having a structure represented by a formula:

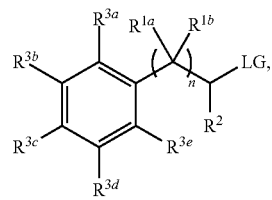

wherein LG is a leaving group; and (c) displacing the leaving group with a nucleophilic cyanide reagent, thereby producing the cyano compound.

Also disclosed are methods for preparing a cyano compound having a structure:

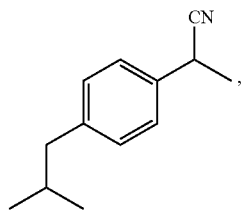

the method comprising the steps of: (a) reducing a carboxyl compound having a structure:

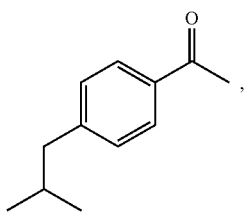

thereby producing an alcohol having a structure:

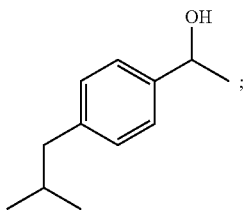

converting a hydroxyl group on the alcohol to a leaving group, thereby producing a compound having a structure:

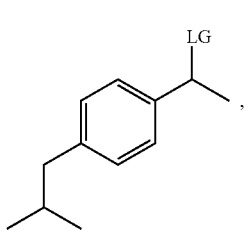

wherein LG is selected from chloro and mesyl; and (c) displacing the leaving group with a nucleophilic cyanide reagent, thereby producing the cyano compound.

Also disclosed are methods for preparing a carboxylic acid having a structure represented by a formula:

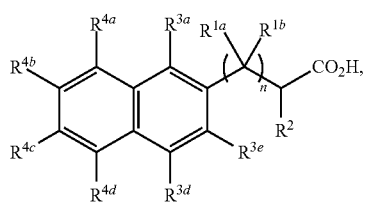

wherein n is selected from 0, 1, 2, 3, and 4; wherein each of $R^{1a}$ and $R^{1b}$, when present, is independently selected from hydrogen and C1-C4 alkyl; wherein $R^2$ is selected from hydrogen and C1-C4 alkyl; and wherein each of $R^{3a}$, $R^{3d}$, and $R^{3e}$ is independently selected from hydrogen, halogen, —OH, —NH$_2$, —NO$_2$, —CN, C1-C4 alkyl, and C1-C4 alkoxy; and wherein each of $R^{4a}$, $R^{4b}$, $R^{4c}$, and $R^{4d}$ is independently selected from hydrogen, halogen, —OH, —NH$_2$, —NO$_2$, —CN, C1-C4 alkyl, and C1-C4 alkoxy, the method comprising the steps of: (a) converting a hydroxyl group on an alcohol to a leaving group, wherein the alcohol has a structure represented by a formula:

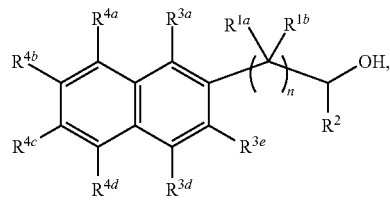

thereby producing a compound having a structure represented by a formula:

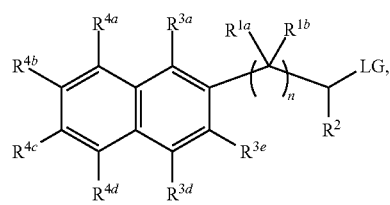

wherein LG is a leaving group; (b) displacing the leaving group with a nucleophilic cyanide reagent, thereby producing a cyano compound having a structure represented by a formula:

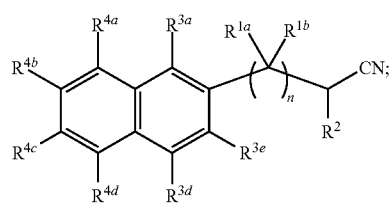

and
(c) hydrolyzing the cyano compound, thereby producing the carboxylic acid.

Also disclosed are compounds prepared by a disclosed method.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The foregoing and other objects and aspects of the present invention are explained in greater detail in the drawings herein and the specification set forth below. The disclosures of all United States patent references cited herein are to be incorporated herein by reference.

BRIEF DESCRIPTION OF THE DRAWINGS

The accompanying figures, which are incorporated in and constitute a part of this specification, illustrate several aspects and together with the description serve to explain the principles of the invention.

FIG. 16A shows Trial 1 and FIG. 16B shows Trial 2 of the two step flow synthesis of benzyl alcohol.

FIG. 28 shows a representative list of solvents that have been used with TBACN.

Figure 1:
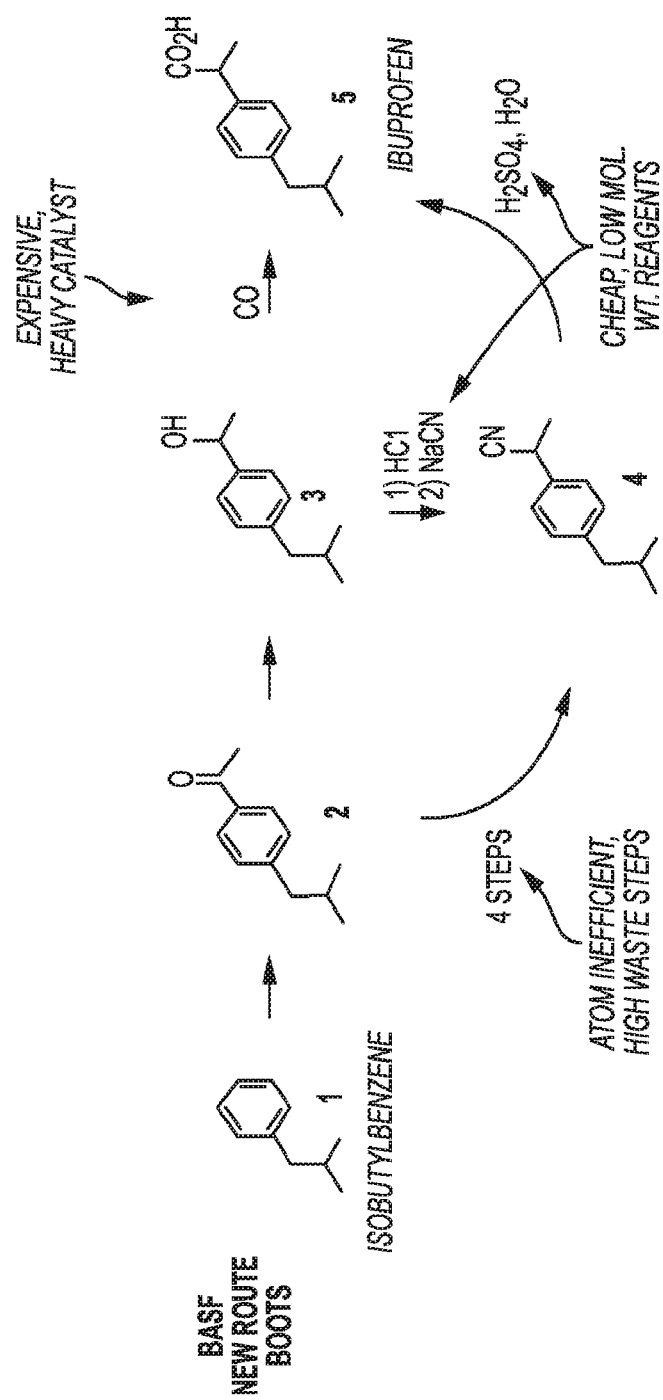
FIG. 1 shows representative synthetic routes to ibuprofen.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention now will be described more fully hereinafter with reference to the accompanying drawings, in which illustrative aspects of the invention are shown. In the drawings, the relative sizes of regions or features may be exaggerated for clarity. This invention may, however, be embodied in many different forms and should not be construed as limited to the aspects set forth herein; rather, these aspects are provided so that this disclosure will be thorough and complete, and will fully convey the scope of the invention to those skilled in the art.

This disclosure describes inventive concepts with reference to specific examples. However, the intent is to cover all modifications, equivalents, and alternatives of the inventive concepts that are consistent with this disclosure.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Further, the dates of publication provided herein may be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

For the terms "for example" and "such as," and grammatical equivalences thereof, the phrase "and without limitation" is understood to follow unless explicitly stated otherwise.

As used in the specification and in the claims, the term "comprising" can include the aspects "consisting of" and "consisting essentially of." Said another way, when the application states the invention comprises A, B, and C, it would also be contemplated that the invention can be claimed as consisting of A, B, and C. Similarly, when the application states the invention comprises A, B, and C, it would also be contemplated that the invention can be claimed as consisting essentially of A, B, and C.

References in the specification to "an embodiment," "an aspect," "implementation," etc., indicate that the embodiment described may include a particular feature, structure, or characteristic, but every embodiment may not necessarily include the particular feature, structure, or characteristic. Such phrases are not necessarily referring to the same embodiment. Further, when a particular feature, structure, or characteristic is described in connection with an embodiment, it is believed to be within the knowledge of one skilled in the art to affect such feature, structure, or characteristic in connection with other embodiments whether or not explicitly indicated.

Certain aspects of some embodiments in accordance with the disclosure may be implemented in hardware, firmware, software, or any combination thereof. Embodiments may also be implemented as instructions stored using one or more machine-readable medium may include any mechanism for storing or transmitting information in a form readable by a machine. For example, a machine-readable medium may include any suitable form of volatile or non-volatile memory. Modules, data structures, function blocks, and the like are referred to as such for ease of discussion, and are not intended to imply that any specific implementation details are required. For example, any of the described modules may be combined or divided into sub-modules, sub-processes, or other units as may be required by a particular design or implementation. In the drawings, specific arrangements or orderings of schematic elements may be shown for ease of description. However, the specific ordering or arrangement of such elements is not meant to imply that a particular order or sequence of processing, or separation of processes, is required in all embodiments. In general, schematic elements used to represent instruction blocks or modules may be implemented using any suitable form of machine-readable instruction, and each such instruction may be implemented using any suitable programming language, library, application programming interface (API), and/or other computer programming mechanisms. Similarly, schematic elements used to represent data or information may be implemented using any suitable electronic arrangement or data structure. Further, some connections, relationships or associations between elements may be simplified or not shown in the drawings so as not to obscure the disclosure. This disclosure is to be considered as exemplary and not restrictive in character, and all changes and modifications that come within the spirit of the disclosure are desired to be protected.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Also provided herein are pharmaceutically acceptable salts of the compounds described herein. As used herein, the term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. In various aspects, a non-aqueous media like ether, ethyl acetate, alcohols (e.g., methanol, ethanol, iso-propanol, or butanol) or acetonitrile (ACN) can be used. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977). Conventional methods for preparing salt forms are described, for example, in *Handbook of Pharmaceutical Salts: Properties, Selection, and Use,* Wiley-VCH, 2002.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1-OA^2$ or $—OA^1-(OA^2)_a-OA^3$, where "a" is an integer of from 1 to 200 and $A^1$, $A^2$, and $A^3$ are alkyl and/or cycloalkyl groups.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula $—C(O)H$. Throughout this specification "C(O)" is a short hand notation for a carbonyl group, i.e., C=O.

The terms "amine" or "amino" as used herein are represented by the formula $—NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula $—NH(-alkyl)$ where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula $—N(-alkyl)_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula $—C(O)OH$.

The term "ester" as used herein is represented by the formula $—OC(O)A^1$ or $—C(O)OA^1$, where $A^1$ can be alkyl, cycloalkyl, alkenyl, cycloalkenyl, alkynyl, cycloalkynyl, aryl, or heteroaryl group as described herein.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein.

The terms "halo," "halogen," or "halide," as used herein can be used interchangeably and refer to F, Cl, Br, or I.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "hydroxyl" or "hydroxyl" as used herein is represented by the formula $—OH$.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "nitro" as used herein is represented by the formula $—NO_2$.

The term "nitrile" or "cyano" as used herein is represented by the formula $—CN$ or $—C\equiv N$.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R^{\circ}$; $-(CH_2)_{0-4}OR^{\circ}$; $-O(CH_2)_{0-4}R^{\circ}$, $-O-(CH_2)_{0-4}C(O)OR^{\circ}$; $-(CH_2)_{0-4}CH(OR^{\circ})_2$; $-(CH_2)_{0-4}SR^{\circ}$; $-(CH_2)_{0-4}Ph$, which may be substituted with $R^{\circ}$; $-(CH_2)_{0-4}O(CH_2)_{0-1}Ph$ which may be substituted with $R^{\circ}$; $-CH=CHPh$, which may be substituted with $R^{\circ}$; $-(CH_2)_{0-4}O(CH_2)_{0-1}$-pyridyl which may be substituted with $R^{\circ}$; $-NO_2$; $-CN$; $-N_3$; $-(CH_2)_{0-4}N(R^{\circ})_2$; $-(CH_2)_{0-4}N(R^{\circ})C(O)R^{\circ}$; $-N(R^{\circ})C(S)R^{\circ}$; $-(CH_2)_{0-4}N(R^{\circ})C(O)NR^{\circ}_2$; $-N(R^{\circ})C(S)NR^{\circ}_2$; $-(CH_2)_{0-4}N(R^{\circ})C(O)OR^{\circ}$); $-N(R^{\circ})N(R^{\circ})C(O)R^{\circ}$; $-N(R^{\circ})N(R^{\circ})C(O)NR^{\circ}_2$; $-N(R^{\circ})N(R^{\circ})C(O)OR^{\circ}$; $-(CH_2)_{0-4}C(O)R^{\circ}$; $-C(S)R^{\circ}$; $-(CH_2)_{0-4}C(O)OR^{\circ}$; $-(CH_2)_{0-4}C(O)SR^{\circ}$; $-(CH_2)_{0-4}C(O)OSiR^{\circ}_3$; $-(CH_2)_{0-4}OC(O)R^{\circ}$; $-OC(O)(CH_2)_{0-4}SR-$, $SC(S)SR^{\circ}$; $-(CH_2)_{0-4}SC(O)R^{\circ}$; $-(CH_2)_{0-4}C(O)NR^{\circ}_2$; $-C(S)NR^{\circ}_2$; $-C(S)SR^{\circ}$; $-(CH_2)_{0-4}OC(O)NR^{\circ}_2$; $-C(O)N(OR^{\circ})R^{\circ}$; $-C(O)C(O)R^{\circ}$; $-C(O)CH_2C(O)R^{\circ}$; $-C(NOR^{\circ})R^{\circ}$; $-(CH_2)_{0-4}SSR^{\circ}$; $-(CH_2)_{0-4}S(O)_2R^{\circ}$; $-(CH_2)_{0-4}S(O)_2OR^{\circ}$; $-(CH_2)_{0-4}OS(O)_2R^{\circ}$; $-S(O)_2NR^{\circ}_2$; $-(CH_2)_{0-4}S(O)R^{\circ}$; $-N(R^{\circ})S(O)_2NR^{\circ}_2$; $-N(R^{\circ})S(O)_2R^{\circ}$; $-N(OR^{\circ})R^{\circ}$; $-C(NH)NR^{\circ}_2$; $-P(O)_2R^{\circ}$; $-P(O)R^{\circ}_2$; $-OP(O)R^{\circ}_2$; $-OP(O)(OR^{\circ})_2$; $SiR^{\circ}_3$; $-(C_{1-4}$ straight or branched alkylene)$O-N(R^{\circ})_2$; or $-(C_{1-4}$ straight or branched alkylene)$C(O)O-N(R^{\circ})_2$, wherein each $R^{\circ}$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^{\circ}$ (or the ring formed by taking two independent occurrences of $R^{\circ}$ together with their intervening atoms), are independently halogen, $-(CH_2)_{0-2}R^{\bullet}$, -(haloR$^{\bullet}$), $-(CH_2)_{0-2}OH$, $-(CH_2)_{0-2}OR^{\bullet}$, $-(CH_2)_{0-2}CH(OR^{\bullet})_2$; $-O(haloR^{\bullet})$, $-CN$, $-N_3$, $-(CH_2)_{0-2}C(O)R^{\bullet}$, $-(CH_2)_{0-2}C(O)OH$, $-(CH_2)_{0-2}C(O)OR^{\bullet}$, $-(CH_2)_{0-2}SR^{\bullet}$, $-(CH_2)_{0-2}SH$, $-(CH_2)_{0-2}NH_2$, $-(CH_2)_{0-2}NHR^{\bullet}$, $-(CH_2)_{0-2}NR^{\bullet}_2$, $-NO_2$, $-SiR^{\bullet}_3$, $-C(O)SR^{\bullet}$, $-(C_{1-4}$ straight or branched alkylene)$C(O)OR^{\bullet}$, or $-SSR^{\bullet}$ wherein each $R^{\bullet}$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^{\circ}$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^{\bullet}$, -(haloR$^{\bullet}$), $-OH$, $-OR^{\bullet}$, $-O(haloR^{\bullet})$, $-CN$, $-C(O)OH$, $-C(O)OR^{\bullet}$, $-NH_2$, $-NHR^{\bullet}$, $-NR^{\bullet}_2$, or $-NO_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^{\dagger}$, $-NR^{\dagger}_2$, $-C(O)R^{\dagger}$, $-C(O)OR^{\dagger}$, $-C(O)C(O)R^{\dagger}$, $-C(O)CH_2C(O)R^{\dagger}$, $-S(O)_2R^{\dagger}$, $-S(O)_2NR^{\dagger}_2$, $-C(S)NR^{\dagger}_2$, $-C(NH)NR^{\dagger}_2$, or $-N(R^{\dagger})S(O)_2R^{\dagger}$; wherein each $R^{\dagger}$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{\dagger}$ are independently halogen, $-R^{\bullet}$, -(haloR$^{\bullet}$), $-OH$, $-OR^{\bullet}$, $-O(haloR^{\bullet})$, $-CN$, $-C(O)OH$, $-C(O)OR^{\bullet}$, $-NH_2$, $-NHR^{\bullet}$, or $-NO_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

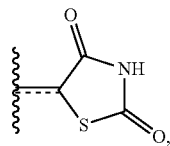

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

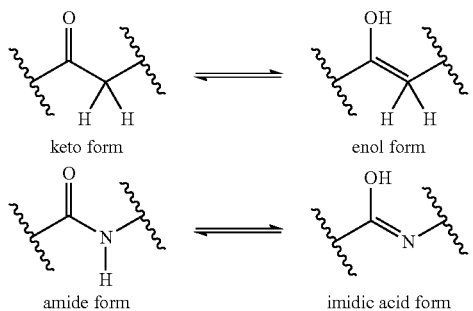

keto form    enol form
amide form    imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

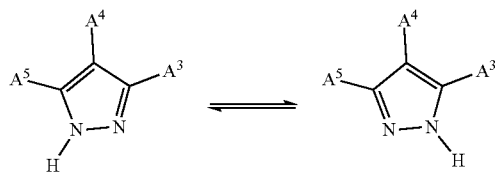

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

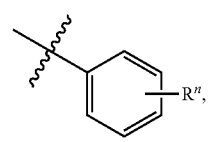

which is understood to be equivalent to a formula:

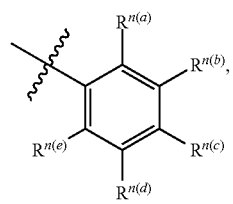

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

The following abbreviations may be used herein: AcOH (acetic acid); aq. (aqueous); atm. (atmosphere(s)); Br$_2$ (bromine); Bn (benzyl); calc. (calculated); d (doublet); dd (doublet of doublets); DCM (dichloromethane); DMF (N,N-dimethylformamide); Et (ethyl); Et$_2$O (diethyl ether); EtOAc (ethyl acetate); EtOH (ethanol); EWG (electron withdrawing group); g (gram(s)); h (hour(s)); H$_2$ (hydrogen gas); HCl (hydrochloric acid/hydrogen choride); HPLC (high performance liquid chromatography); H$_2$SO$_4$ (sulfuric acid); Hz (hertz); I$_2$ (iodine); IPA (isopropyl alcohol); J (coupling constant); KOH (potassium hydroxide); K$_3$PO$_4$ (potassium phosphate); LCMS (liquid chromatography-mass spectrometry); LiICA (lithium N-isopropylcyclohexylamide); m (multiplet); M (molar); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaBH$_3$CN (sodium cyanoborohydride); NHP (N-heterocyclic phosphine); NHP—Cl (N-heterocyclic phosphine chloride); Na$_2$CO$_3$ (sodium carbonate); NaHCO$_3$ (sodium bicarbonate); NaOH (sodium hydroxide); Na$_2$SO$_4$ (sodium sulfate); nM (nanomolar); NMR (nuclear magnetic resonance spectroscopy); PCl$_3$ (trichlorophosphine); PMP (4-methoxyphenyl); RP-HPLC (reverse phase high performance liquid chromatography); t (triplet or tertiary); t-Bu (tert-butyl); TEA (triethylamine); TFA (trifluoroacetic acid); THF (tetrahydrofuran); TLC (thin layer chromatography); µg (microgram(s)); µL (microliter(s)); µM (micromolar); wt % (weight percent).

B. Methods of Making Ibuprofen

In one aspect, the invention relates to methods of making ibuprofen, a known analgesic and non-steroidal anti-inflammatory agent. The ibuprofen of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Thus, in one aspect, disclosed are methods for preparing a cyano compound having a structure:

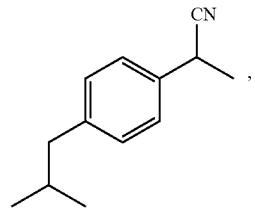

the method comprising the steps of: (a) reducing a carboxyl compound having a structure:

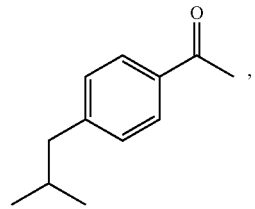

thereby producing an alcohol having a structure:

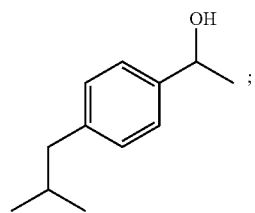

converting a hydroxyl group on the alcohol to a leaving group, thereby producing a compound having a structure:

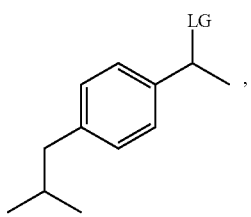

wherein LG is selected from chloro and mesyl; and (c) displacing the leaving group with a nucleophilic cyanide reagent, thereby producing the cyano compound.

The disclosed approach intercepts with the Boots process, but is one step shorter and uses reagents offering the highest atom economy, leading to minimal waste. Some versions of the disclosed approach may utilize an automated chemical synthesis platform, such as described in U.S. Provisional Patent Application No. 62/482,515. Some versions of this automated chemical synthesis platform may be referred to as "AutoSyn" or "SynFini." The disclosed approach enables continuous manufacturing from inexpensive reagents. Thus, the disclosed approach can provide the synthesis of ibuprofen with reduced cost.

For example, without wishing to be bound by theory, the synthesis of ibuprofen begins with isobutybenzene. Isobutylbenzene undergoes Friedel-Crafts acylation with an acetyl source including, but not limited to, acetyl chloride, acetic anhydride and aluminum chloride, to afford 1-(4-isobutylphenyl)ethanone. This ketone is reduced to the corresponding to the corresponding alcohol with a reducing agent. Suitable reducing agents include, but are not limited to, diisobutylaluminum hydride, sodium borohydride, lithium borohydride, and hydrogen (with a metal catalyst). The alcohol is converted to a derivative with a leaving group, e.g., mesylate (by reaction of the alcohol with a mesylating agent such as mesyl anhydride or mesyl chloride) or chloride (by reaction of the alcohol with hydrochloric acid, thionyl chloride, or some other chlorinating agent). The leaving group is displaced by cyanide to afford 2-(4-isobutylphenyl)propanenitrile. This reaction can be effected by treatment of 1-(1-chloroethyl)-4-isobutylbenzene (or sulfonate analog) with various salt forms of cyanide including sodium, potassium, and tetraalkylammonium. Finally, the cyano group of 2-(4-isobutylphenyl)propanenitrile isn hydrolyzed under either acidic or basic conditions.

Using an appropriate flow chemistry system, these reactions may be performed as individual steps or as multi-step operations by feeding the output of one reactor into the inlet of the next reactor. An aqueous separator is necessary following the conversion of the alcohol intermediate into the corresponding chloride. The final product ibuprofen may be purified away from the corresponding primary amide side-product by an acid/base extraction, performed by sequential treatment of the flow stream with aqueous sodium hydroxide and then aqueous hydrochloric acid.

In a further aspect, the reducing step is an asymmetric reduction.

In a further aspect, LG is a leaving a group selected from —Cl and a mesyl group. In an even further aspect, LG is —Cl. In yet a further aspect, LG is a mesyl group.

In a further aspect, displacing is via a stereospecific displacement reaction. In a still further aspect, displacing is via a non-stereospecific displacement reaction.

In a further aspect, the nucleophilic cyanide reagent is selected from potassium cyanide, sodium cyanide, and tetrabutylammonium cyanide.

In a further aspect, the cyano compound has a structure:

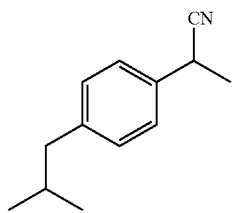

In a further aspect, the carboxyl compound has a structure:

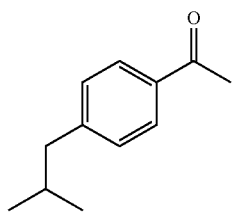

In a further aspect, the alcohol has a structure:

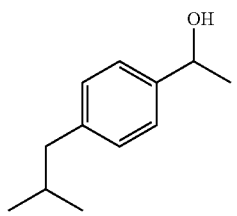

In a further aspect, the compound has a structure:

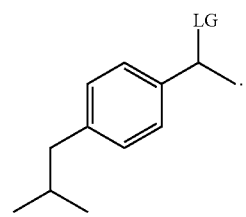

In a further aspect, the method further comprises hydrolyzing the cyano compound, thereby producing a carboxylic acid having a structure represented by a formula:

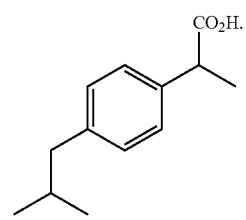

1. Route I

In one aspect, ibuprofen derivatives can be prepared as shown below.

SCHEME 1A.

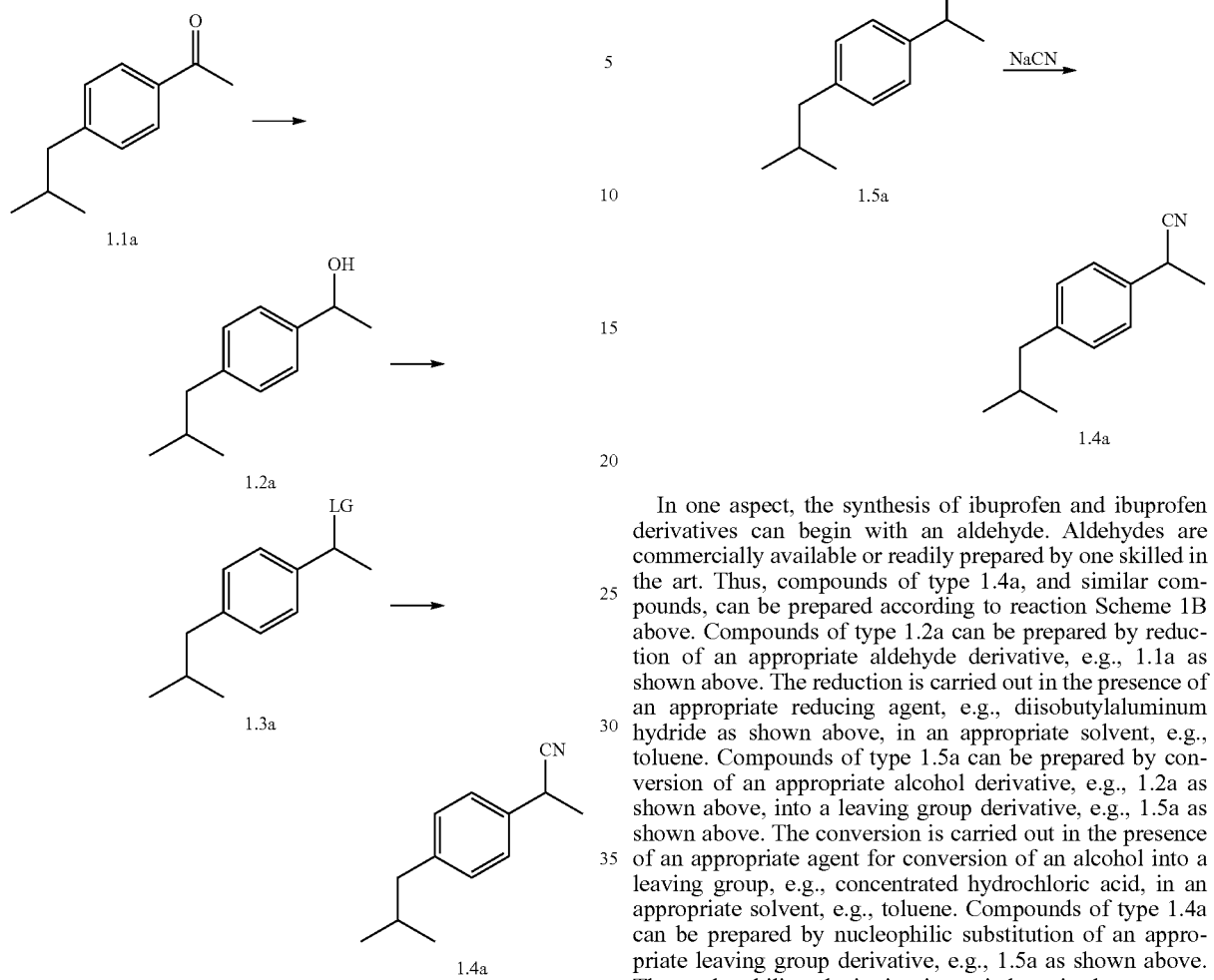

Compounds are represented in generic form, with substituents as noted in compound descriptions elsewhere herein. A more specific example is set forth below.

SCHEME 1B.

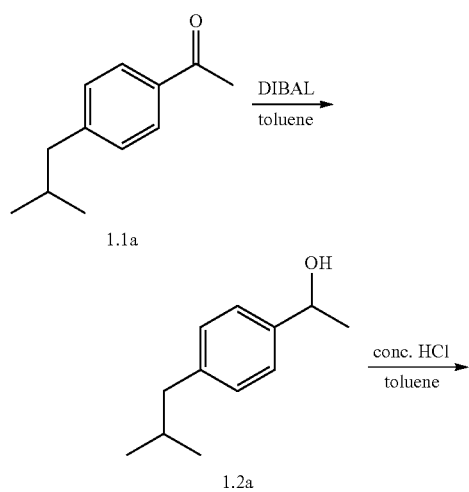

In one aspect, the synthesis of ibuprofen and ibuprofen derivatives can begin with an aldehyde. Aldehydes are commercially available or readily prepared by one skilled in the art. Thus, compounds of type 1.4a, and similar compounds, can be prepared according to reaction Scheme 1B above. Compounds of type 1.2a can be prepared by reduction of an appropriate aldehyde derivative, e.g., 1.1a as shown above. The reduction is carried out in the presence of an appropriate reducing agent, e.g., diisobutylaluminum hydride as shown above, in an appropriate solvent, e.g., toluene. Compounds of type 1.5a can be prepared by conversion of an appropriate alcohol derivative, e.g., 1.2a as shown above, into a leaving group derivative, e.g., 1.5a as shown above. The conversion is carried out in the presence of an appropriate agent for conversion of an alcohol into a leaving group, e.g., concentrated hydrochloric acid, in an appropriate solvent, e.g., toluene. Compounds of type 1.4a can be prepared by nucleophilic substitution of an appropriate leaving group derivative, e.g., 1.5a as shown above. The nucleophilic substitution is carried out in the presence of an appropriate cyanide agent, e.g., sodium cyanide as shown above. As can be appreciated by one skilled in the art, the above reaction provides an example of a generalized approach wherein compounds similar in structure to the specific reactants above (compounds similar to compounds of type 1.1a, 1.2a, and 1.3a), can be substituted in the reaction to provide ibuprofen derivatives similar to Formula 1.4a.

2. Route II

In one aspect, ibuprofen can be prepared as shown below.

SCHEME 2A.

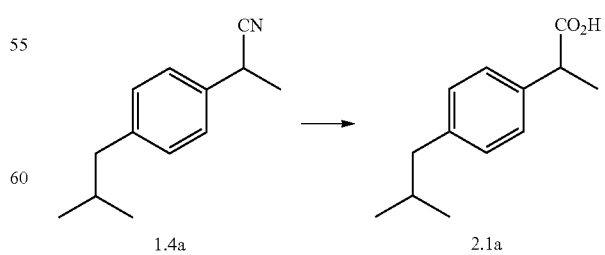

Compounds are represented in generic form, with substituents as noted in compound descriptions elsewhere herein. A more specific example is set forth below.

SCHEME 2B.

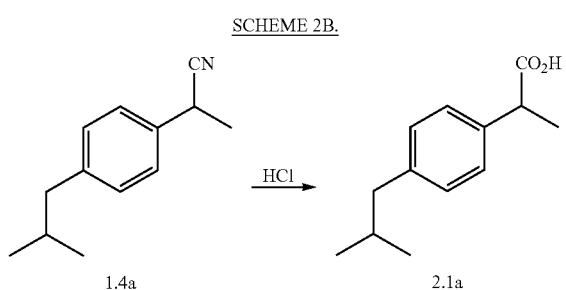

In one aspect, the synthesis of ibuprofen and ibuprofen derivatives can begin with a cyanide compound. Cyanides can be readily prepared by one skilled in the art and as disclosed herein. Thus, compounds of type 2.1a, and similar compounds, can be prepared according to reaction Scheme 2B above. Compounds of type 2.1a can be prepared by hydrolysis of an appropriate cyanide derivative, e.g., 1.4a as shown above. The hydrolysis is carried out in the presence of an appropriate hydrolysing agent, e.g., hydrochloric acid as shown above. As can be appreciated by one skilled in the art, the above reaction provides an example of a generalized approach wherein compounds similar in structure to the specific reactants above (compounds similar to compounds of type 1.4a), can be substituted in the reaction to provide ibuprofen and ibuprofen derivatives similar to Formula 2.1a.

3. Route III

In one aspect, ibuprofen derivatives can be prepared as shown below.

SCHEME 3A.

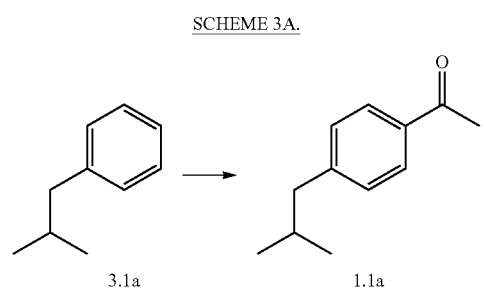

Compounds are represented in generic form, with substituents as noted in compound descriptions elsewhere herein. A more specific example is set forth below.

SCHEME 3B.

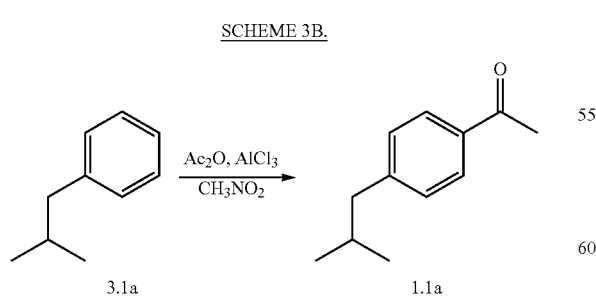

In one aspect, the synthesis of ibuprofen and ibuprofen derivatives can begin with a benzene derivative. Benzene derivatives can be readily prepared by one skilled in the art or are commercially available. Thus, compounds of type 1.1a, and similar compounds, can be prepared according to reaction Scheme 3B above. Compounds of type 1.1a can be prepared by Friedel-Crafts acylation of an appropriate benzene derivative, e.g., 3.1a as shown above. The acylation is carried out in the presence of an appropriate acylating agent, e.g., acetic anhydride as shown above, and an appropriate Lewis acid, e.g., aluminium chloride, in an appropriate solvent, e.g., nitromethane. As can be appreciated by one skilled in the art, the above reaction provides an example of a generalized approach wherein compounds similar in structure to the specific reactants above (compounds similar to compounds of type 3.1a), can be substituted in the reaction to provide ibuprofen and ibuprofen derivatives similar to Formula 1.1a.

In further aspects, homologated ibuprofen derivatives can be prepared as shown below.

SCHEME 3C.

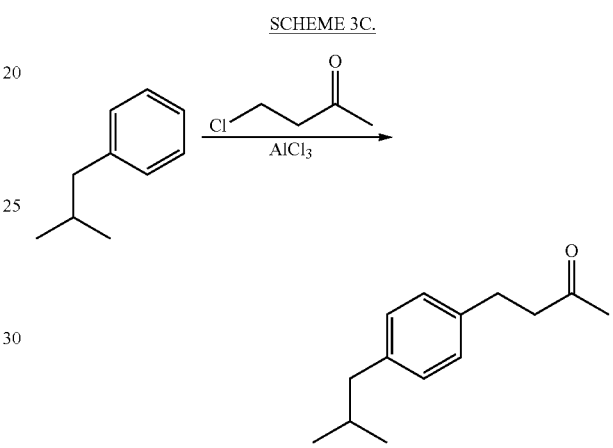

Benzene derivatives (e.g., isobutylbenzene), and similar compounds, can be reacted under by Friedel-Crafts alkylation conditions (i.e., with an appropriate alkylating agent, e.g., alkyl halide as shown above, and an appropriate Lewis acid, e.g., aluminium chloride, in an appropriate solvent). In one aspect, the alkyl halide can be an alkyl chloride that is functionalized with a ketone functionality, as shown above. As can be appreciated by one skilled in the art, the above reaction provides an example of a generalized approach wherein compounds similar in structure to the specific reactants above, can be substituted in the reaction to provide desired ibuprofen and ibuprofen derivatives.

In further aspects, homologated ibuprofen derivatives can be prepared as shown below.

SCHEME 3D.

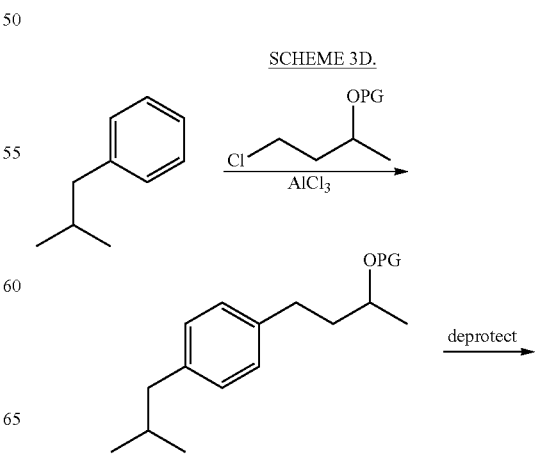

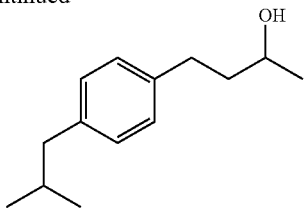

Benzene derivatives (e.g., isobutylbenzene), and similar compounds, can be reacted under by Friedel-Crafts alkylation conditions (i.e., with an appropriate alkylating agent, e.g., alkyl halide as shown above, and an appropriate Lewis acid, e.g., aluminium chloride, in an appropriate solvent). In one aspect, the alkyl halide can be an alkyl chloride that is functionalized with a protected alcohol functionality (OPG), as shown above. The protecting group (PG) can be subsequently removed to yield an alcohol functionality. As can be appreciated by one skilled in the art, the above reaction provides an example of a generalized approach wherein compounds similar in structure to the specific reactants above, can be substituted in the reaction to provide desired ibuprofen and ibuprofen derivatives.

C. Methods of Making Derivatives of Ibuprofen and Naproxen

In one aspect, the invention relates to methods of making derivatives of ibuprofen and naproxen, known analgesics and non-steroidal anti-inflammatory agents. The ibuprofen and naproxen derivatives of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Thus, in one aspect, disclosed are methods for preparing a cyano compound having a structure represented by a formula:

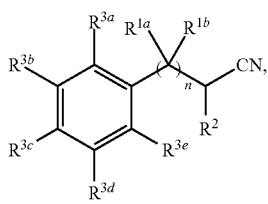

wherein n is selected from 0, 1, 2, 3, and 4; wherein each of $R^{1a}$ and $R^{1b}$, when present, is independently selected from hydrogen and C1-C4 alkyl; wherein $R^2$ is selected from hydrogen and C1-C4 alkyl; and wherein each of $R^{3a}$, $R^{3b}$, $R^{3c}$, $R^{3d}$, and $R^{3e}$ is independently selected from hydrogen, halogen, —OH, —NH$_2$, —NO$_2$, —CN, C1-C4 alkyl, and C1-C4 alkoxy; or wherein any two of $R^{3a}$, $R^{3b}$, $R^{3c}$, $R^{3d}$, and $R^{3e}$ together comprise a structure represented by a formula:

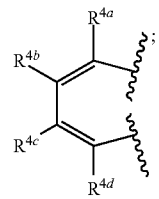

and
wherein each of $R^{4a}$, $R^{4b}$, $R^{4c}$, and $R^{4d}$, when present, is independently selected from hydrogen, halogen, —OH, —NH$_2$, —NO$_2$, —CN, C1-C4 alkyl, and C1-C4 alkoxy, the method comprising the steps of: (a) reducing a carboxyl compound having a structure represented by a formula:

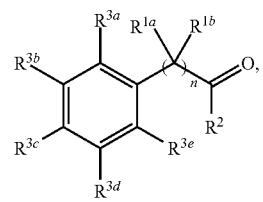

thereby producing an alcohol having a structure represented by a formula:

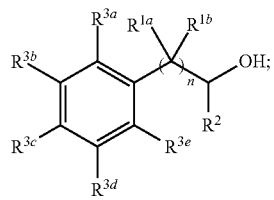

(b) converting a hydroxyl group on the alcohol to a leaving group, thereby producing a compound having a structure represented by a formula:

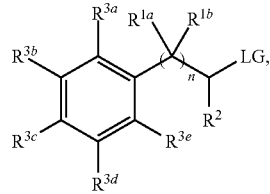

wherein LG is a leaving group; and (c) displacing the leaving group with a nucleophilic cyanide reagent, thereby producing the cyano compound.

In a further aspect, the reducing step is an asymmetric reduction.

In a further aspect, LG is a leaving a group. Examples of a leaving group include, but are not limited to, methanesulfonate (mesyl), triflate, p-toluenesulfonate, iodide, bromide, chloride, and trifluoroacetate. In a still further aspect, LG is selected from a halide and a mesyl group. In yet a further aspect, LG is selected from —Cl and a mesyl group. In an even further aspect, LG is a halide. In a still further aspect, LG is —Cl. In yet a further aspect, LG is a mesyl group.

In a further aspect, displacing is via a stereospecific displacement reaction. In a still further aspect, displacing is via a non-stereospecific displacement reaction.

In a further aspect, the nucleophilic cyanide reagent is selected from potassium cyanide, sodium cyanide, and tetrabutylammonium cyanide.

In a further aspect, the cyano compound has a structure represented by a formula:

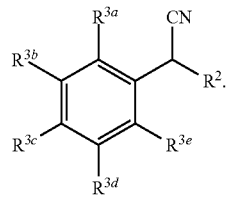

In a still further aspect, the cyano compound has a structure represented by a formula:

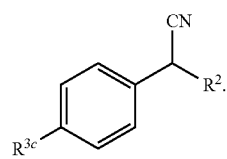

In yet a further aspect, the cyano compound has a structure represented by a formula:

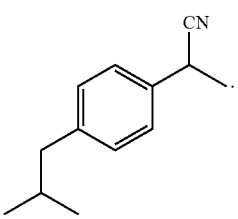

In an even further aspect, the cyano compound has a structure represented by a formula:

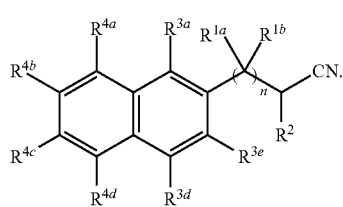

In a still further aspect, the cyano compound has a structure represented by a formula:

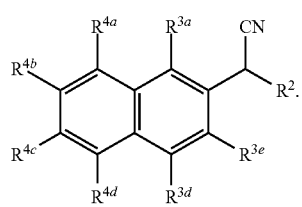

In yet a further aspect, the cyano compound has a structure represented by a formula:

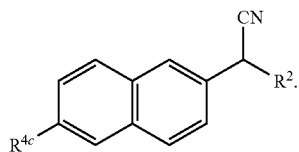

In an even further aspect, the cyano compound has a structure represented by a formula:

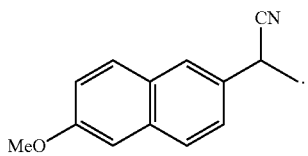

In a still further aspect, the cyano compound has a structure represented by a formula:

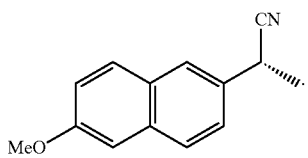

In a further aspect, the carboxyl compound has a structure represented by a formula:

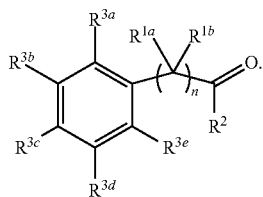

In a still further aspect, the carboxyl compound has a structure represented by a formula:

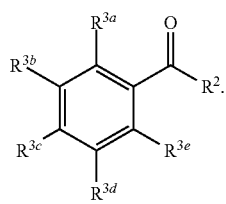

In yet a further aspect, the carboxyl compound has a structure represented by a formula:

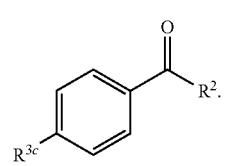

In an even further aspect, the carboxyl compound has a structure represented by a formula:

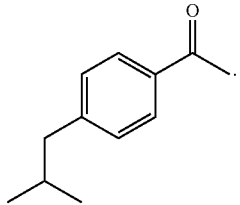

In a still further aspect, the carboxyl compound has a structure represented by a formula:

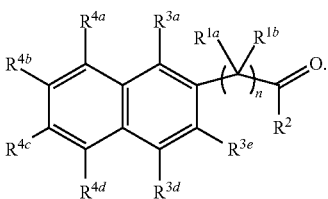

In yet a further aspect, the carboxyl compound has a structure represented by a formula:

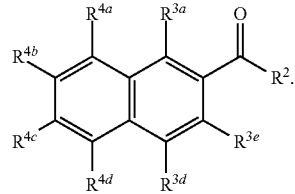

In an even further aspect, the carboxyl compound has a structure represented by a formula:

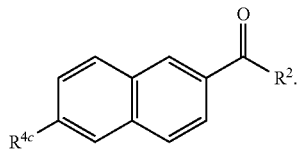

In a still further aspect, the carboxyl compound has a structure represented by a formula:

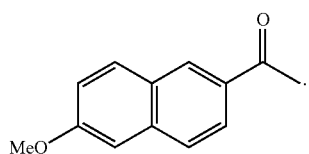

In a further aspect, the alcohol has a structure represented by a formula:

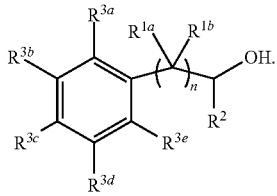

In a still further aspect, the alcohol has a structure represented by a formula:

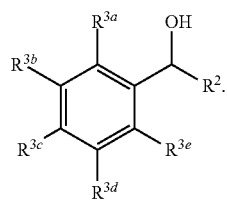

In yet a further aspect, the alcohol has a structure represented by a formula:

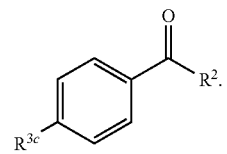

In an even further aspect, the alcohol has a structure represented by a formula:

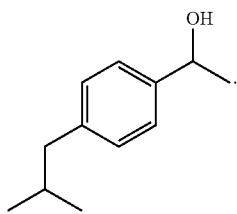

In a still further aspect, the alcohol has a structure represented by a formula:

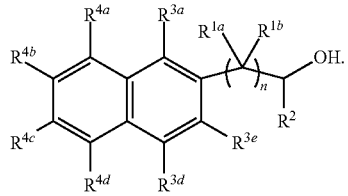

In yet a further aspect, the alcohol has a structure represented by a formula:

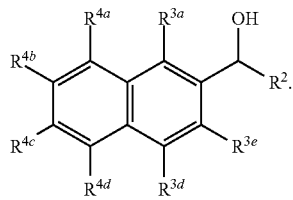

In an even further aspect, the alcohol has a structure represented by a formula:

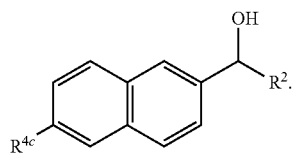

In a still further aspect, the alcohol has a structure represented by a formula:

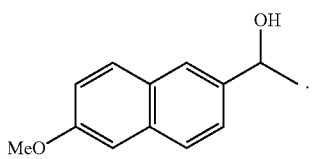

In yet a further aspect, the alcohol has a structure represented by a formula:

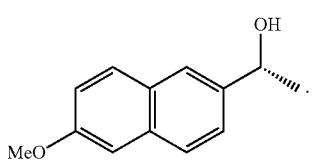

In a further aspect, the compound has a structure represented by a formula:

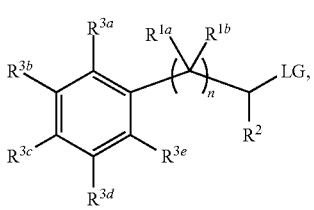

wherein LG is a leaving group.

In a still further aspect, the compound has a structure represented by a formula:

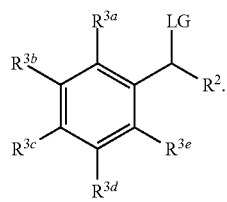

In yet a further aspect, the compound has a structure represented by a formula:

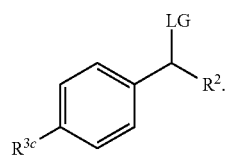

In an even further aspect, the compound has a structure represented by a formula:

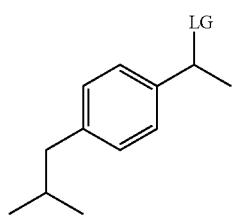

In a still further aspect, the compound has a structure represented by a formula:

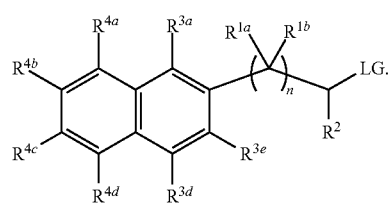

In yet a further aspect, the compound has a structure represented by a formula:

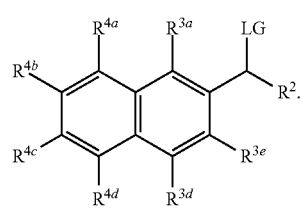

In an even further aspect, the compound has a structure represented by a formula:

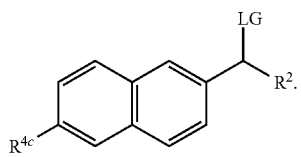

In a still further aspect, the compound has a structure represented by a formula:

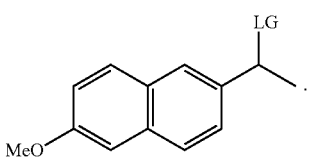

In yet a further aspect, the compound has a structure represented by a formula:

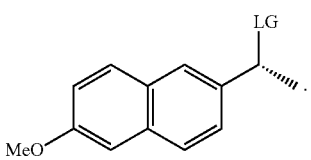

In a further aspect, the method further comprises hydrolyzing the cyano compound, thereby producing a carboxylic acid having a structure represented by a formula:

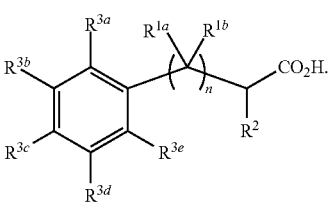

In a still further aspect, the carboxylic has a structure represented by a formula:

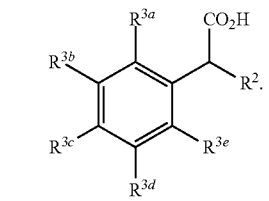

In yet a further aspect, the carboxylic acid has a structure represented by a formula:

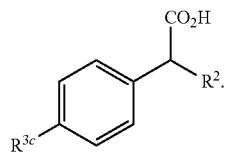

In an even further aspect, the carboxylic acid has a structure represented by a formula:

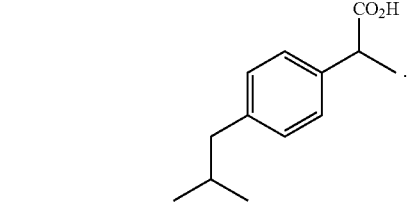

In a still further aspect, the carboxylic acid has a structure represented by a formula:

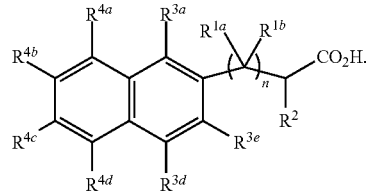

In yet a further aspect, the carboxylic acid has a structure represented by a formula:

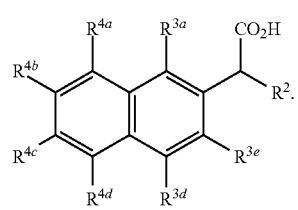

In an even further aspect, the carboxylic acid has a structure represented by a formula:

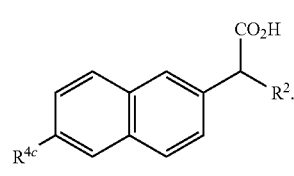

In a still further aspect, the carboxylic acid has a structure represented by a formula:

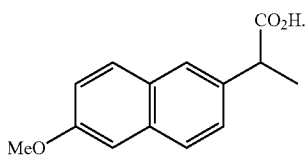

In yet a further aspect, the carboxylic acid has a structure represented by a formula:

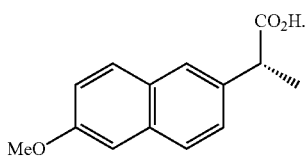

1. Route IV

In one aspect, ibuprofen, naproxen, and derivatives thereof can be prepared as shown below.

SCHEME 4A.

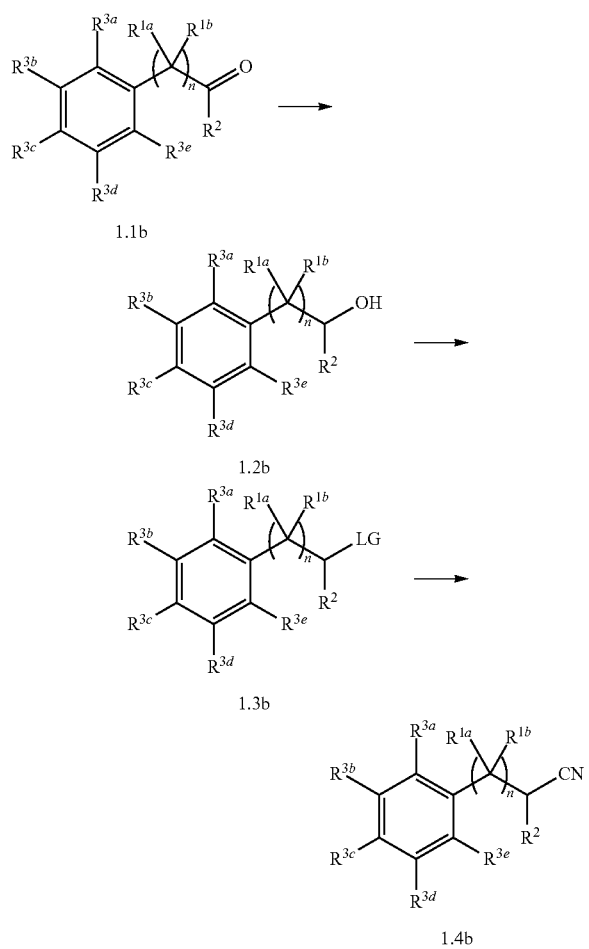

Compounds are represented in generic form, with substituents as noted in compound descriptions elsewhere herein. A more specific example is set forth below.

SCHEME 4B.

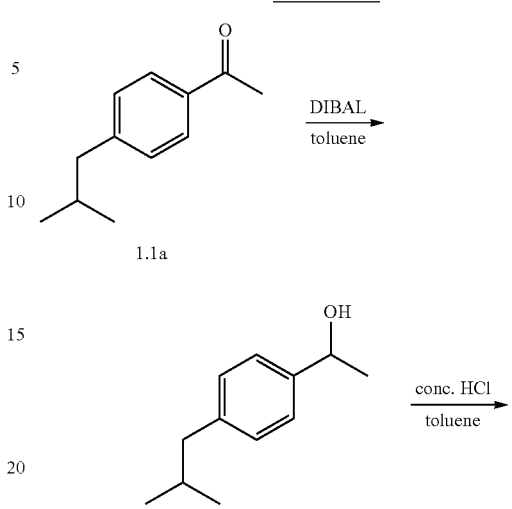

In one aspect, the synthesis of ibuprofen can begin with an aldehyde. Aldehydes are commercially available or readily prepared by one skilled in the art. Thus, compounds of type 1.4a, and similar compounds, can be prepared according to reaction Scheme 4B above. Compounds of type 1.2a can be prepared by reduction of an appropriate aldehyde derivative, e.g., 1.1a as shown above. The reduction is carried out in the presence of an appropriate reducing agent, e.g., diisobutylaluminum hydride as shown above, in an appropriate solvent, e.g., toluene. Compounds of type 1.5a can be prepared by conversion of an appropriate alcohol derivative, e.g., 1.2a as shown above, into a leaving group derivative, e.g., 1.5a as shown above. The conversion is carried out in the presence of an appropriate agent for conversion of an alcohol into a leaving group, e.g., concentrated hydrochloric acid, in an appropriate solvent, e.g., toluene. Compounds of type 1.4a can be prepared by nucleophilic substitution of an appropriate leaving group derivative, e.g., 1.5a as shown above. The nucleophilic substitution is carried out in the presence of an appropriate cyanide agent, e.g., sodium cyanide as shown above. As can be appreciated by one skilled in the art, the above reaction provides an example of a generalized approach wherein compounds similar in structure to the specific reactants above (compounds similar to compounds of type 1.1b, 1.2b, and 1.3b), can be substituted in the reaction to provide ibuprofen, naproxen, and derivatives thereof similar to Formula 1.4b.

2. Route V

In one aspect, ibuprofen, naproxen, and derivatives thereof can be prepared as shown below.

SCHEME 5A.

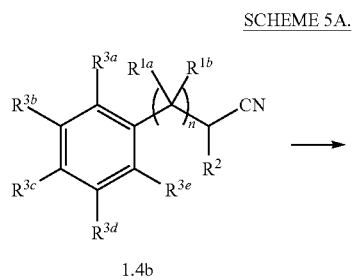

1.4b

SCHEME 6A.

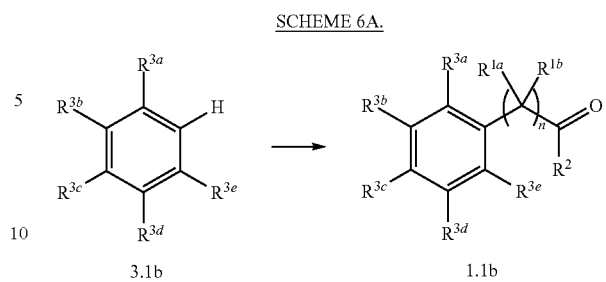

3.1b                    1.1b

Compounds are represented in generic form, with substituents as noted in compound descriptions elsewhere herein. A more specific example is set forth below.

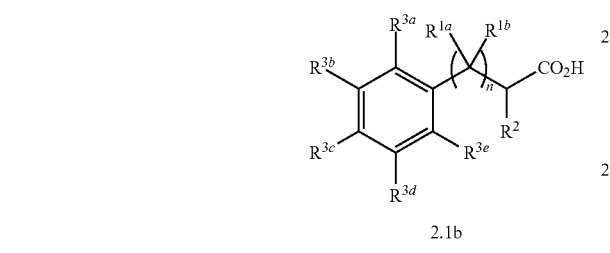

2.1b

SCHEME 6B.

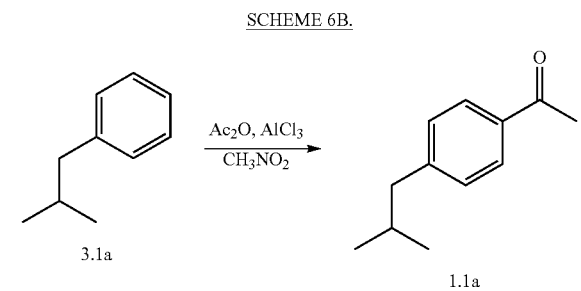

3.1a                    1.1a

In one aspect, the synthesis of ibuprofen and ibuprofen derivatives can begin with a benzene or napthyl derivative. Benzene derivatives and naphthyl derivatives can be readily prepared by one skilled in the art or are commercially available. Thus, compounds of type 1.1a, and similar compounds, can be prepared according to reaction Scheme 6B above. Compounds of type 1.1a can be prepared by Friedel-Crafts acylation of an appropriate benzene derivative, e.g., 3.1a as shown above. The acylation is carried out in the presence of an appropriate acylating agent, e.g., acetic anhydride as shown above, and an appropriate Lewis acid, e.g., aluminium chloride, in an appropriate solvent, e.g., nitromethane. As can be appreciated by one skilled in the art, the above reaction provides an example of a generalized approach wherein compounds similar in structure to the specific reactants above (compounds similar to compounds of type 3.1b), can be substituted in the reaction to provide ibuprofen and ibuprofen derivatives similar to Formula 1.1b.

D. Methods of Making Derivatives of Naproxen

In one aspect, the invention relates to methods of making derivatives of naproxen, a known analgesic and non-steroidal anti-inflammatory agent. The naproxen derivatives of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Thus, in one aspect, disclosed are methods for preparing a carboxylic acid having a structure represented by a formula:

Compounds are represented in generic form, with substituents as noted in compound descriptions elsewhere herein. A more specific example is set forth below.

SCHEME 5B.

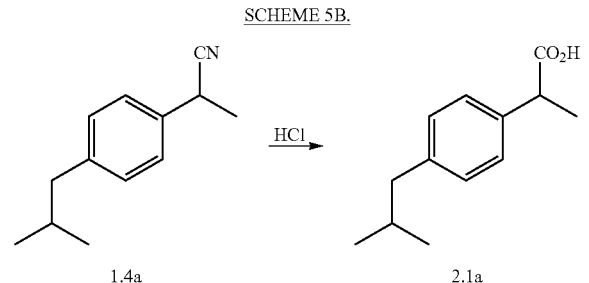

1.4a                    2.1a

In one aspect, the synthesis of ibuprofen, naproxen, and derivatives thereof can begin with a cyanide compound. Cyanides can be readily prepared by one skilled in the art and as disclosed herein. Thus, compounds of type 2.1a, and similar compounds, can be prepared according to reaction Scheme 5B above. Compounds of type 2.1a can be prepared by hydrolysis of an appropriate cyanide derivative, e.g., 1.4a as shown above. The hydrolysis is carried out in the presence of an appropriate hydrolysing agent, e.g., hydrochloric acid as shown above. As can be appreciated by one skilled in the art, the above reaction provides an example of a generalized approach wherein compounds similar in structure to the specific reactants above (compounds similar to compounds of type 1.4b), can be substituted in the reaction to provide ibuprofen, naproxen, and derivatives thereof, similar to Formula 2.1b.

3. Route VI

In one aspect, ibuprofen derivatives can be prepared as shown below.

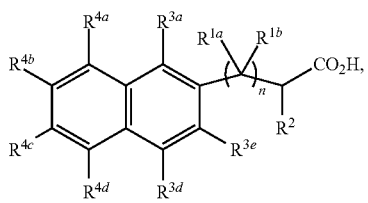

wherein n is selected from 0, 1, 2, 3, and 4; wherein each of $R^{1a}$ and $R^{1b}$, when present, is independently selected from hydrogen and C1-C4 alkyl; wherein $R^2$ is selected from hydrogen and C1-C4 alkyl; and wherein each of $R^{3a}$, $R^{3d}$, and $R^{3e}$ is independently selected from hydrogen, halogen, —OH, —NH$_2$, —NO$_2$, —CN, C1-C4 alkyl, and C1-C4 alkoxy; and wherein each of $R^{4a}$, $R^{4b}$, $R^{4c}$, and $R^{4d}$ is independently selected from hydrogen, halogen, —OH, —NH$_2$, —NO$_2$, —CN, C1-C4 alkyl, and C1-C4 alkoxy, the method comprising the steps of:

(a) converting a hydroxyl group on an alcohol to a leaving group, wherein the alcohol has a structure represented by a formula:

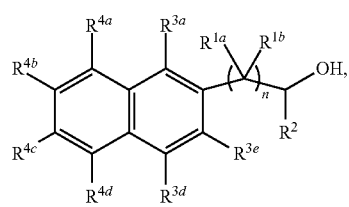

thereby producing a compound having a structure represented by a formula:

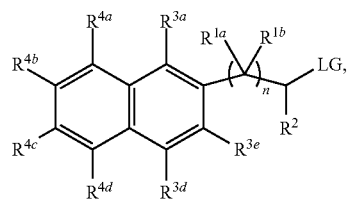

wherein LG is a leaving group; (b) displacing the leaving group with a nucleophilic cyanide reagent, thereby producing a cyano compound having a structure represented by a formula:

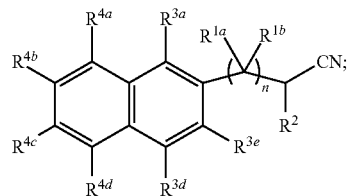

and
(c) hydrolyzing the cyano compound, thereby producing the carboxylic acid.

In a further aspect, LG is a leaving a group. Examples of a leaving group include, but are not limited to, methanesulfonate (mesyl), triflate, p-toluenesulfonate, iodide, bromide, chloride, and trifluoroacetate. In a still further aspect, LG is selected from a halide and a mesyl group. In yet a further aspect, LG is selected from —Cl and a mesyl group. In an even further aspect, LG is a halide. In a still further aspect, LG is —Cl. In yet a further aspect, LG is a mesyl group.

In a further aspect, displacing is via a stereospecific displacement reaction. In a still further aspect, displacing is via a non-stereospecific displacement reaction.

In a further aspect, the nucleophilic cyanide reagent is selected from potassium cyanide, sodium cyanide, and tetrabutylammonium cyanide.

In a further aspect, the carboxylic acid has a structure represented by a formula:

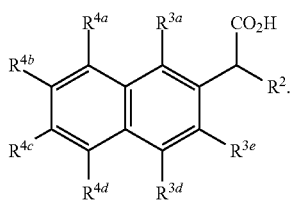

In a still further aspect, the carboxylic acid has a structure represented by a formula:

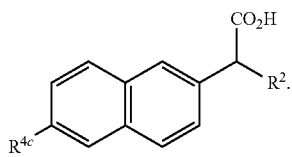

In yet a further aspect, the carboxylic acid has a structure represented by a formula:

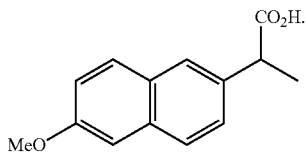

In an even further aspect, the carboxylic acid has a structure represented by a formula:

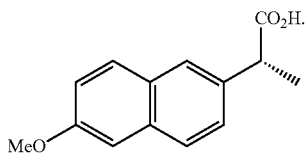

In a further aspect, the alcohol has a structure represented by a formula:

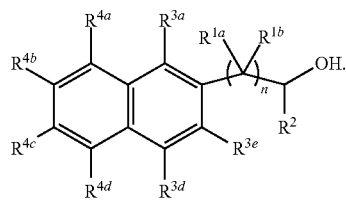

In a still further aspect, the alcohol has a structure represented by a formula:

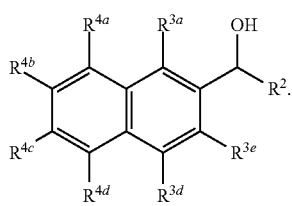

In yet a further aspect, the alcohol has a structure represented by a formula:

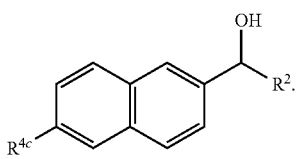

In an even further aspect, the alcohol has a structure represented by a formula:

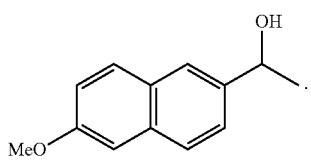

In a still further aspect, the alcohol has a structure represented by a formula:

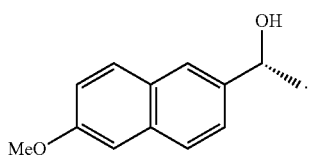

In a further aspect, the compound has a structure represented by a formula:

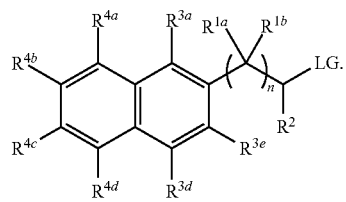

In a still further aspect, the compound has a structure represented by a formula:

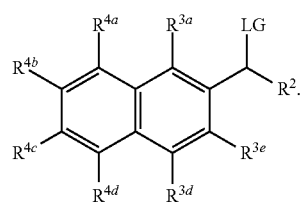

In yet a further aspect, the compound has a structure represented by a formula:

In an even further aspect, the compound has a structure represented by a formula:

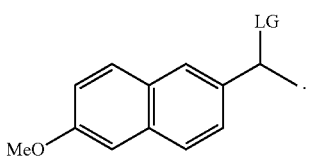

In a still further aspect, the compound has a structure represented by a formula:

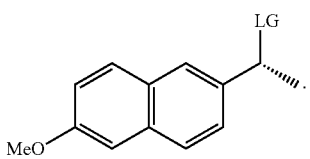

In a further aspect, the cyano compound has a structure represented by a formula:

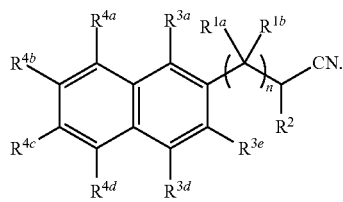

In a still further aspect, the cyano compound has a structure represented by a formula:

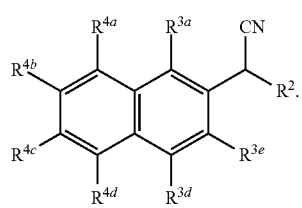

In yet a further aspect, the cyano compound has a structure represented by a formula:

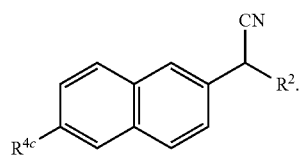

In an even further aspect, the cyano compound has a structure represented by a formula:

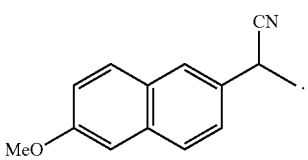

In a still further aspect, the cyano compound has a structure represented by a formula:

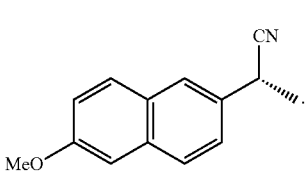

1. Route VII

In one aspect, naproxen and naproxen derivatives can be prepared as shown below.

SCHEME 7A.

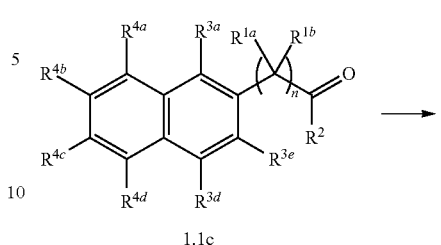

1.1c

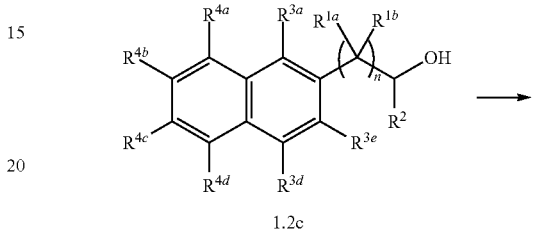

1.2c

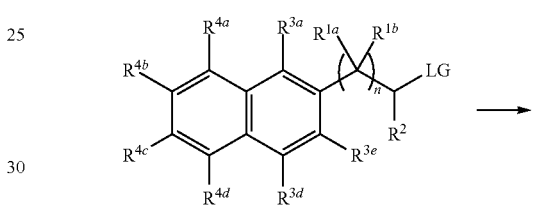

1.3c

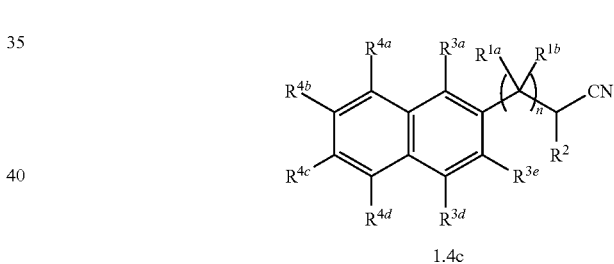

1.4c

Compounds are represented in generic form, with substituents as noted in compound descriptions elsewhere herein. A more specific example is set forth below.

SCHEME 7B.

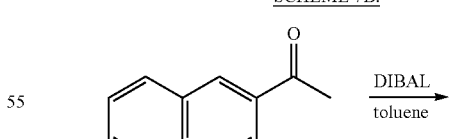

1.5c

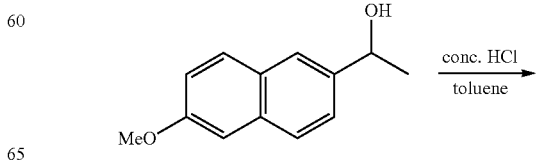

1.6

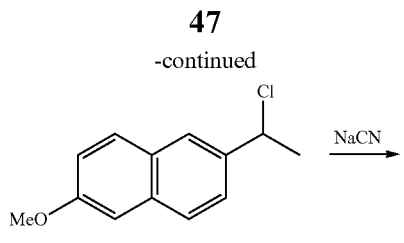

1.7

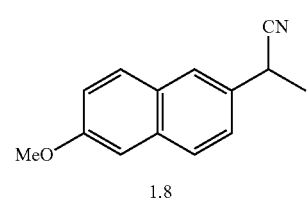

1.8

In one aspect, the synthesis of ibuprofen can begin with an aldehyde. Aldehydes are commercially available or readily prepared by one skilled in the art. Thus, compounds of type 1.8, and similar compounds, can be prepared according to reaction Scheme 7B above. Compounds of type 1.6 can be prepared by reduction of an appropriate aldehyde derivative, e.g., 1.5c as shown above. The reduction is carried out in the presence of an appropriate reducing agent, e.g., diisobutylaluminum hydride as shown above, in an appropriate solvent, e.g., toluene. Compounds of type 1.7 can be prepared by conversion of an appropriate alcohol derivative, e.g., 1.6 as shown above, into a leaving group derivative, e.g., 1.7 as shown above. The conversion is carried out in the presence of an appropriate agent for conversion of an alcohol into a leaving group, e.g., concentrated hydrochloric acid, in an appropriate solvent, e.g., toluene. Compounds of type 1.8 can be prepared by nucleophilic substitution of an appropriate leaving group derivative, e.g., 1.7 as shown above. The nucleophilic substitution is carried out in the presence of an appropriate cyanide agent, e.g., sodium cyanide as shown above. As can be appreciated by one skilled in the art, the above reaction provides an example of a generalized approach wherein compounds similar in structure to the specific reactants above (compounds similar to compounds of type 1.1c, 1.2c, and 1.3c), can be substituted in the reaction to provide naproxen and naproxen derivatives thereof similar to Formula 1.4c.

2. Route VIII

In one aspect, ibuprofen, naproxen, and derivatives thereof can be prepared as shown below.

SCHEME 8A.

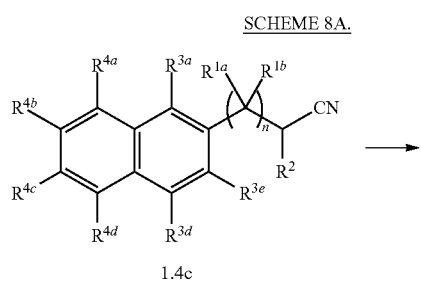

1.4c

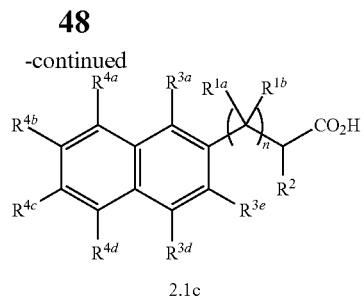

2.1c

Compounds are represented in generic form, with substituents as noted in compound descriptions elsewhere herein. A more specific example is set forth below.

SCHEME 8B.

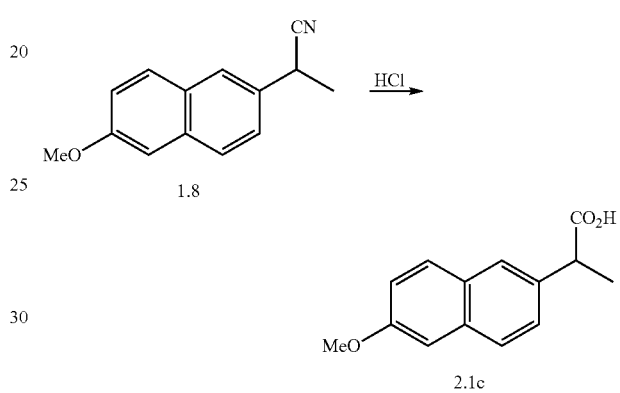

2.1c

In one aspect, the synthesis of naproxen and naproxen derivatives can begin with a cyanide compound. Cyanides can be readily prepared by one skilled in the art and as disclosed herein. Thus, compounds of type 2.1c, and similar compounds, can be prepared according to reaction Scheme 8B above. Compounds of type 2.1c can be prepared by hydrolysis of an appropriate cyanide derivative, e.g., 1.8 as shown above. The hydrolysis is carried out in the presence of an appropriate hydrolysing agent, e.g., hydrochloric acid as shown above. As can be appreciated by one skilled in the art, the above reaction provides an example of a generalized approach wherein compounds similar in structure to the specific reactants above (compounds similar to compounds of type 1.4c), can be substituted in the reaction to provide naproxen and naproxen derivatives, similar to Formula 2.1c.

3. Route IX

In one aspect, naproxen derivatives can be prepared as shown below.

SCHEME 9A.

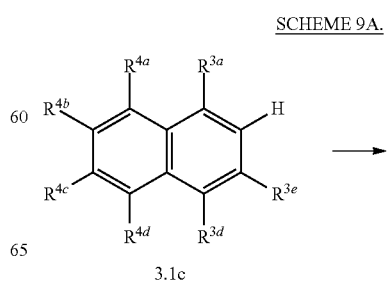

3.1c

49

-continued

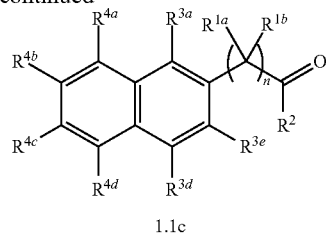

1.1c

Compounds are represented in generic form, with substituents as noted in compound descriptions elsewhere herein. A more specific example is set forth below.

SCHEME 9B.

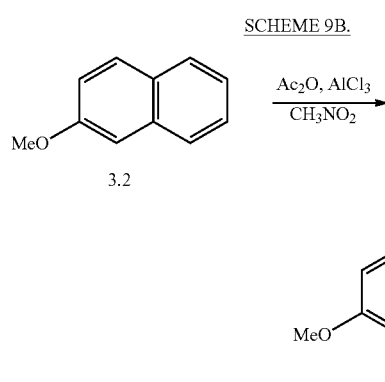

In one aspect, the synthesis of ibuprofen and ibuprofen derivatives can begin with a napthyl derivative. Napthyl derivatives can be readily prepared by one skilled in the art or are commercially available. Thus, compounds of type 1.5c, and similar compounds, can be prepared according to reaction Scheme 9B above. Compounds of type 1.5c can be prepared by Friedel-Crafts acylation of an appropriate benzene derivative, e.g., 3.2 as shown above. The acylation is carried out in the presence of an appropriate acylating agent, e.g., acetic anhydride as shown above, and an appropriate Lewis acid, e.g., aluminium chloride, in an appropriate solvent, e.g., nitromethane. As can be appreciated by one skilled in the art, the above reaction provides an example of a generalized approach wherein compounds similar in structure to the specific reactants above (compounds similar to compounds of type 3.1c), can be substituted in the reaction to provide naproxen and naproxen derivatives similar to Formula 1.1c.

E. Compounds

In one aspect, the invention relates ibuprofen, naproxen, and derivatives thereof, known analgesics and non-steroidal anti-inflammatory agents. It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds produced by a disclosed a method.

50

Thus, in one aspect, disclosed are cyano compounds having a structure represented by a formula:

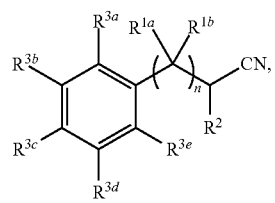

wherein n is selected from 0, 1, 2, 3, and 4; wherein each of $R^{1a}$ and $R^{1b}$, when present, is independently selected from hydrogen and C1-C4 alkyl; wherein $R^2$ is selected from hydrogen and C1-C4 alkyl; and wherein each of $R^{3a}$, $R^{3b}$, $R^{3e}$, $R^{3d}$, and $R^{3e}$ is independently selected from hydrogen, halogen, —OH, —NH$_2$, —NO$_2$, —CN, C1-C4 alkyl, and C1-C4 alkoxy; or wherein any two of $R^{3a}$, $R^{3b}$, $R^{3c}$, $R^{3d}$, and $R^{3e}$ together comprise a structure represented by a formula:

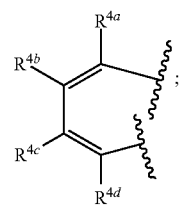

and
wherein each of $R^{4a}$, $R^{4b}$, $R^{4c}$, and $R^{4d}$, when present, is independently selected from hydrogen, halogen, —OH, —NH$_2$, —NO$_2$, —CN, C1-C4 alkyl, and C1-C4 alkoxy, or pharmaceutically acceptable salts thereof.

In a further aspect, the cyano compound has a structure represented by a formula:

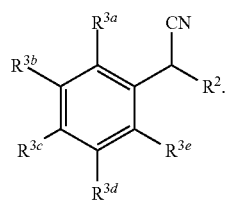

In a still further aspect, the cyano compound has a structure represented by a formula:

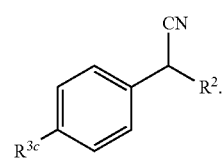

In yet a further aspect, the cyano compound has a structure represented by a formula:

In an even further aspect, the cyano compound has a structure represented by a formula:

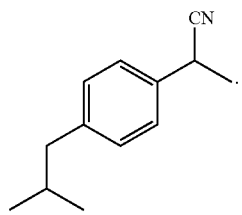

In a still further aspect, the cyano compound has a structure represented by a formula:

In yet a further aspect, the cyano compound has a structure represented by a formula:

In an even further aspect, the cyano compound has a structure represented by a formula:

In a still further aspect, the cyano compound has a structure represented by a formula:

In a further aspect, disclosed are carboxyl compounds having a structure represented by a formula:

or pharmaceutically acceptable salts thereof.

In a still further aspect, the carboxyl compound has a structure represented by a formula:

In yet a further aspect, the carboxyl compound has a structure represented by a formula:

In an even further aspect, the carboxyl compound has a structure represented by a formula:

In a still further aspect, the carboxyl compound has a structure represented by a formula:

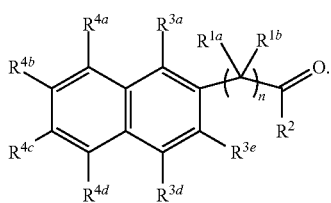

In yet a further aspect, the carboxyl compound has a structure represented by a formula:

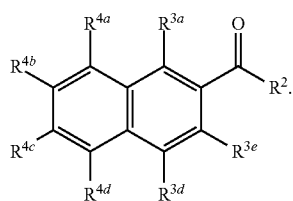

In an even further aspect, the carboxyl compound has a structure represented by a formula:

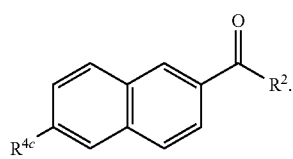

In a still further aspect, the carboxyl compound has a structure represented by a formula:

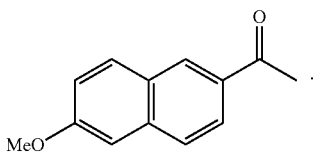

In a further aspect, disclosed are alcohols having a structure represented by a formula:

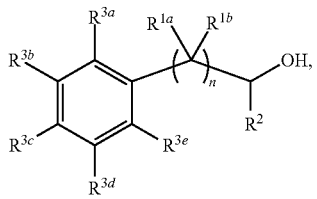

or pharmaceutically acceptable salts thereof.

In a still further aspect, the alcohol has a structure represented by a formula:

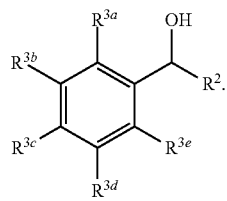

In yet a further aspect, the alcohol has a structure represented by a formula:

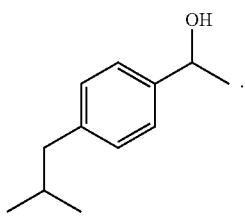

In an even further aspect, the alcohol has a structure represented by a formula:

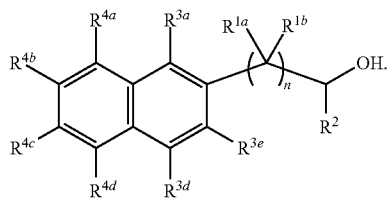

In a still further aspect, the alcohol has a structure represented by a formula:

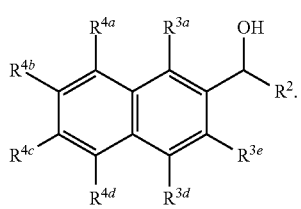

In yet a further aspect, the alcohol has a structure represented by a formula:

In an even further aspect, the alcohol has a structure represented by a formula:

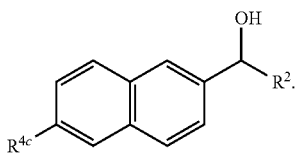

In a still further aspect, the alcohol has a structure represented by a formula:

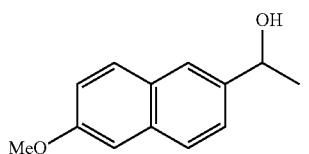

In yet a further aspect, the alcohol has a structure represented by a formula:

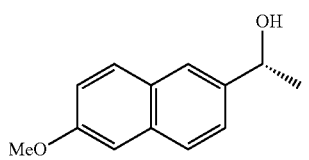

In a further aspect, disclosed are compounds having a structure represented by a formula:

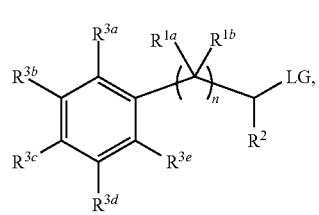

wherein LG is a leaving group, or pharmaceutically acceptable salts thereof.

In a still further aspect, the compound has a structure represented by a formula:

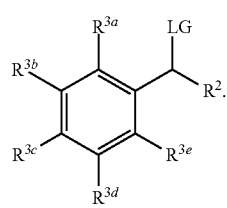

In yet a further aspect, the compound has a structure represented by a formula:

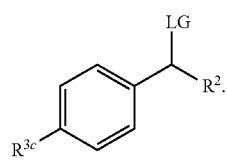

In an even further aspect, the compound has a structure represented by a formula:

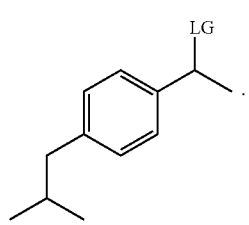

In a still further aspect, the compound has a structure represented by a formula:

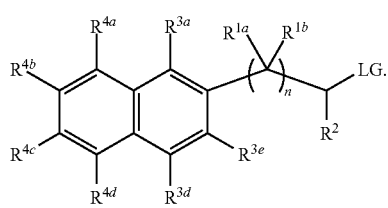

In yet a further aspect, the compound has a structure represented by a formula:

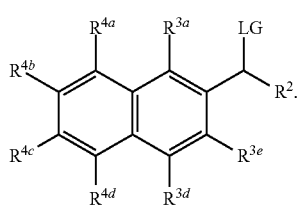

In an even further aspect, the compound has a structure represented by a formula:

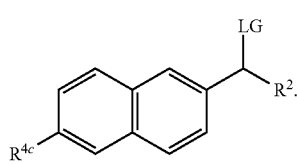

In a still further aspect, the compound has a structure represented by a formula:

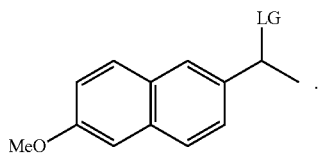

In yet a further aspect, the compound has a structure represented by a formula:

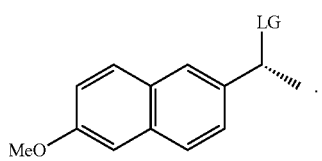

In a further aspect, disclosed are carboxylic acids having a structure represented by a formula:

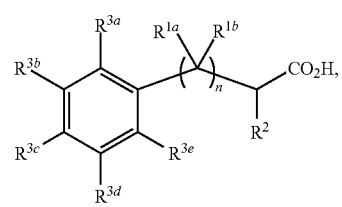

In a still further aspect, the carboxylic has a structure represented by a formula:

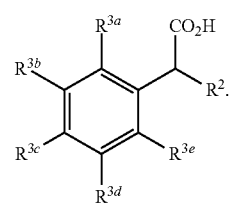

In yet a further aspect, the carboxylic acid has a structure represented by a formula:

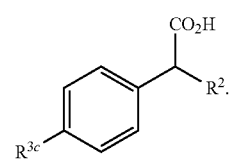

In an even further aspect, the carboxylic acid has a structure represented by a formula:

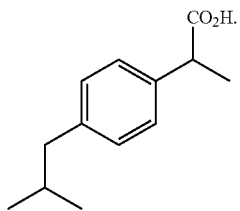

In a still further aspect, the carboxylic acid has a structure represented by a formula:

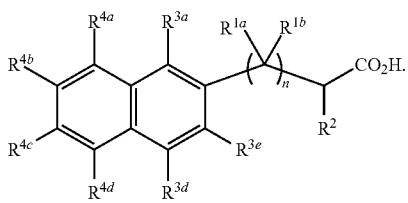

In yet a further aspect, the carboxylic acid has a structure represented by a formula:

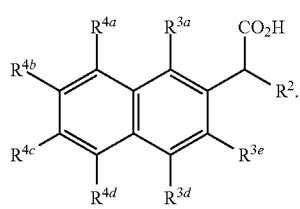

In an even further aspect, the carboxylic acid has a structure represented by a formula:

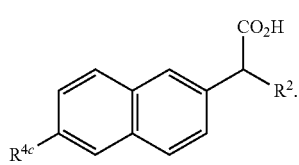

In a still further aspect, the carboxylic acid has a structure represented by a formula:

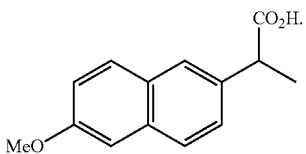

In yet a further aspect, the carboxylic acid has a structure represented by a formula:

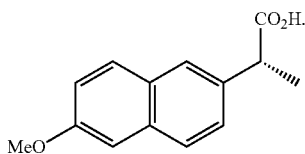

Also disclosed are cyano compounds having a structure:

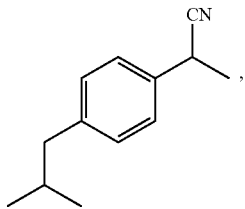

or a pharmaceutically acceptable salt thereof.

In a further aspect, disclosed are carboxyl compounds having a structure:

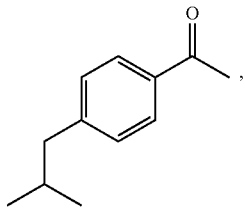

or a pharmaceutically acceptable salt thereof.

In a further aspect, disclosed are alcohols having a structure:

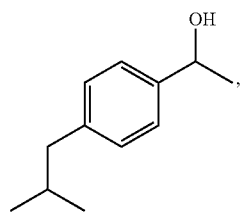

or a pharmaceutically acceptable salt thereof.

In a further aspect, disclosed are compounds having a structure:

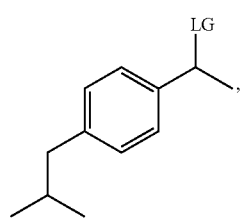

or a pharmaceutically acceptable salt thereof.

In a further aspect, disclosed are carboxylic acids having a structure:

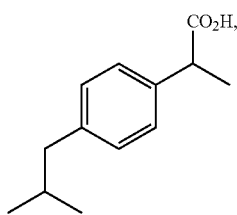

or a pharmaceutically acceptable salt thereof.

Also disclosed are carboxylic acids having a structure represented by a formula:

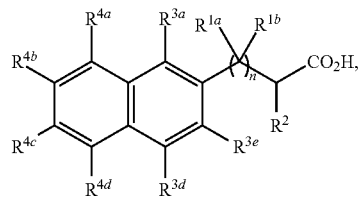

wherein n is selected from 0, 1, 2, 3, and 4; wherein each of $R^{1a}$ and $R^{1b}$, when present, is independently selected from hydrogen and C1-C4 alkyl; wherein $R^2$ is selected from hydrogen and C1-C4 alkyl; and wherein each of $R^{3a}$, $R^{3d}$, and $R^{3e}$ is independently selected from hydrogen, halogen, —OH, —NH$_2$, —NO$_2$, —CN, C1-C4 alkyl, C1-C4 haloalkyl, C1-C4 alkoxy, C1-C4 hydroxy, C1-C4 aminoalkyl, C1-C4 alkylamino, and (C1-C4)(C1-C4) dialkylamino; and wherein each of $R^{4a}$, $R^{4b}$, $R^{4c}$, and $R^{4d}$ is independently selected from hydrogen, halogen, —OH, —NH$_2$, —NO$_2$, —CN, C1-C4 alkyl, C1-C4 haloalkyl, C1-C4 alkoxy, C1-C4 hydroxy, C1-C4 aminoalkyl, C1-C4 alkylamino, and (C1-C4)(C1-C4) dialkylamino, or a pharmaceutically acceptable salt thereof.

In a further aspect, the carboxylic acid has a structure represented by a formula:

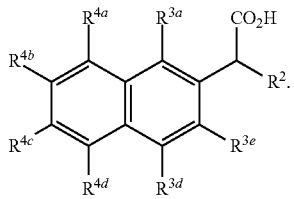

In a still further aspect, the carboxylic acid has a structure represented by a formula:

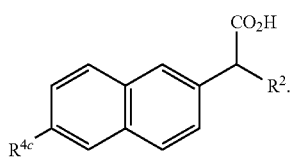

In yet a further aspect, the carboxylic acid has a structure represented by a formula:

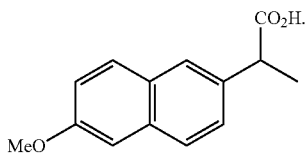

In an even further aspect, the carboxylic acid has a structure represented by a formula:

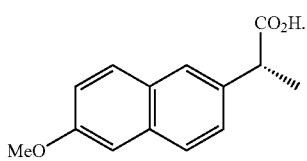

In a further aspect, disclosed are alcohols having a structure represented by a formula:

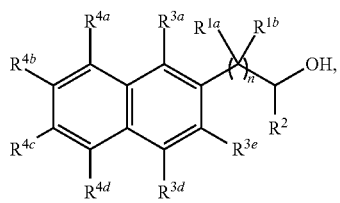

or a pharmaceutically acceptable salt thereof.

In a still further aspect, the alcohol has a structure represented by a formula:

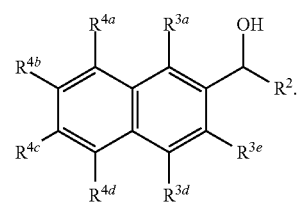

In yet a further aspect, the alcohol has a structure represented by a formula:

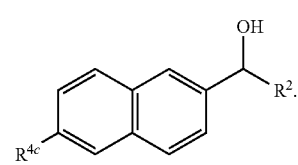

In an even further aspect, the alcohol has a structure represented by a formula:

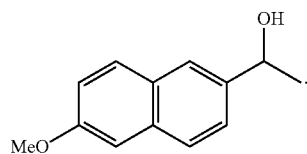

In a still further aspect, the alcohol has a structure represented by a formula:

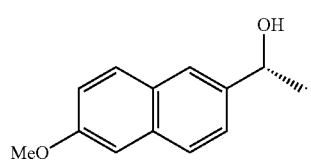

In a further aspect, disclosed are compounds having a structure represented by a formula:

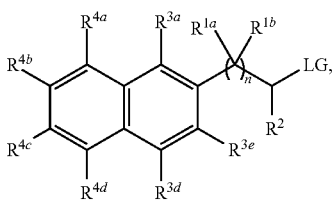

or a pharmaceutically acceptable salt thereof.

In a still further aspect, the compound has a structure represented by a formula:

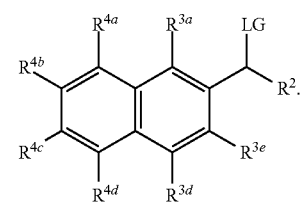

In yet a further aspect, the compound has a structure represented by a formula:

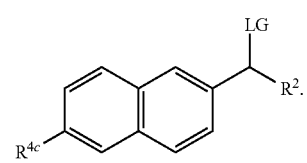

In an even further aspect, the compound has a structure represented by a formula:

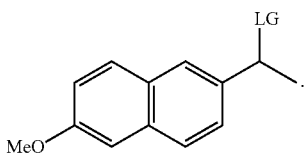

In a still further aspect, the compound has a structure represented by a formula:

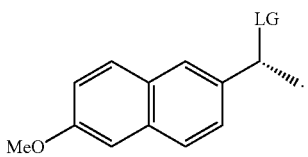

In a further aspect, disclosed are cyano compounds having a structure represented by a formula:

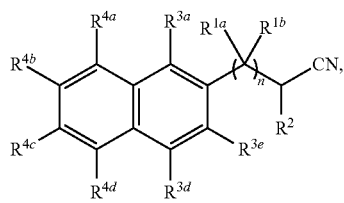

or a pharmaceutically acceptable salt thereof.

In a still further aspect, the cyano compound has a structure represented by a formula:

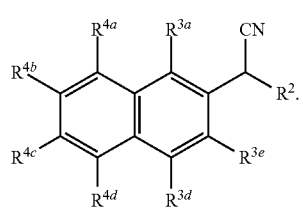

In yet a further aspect, the cyano compound has a structure represented by a formula:

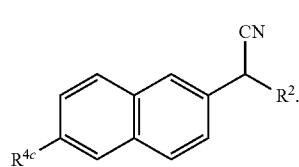

In an even further aspect, the cyano compound has a structure represented by a formula:

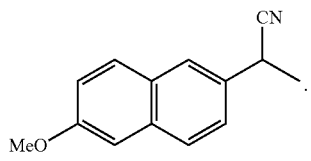

In a still further aspect, the cyano compound has a structure represented by a formula:

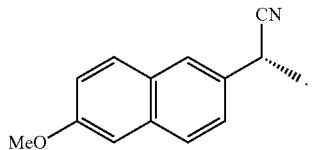

In a further aspect, n is selected from 0, 1, 2, 3, and 4. In a still further aspect, n is selected from 0, 1, 2, and 3. In yet a further aspect, n is selected from 0, 1, and 2. In an even further aspect, n is selected from 0 and 1. In a still further aspect, n is 4. In yet a further aspect, n is 3. In an even further aspect, n is 2. In a still further aspect, n is 1. In yet a further aspect, n is 0.

a. $R^{1a}$ and $R^{1b}$ Groups

In one aspect, each of $R^{1a}$ and $R^{1b}$, when present, is independently selected from hydrogen and C1-C4 alkyl. In a further aspect, each of $R^{1a}$ and $R^{1b}$, when present, is independently selected from hydrogen, methyl, ethyl, n-propyl, and isopropyl. In a still further aspect, each of $R^{1a}$ and $R^{1b}$, when present, is independently selected from hydrogen, methyl, and ethyl. In yet a further aspect, each of $R^{1a}$ and $R^{1b}$, when present, is independently selected from hydrogen and ethyl. In an even further aspect, each of $R^{1a}$ and $R^{1b}$, when present, is independently selected from hydrogen and methyl.

In a further aspect, each of $R^{1a}$ and $R^{1b}$, when present, is hydrogen.

In a further aspect, each of $R^{1a}$ and $R^{1b}$, when present, is independently selected from methyl, ethyl, n-propyl, isopropyl, n-butyl, isobutyl, sec-butyl, and tert-butyl. In a still further aspect, each of $R^{1a}$ and $R^{1b}$, when present, is independently selected from methyl, ethyl, n-propyl, and isopropyl. In yet a further aspect, each of $R^{1a}$ and $R^{1b}$, when present, is independently selected from methyl and ethyl. In an even further aspect, each of $R^{1a}$ and $R^{1b}$, when present, is ethyl. In a still further aspect, each of $R^{1a}$ and $R^{1b}$, when present, is methyl.

In a further aspect, $R^{1a}$ is hydrogen and $R^{1b}$ is selected from hydrogen and C1-C4 alkyl. In a still further aspect, $R^{1a}$ is hydrogen and $R^{1b}$ is selected from hydrogen, methyl, ethyl, n-propyl, and isopropyl. In yet a further aspect, $R^{1a}$ is hydrogen and $R^{1b}$ is selected from hydrogen, methyl, and ethyl. In an even further aspect, $R^{1a}$ is hydrogen and $R^{1b}$ is selected from hydrogen and ethyl. In a still further aspect, $R^{1a}$ is hydrogen and $R^{1b}$ is selected from hydrogen and methyl.

In a further aspect, $R^{1b}$ is hydrogen and $R^{1a}$ is selected from hydrogen and C1-C4 alkyl. In a still further aspect, $R^{1b}$ is hydrogen and $R^{1a}$ is selected from hydrogen, methyl, ethyl, n-propyl, and isopropyl. In yet a further aspect, $R^{1b}$ is hydrogen and $R^{1a}$ is selected from hydrogen, methyl, and ethyl. In an even further aspect, $R^{1b}$ is hydrogen and $R^{1a}$ is selected from hydrogen and ethyl. In a still further aspect, $R^{1b}$ is hydrogen and $R^{1a}$ is selected from hydrogen and methyl.

b. $R^2$ Groups

In one aspect, $R^2$ is selected from hydrogen and C1-C4 alkyl. In a further aspect, $R^2$ is selected from hydrogen, methyl, ethyl, isopropyl, and n-propyl. In a still further aspect, $R^2$ is selected from hydrogen, methyl, and ethyl. In yet a further aspect, $R^2$ is selected from hydrogen and methyl. In a still further aspect, $R^2$ is selected from hydrogen and ethyl. In yet a further aspect, $R^2$ is hydrogen.

In a further aspect, $R^2$ is selected from methyl, ethyl, n-propyl, isopropyl, n-butyl, isobutyl, sec-butyl, and tert-butyl. In a still further aspect, $R^2$ is selected from methyl, ethyl, n-propyl, and isopropyl. In yet a further aspect, $R^2$ is selected from methyl and ethyl. In an even further aspect, $R^2$ is ethyl. In a still further aspect, $R^2$ is methyl.

c. $R^{3A}$, $R^{3B}$, $R^{3C}$, $R^{3D}$, and $R^{3E}$ Groups

In one aspect, each of $R^{3a}$, $R^{3b}$, $R^{3c}$, $R^{3d}$, and $R^{3e}$ is independently selected from hydrogen, halogen, —OH, —NH$_2$, —NO$_2$, —CN, C1-C4 alkyl, and C1-C4 alkoxy; or any two of $R^{3a}$, $R^{3b}$, $R^{3c}$, $R^{3d}$, and $R^{3e}$ together comprise a structure represented by a formula:

In a further aspect, each of $R^{3a}$, $R^{3b}$, $R^{3c}$, $R^{3d}$, and $R^{3e}$ is independently selected from hydrogen, halogen, —OH, —NH$_2$, —NO$_2$, —CN, C1-C4 alkyl, and C1-C4 alkoxy. In a still further aspect, each of $R^{3a}$, $R^{3b}$, $R^{3c}$, $R^{3d}$, and $R^{3e}$ is independently selected from hydrogen, —F, —Cl, —OH, —NH$_2$, —NO$_2$, —CN, methyl, ethyl, n-propyl, isopropyl, —OCH$_3$, —OCH$_2$CH$_3$, —OCH(CH$_3$)$_2$, and —OCH$_2$CH$_2$CH$_3$. In yet a further aspect, each of $R^{3a}$, $R^{3b}$, $R^{3c}$, $R^{3d}$, and $R^{3e}$ is independently selected from hydrogen, —F, —Cl, —OH, —NH$_2$, —NO$_2$, —CN, methyl, ethyl, —OCH$_3$, and —OCH$_2$CH$_3$. In an even further aspect, each of $R^{3a}$, $R^{3b}$, $R^{3c}$, $R^{3d}$, and $R^{3e}$ is independently selected from hydrogen, —F, —Cl, —OH, —NH$_2$, —NO$_2$, —CN, methyl, and —OCH$_{32}$.

In a further aspect, each of $R^{3a}$, $R^{3b}$, $R^{3c}$, $R^{3d}$, and $R^{3e}$ is independently selected from hydrogen, halogen, —OH, —CN, C1-C4 alkyl, and C1-C4 alkoxy. In a still further aspect, each of $R^{3a}$, $R^{3b}$, $R^{3c}$, $R^{3d}$, and $R^{3e}$ is independently selected from hydrogen, —F, —Cl, —OH, —CN, methyl, ethyl, n-propyl, isopropyl, —OCH$_3$, —OCH$_2$CH$_3$, —OCH(CH$_3$)$_2$, and —OCH$_2$CH$_2$CH$_3$. In yet a further aspect, each of $R^{3a}$, $R^{3b}$, $R^{3c}$, $R^{3d}$, and $R^{3e}$ is independently selected from hydrogen, —F, —Cl, —OH, —CN, methyl, ethyl, —OCH$_3$, and —OCH$_2$CH$_3$. In an even further aspect, each of $R^{3a}$, $R^{3b}$, $R^{3c}$, $R^{3d}$, and $R^{3e}$ is independently selected from hydrogen, —F, —Cl, —OH, —CN, methyl, and —OCH$_3$.

In a further aspect, each of $R^{3a}$, $R^{3b}$, $R^{3d}$, and $R^{3e}$ is hydrogen.

In a further aspect, each of $R^{3a}$, $R^{3b}$, $R^{3d}$, and $R^{3e}$ is hydrogen and $R^{3c}$ is selected from halogen, —OH, —NH$_2$, —NO$_2$, —CN, C1-C4 alkyl, and C1-C4 alkoxy. In a still further aspect, each of $R^{3a}$, $R^{3b}$, $R^{3d}$, and $R^{3e}$ is hydrogen and $R^{3c}$ is selected from —F, —Cl, —OH, —NH$_2$, —NO$_2$, —CN, methyl, ethyl, n-propyl, isopropyl, —OCH$_3$, —OCH$_2$CH$_3$, —OCH(CH$_3$)$_2$, and —OCH$_2$CH$_2$CH$_3$. In yet a further aspect, each of $R^{3a}$, $R^{3b}$, $R^{3d}$, and $R^{3e}$ is hydrogen and $R^{3c}$ is selected from —F, —Cl, —OH, —NH$_2$, —NO$_2$, —CN, methyl, ethyl, —OCH$_3$, and —OCH$_2$CH$_3$. In an even further aspect, each of $R^{3a}$, $R^{3b}$, $R^{3d}$, and $R^{3e}$ is hydrogen and $R^{3c}$ is selected from —F, —Cl, —OH, —NH$_2$, —NO$_2$, —CN, methyl, and —OCH$_3$.

In a further aspect, each of $R^{3a}$, $R^{3b}$, $R^{3d}$, and $R^{3e}$ is hydrogen and $R^{3c}$ is selected from halogen, —OH, —CN, C1-C4 alkyl, and C1-C4 alkoxy. In a still further aspect, each of $R^{3a}$, $R^{3b}$, $R^{3d}$, and $R^{3e}$ is hydrogen and $R^{3c}$ is selected from —F, —Cl, —OH, —CN, methyl, ethyl, n-propyl, isopropyl, —OCH$_3$, —OCH$_2$CH$_3$, —OCH(CH$_3$)$_2$, and —OCH$_2$CH$_2$CH$_3$. In yet a further aspect, each of $R^{3a}$, $R^{3b}$, $R^{3d}$, and $R^{3e}$ is hydrogen and $R^{3c}$ is selected from —F, —Cl, —OH, —CN, methyl, ethyl, —OCH$_3$, and —OCH$_2$CH$_3$. In an even further aspect, each of $R^{3a}$, $R^{3b}$, $R^{3d}$, and $R^{3e}$ is hydrogen and $R^{3c}$ is selected from —F, —Cl, —OH, —CN, methyl, and —OCH$_3$.

In a further aspect, $R^{3c}$ is selected from halogen, —OH, —NH$_2$, —NO$_2$, —CN, C1-C4 alkyl, and C1-C4 alkoxy. In a still further aspect, $R^{3c}$ is selected from —F, —Cl, —OH, —NH$_2$, —NO$_2$, —CN, methyl, ethyl, n-propyl, isopropyl, —OCH$_3$, —OCH$_2$CH$_3$, —OCH(CH$_3$)$_2$, and —OCH$_2$CH$_2$CH$_3$. In yet a further aspect, $R^{3c}$ is selected from —F, —Cl, —OH, —NH$_2$, —NO$_2$, —CN, methyl, ethyl, —OCH$_3$, and —OCH$_2$CH$_3$. In an even further aspect, $R^{3c}$ is selected from —F, —Cl, —OH, —NH$_2$, —NO$_2$, —CN, methyl, and —OCH$_3$.

In a further aspect, $R^{3c}$ is selected from halogen, —OH, —CN, C1-C4 alkyl, and C1-C4 alkoxy. In a still further aspect, $R^{3c}$ is selected from —F, —Cl, —OH, —CN, methyl, ethyl, n-propyl, isopropyl, —OCH$_3$, —OCH$_2$CH$_3$, —OCH(CH$_3$)$_2$, and —OCH$_2$CH$_2$CH$_3$. In yet a further aspect, $R^{3c}$ is selected from —F, —Cl, —OH, —CN, methyl, ethyl, —OCH$_3$, and —OCH$_2$CH$_3$. In an even further aspect, $R^{3c}$ is selected from —F, —Cl, —OH, —CN, methyl, and —OCH$_3$.

In a further aspect, $R^{3c}$ is C1-C4 alkyl. In yet a further aspect, $R^{3c}$ is selected from methyl, ethyl, n-propyl, isopropyl, n-butyl, isobutyl, sec-butyl, and tert-butyl. In an even further aspect, $R^{3c}$ is selected from methyl, ethyl, n-propyl, and isopropyl. In a still further aspect, $R^{3c}$ is selected from methyl and ethyl. In yet a further aspect, $R^{3c}$ is selected from n-propyl and isopropyl. In an even further aspect, $R^{3c}$ is n-propyl. In a still further aspect, $R^{3c}$ is isopropyl. In yet a further aspect, $R^{3c}$ is ethyl. In an even further aspect, $R^{3c}$ is methyl.

In a further aspect, $R^{3c}$ is selected from n-butyl, isobutyl, sec-butyl, and tert-butyl. In a still further aspect, $R^{3c}$ is selected from n-butyl, isobutyl, and sec-butyl. In yet a further aspect, $R^{3c}$ is selected from isobutyl, sec-butyl, and tert-butyl. In an even further aspect, $R^{3c}$ is n-butyl, isobutyl, and tert-butyl. In a still further aspect, $R^{3c}$ is selected from n-butyl and isobutyl. In yet a further aspect, $R^{3c}$ is selected from isobutyl and sec-butyl. In an even further aspect, $R^{3c}$ is selected from isobutyl and tert-butyl. In a still further aspect, $R^{3c}$ is n-butyl. In yet a further aspect, $R^{3c}$ is sec-butyl. In an even further aspect, $R^{3c}$ is tert-butyl. In a still further aspect, $R^{3c}$ is isobutyl.

In a further aspect, any two of $R^{3a}$, $R^{3b}$, $R^{3c}$, $R^{3d}$, and $R^{3e}$ together comprise a structure represented by a formula:

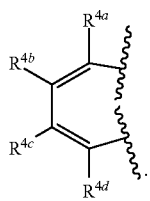

In a further aspect, $R^{3a}$ and $R^{3b}$ together comprise a structure represented by a formula:

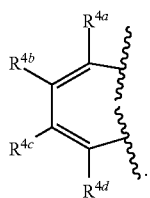

In a further aspect, $R^{3b}$ and $R^{3c}$ together comprise a structure represented by a formula:

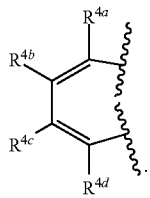

In a further aspect, $R^{3c}$ and $R^{3d}$ together comprise a structure represented by a formula:

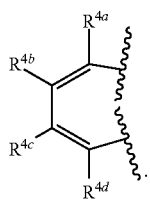

In a further aspect, $R^{3d}$ and $R^{3e}$ together comprise a structure represented by a formula:

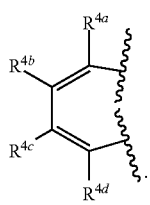

In a further aspect, $R^{3b}$ and $R^{3c}$ together comprise a structure represented by a formula:

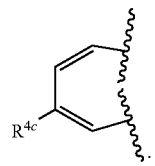

d. $R^{4A}$, $R^{4B}$, $R^{4C}$, and $R^{4D}$ Groups

In one aspect, each of $R^{4a}$, $R^{4b}$, $R^{4c}$, and $R^{4d}$, when present, is independently selected from hydrogen, halogen, —OH, —NH$_2$, —NO$_2$, —CN, C1-C4 alkyl, and C1-C4 alkoxy. In a further aspect, each of $R^{4a}$, $R^{4b}$, $R^{4c}$, and $R^{4d}$ is independently selected from hydrogen, —F, —Cl, —OH, —NH$_2$, —NO$_2$, —CN, methyl, ethyl, n-propyl, isopropyl, —OCH$_3$, —OCH$_2$CH$_3$, —OCH(CH$_3$)$_2$, and —OCH$_2$CH$_2$CH$_3$. In a still further aspect, each of $R^{4a}$, $R^{4b}$, $R^{4c}$, and $R^{4d}$ is independently selected from hydrogen, —F, —Cl, —OH, —NH$_2$, —NO$_2$, —CN, methyl, ethyl, —OCH$_3$, and —OCH$_2$CH$_3$. In yet a further aspect, each of $R^{4a}$, $R^{4b}$, $R^{4c}$, and $R^{4d}$ is independently selected from hydrogen, —F, —Cl, —OH, —NH$_2$, —NO$_2$, —CN, methyl, and —OCH$_3$.

In a further aspect, each of $R^{4a}$, $R^{4b}$, $R^{4c}$, and $R^{4d}$ is independently selected from hydrogen, halogen, —OH, —CN, C1-C4 alkyl, and C1-C4 alkoxy. In a still further aspect, each of $R^{4a}$, $R^{4b}$, $R^{4c}$, and $R^{4d}$ is independently selected from hydrogen, —F, —Cl, —OH, —CN, methyl, ethyl, n-propyl, isopropyl, —OCH$_3$, —OCH$_2$CH$_3$, —OCH(CH$_3$)$_2$, and —OCH$_2$CH$_2$CH$_3$. In yet a further aspect, each of $R^{4a}$, $R^{4b}$, $R^{4c}$, and $R^{4d}$ is independently selected from hydrogen, —F, —Cl, —OH, —CN, methyl, ethyl, —OCH$_3$, and —OCH$_2$CH$_3$. In an even further aspect, each of $R^{4a}$, $R^{4b}$, $R^{4c}$, and $R^{4d}$ is independently selected from hydrogen, —F, —Cl, —OH, —CN, methyl, and —OCH$_3$.

In a further aspect, each of $R^{4a}$, $R^{4b}$, and $R^{4d}$ is hydrogen.

In a further aspect, each of $R^{4a}$, $R^{4b}$, and $R^{4d}$ is hydrogen and $R^{4c}$ is selected from halogen, —OH, —NH$_2$, —NO$_2$, —CN, C1-C4 alkyl, and C1-C4 alkoxy. In a still further aspect, each of $R^{4a}$, $R^{4b}$, and $R^{4d}$ is hydrogen and $R^{4c}$ is selected from —F, —Cl, —OH, —NH$_2$, —NO$_2$, —CN, methyl, ethyl, n-propyl, isopropyl, —OCH$_3$, —OCH$_2$CH$_3$, —OCH(CH$_3$)$_2$, and —OCH$_2$CH$_2$CH$_3$. In yet a further aspect, each of $R^{4a}$, $R^{4b}$, and $R^{4d}$ is hydrogen and $R^{4c}$ is selected from —F, —Cl, —OH, —NH$_2$, —NO$_2$, —CN, methyl, ethyl, —OCH$_3$, and —OCH$_2$CH$_3$. In an even further aspect, each of $R^{4a}$, $R^{4b}$, and $R^{4d}$ is hydrogen and $R^{4c}$ is selected from —F, —Cl, —OH, —NH$_2$, —NO$_2$, —CN, methyl, and —OCH$_3$.

In a further aspect, each of $R^{4a}$, $R^{4b}$, and $R^{4d}$ is hydrogen and $R^{4c}$ is selected from halogen, —OH, —CN, C1-C4 alkyl, and C1-C4 alkoxy. In a still further aspect, each of $R^{4a}$, $R^{4b}$, and $R^{4d}$ is hydrogen and $R^{4c}$ is selected from —F, —Cl, —OH, —CN, methyl, ethyl, n-propyl, isopropyl, —OCH$_3$, —OCH$_2$CH$_3$, —OCH(CH$_3$)$_2$, and —OCH$_2$CH$_2$CH$_3$. In yet a further aspect, each of $R^{4a}$, $R^{4b}$, and $R^{4d}$ is hydrogen and $R^{4c}$ is selected from —F, —Cl, —OH, —CN, methyl, ethyl, —OCH$_3$, and —OCH$_2$CH$_3$. In an even further aspect, each of $R^{4a}$, $R^{4b}$, and $R^{4d}$ is hydrogen and $R^{4c}$ is selected from —F, —Cl, —OH, —CN, methyl, and —OCH$_3$.

In a further aspect, $R^{4c}$ is selected from halogen, —OH, —NH$_2$, —NO$_2$, —CN, C1-C4 alkyl, and C1-C4 alkoxy. In a still further aspect, $R^{4c}$ is selected from —F, —Cl, —OH, —NH$_2$, —NO$_2$, —CN, methyl, ethyl, n-propyl, isopropyl, —OCH$_3$, —OCH$_2$CH$_3$, —OCH(CH$_3$)$_2$, and —OCH$_2$CH$_2$CH$_3$. In yet a further aspect, R$^{4c}$ is selected from —F, —Cl, —OH, —NH$_2$, —NO$_2$, —CN, methyl, ethyl, —OCH$_3$, and —OCH$_2$CH$_3$. In an even further aspect, R$^{4c}$ is selected from —F, —Cl, —OH, —NH$_2$, —NO$_2$, —CN, methyl, and —OCH$_3$.

In a further aspect, R$^{4c}$ is selected from halogen, —OH, —CN, C1-C4 alkyl, and C1-C4 alkoxy. In a still further aspect, R$^{4c}$ is selected from —F, —Cl, —OH, —CN, methyl, ethyl, n-propyl, isopropyl, —OCH$_3$, —OCH$_2$CH$_3$, —OCH(CH$_3$)$_2$, and —OCH$_2$CH$_2$CH$_3$. In yet a further aspect, R$^{4c}$ is selected from —F, —Cl, —OH, —CN, methyl, ethyl, —OCH$_3$, and —OCH$_2$CH$_3$. In an even further aspect, R$^{4c}$ is selected from —F, —Cl, —OH, —CN, methyl, and —OCH$_3$.

In a further aspect, R$^{4c}$ is C1-C4 alkoxy. In yet a further aspect, R$^{4c}$ is selected from —OCH$_3$, —OCH$_2$CH$_3$, —OCH(CH$_3$)$_2$, and —OCH$_2$CH$_2$CH$_3$. In an even further aspect, Roc is selected from —OCH$_3$ and —OCH$_2$CH$_3$. In a still further aspect, R$^{1c}$ is selected from —OCH(CH$_3$)$_2$ and —OCH$_2$CH$_2$CH$_3$. In yet a further aspect, R$^{4c}$ is —OCH$_2$CH$_2$CH$_3$. In an even further aspect, R$^{4c}$ is —OCH(CH$_3$)$_2$. In a still further aspect, R$^{4c}$ is —OCH$_2$CH$_3$. In yet a further aspect, R$^{4c}$ is —OCH$_3$.

2. Example Compounds

In one aspect, a compound can be present as one or more of the following structures:

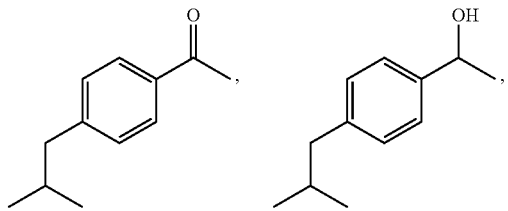

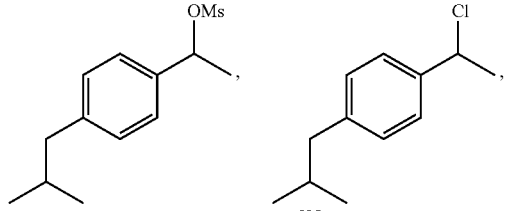

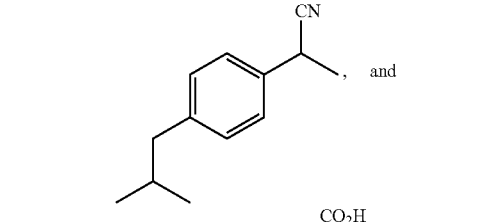, and

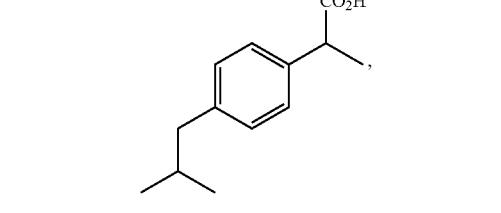

or a pharmaceutically acceptable salt thereof.

In one aspect, a compound can be present as the following structure:

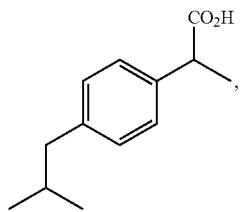

or a pharmaceutically acceptable salt thereof.

3. Prophetic Examples

The following compound examples are prophetic, and can be prepared using the synthesis methods described herein above and other general methods as needed as would be known to one skilled in the art. Thus, in one aspect, a compound can be selected from:

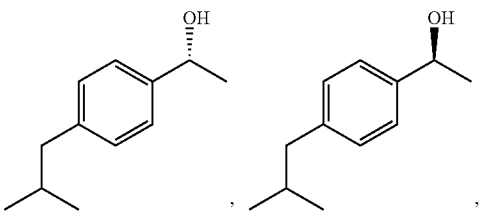

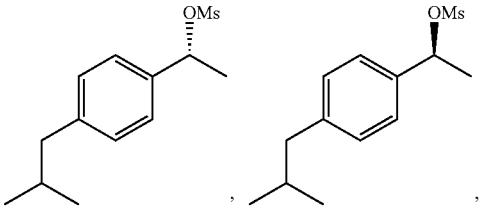

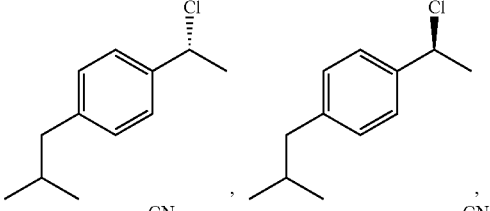

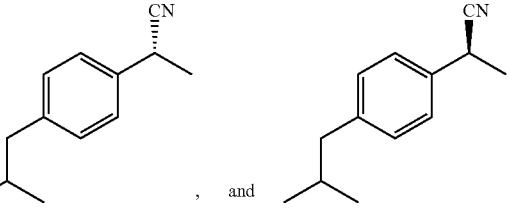, and

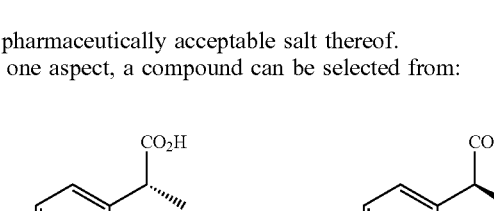

or a pharmaceutically acceptable salt thereof.

In one aspect, a compound can be selected from:

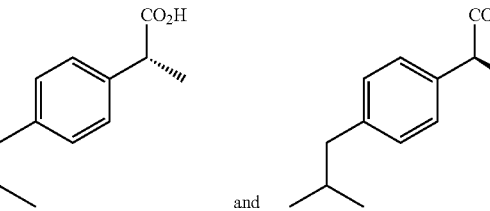

or a pharmaceutically acceptable salt thereof.

In one aspect, a compound can be selected from:

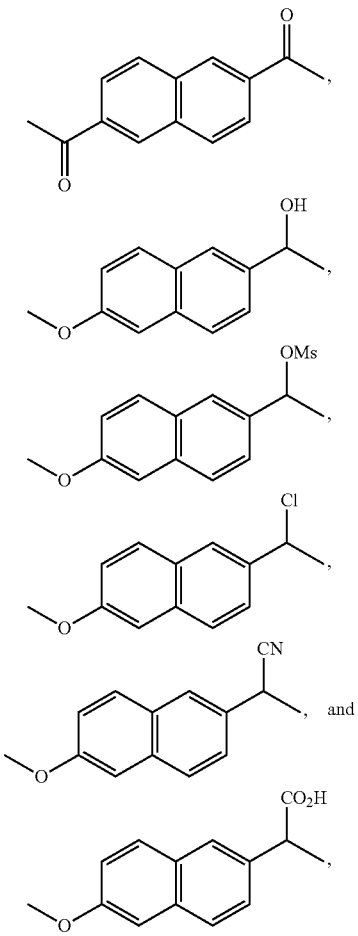

or a pharmaceutically acceptable salt thereof.
In one aspect, a compound is:

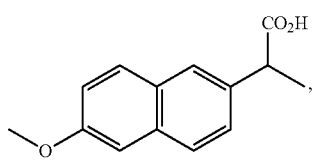 [SMILES: COc1ccc2cc(C(C)C(=O)O)ccc2c1]

or a pharmaceutically acceptable salt thereof.
In one aspect, a compound can be selected from:

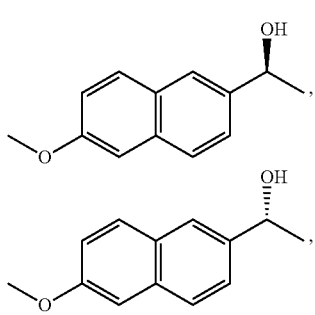

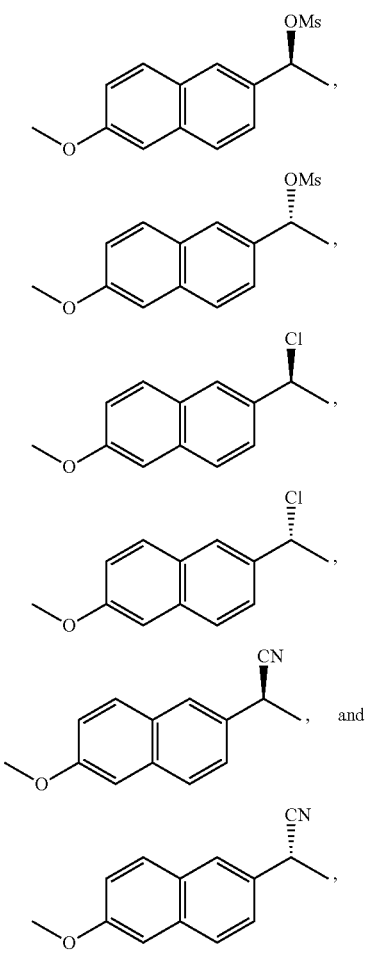

or a pharmaceutically acceptable salt thereof.
In one aspect, a compound can be selected from:

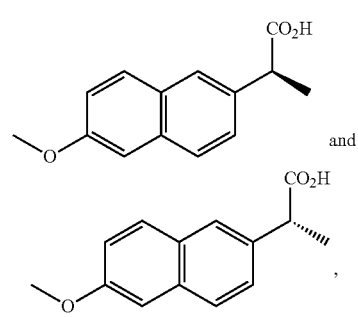

or a pharmaceutically acceptable salt thereof.
In one aspect, a compound can be selected from:

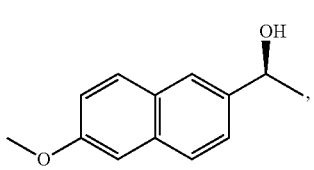

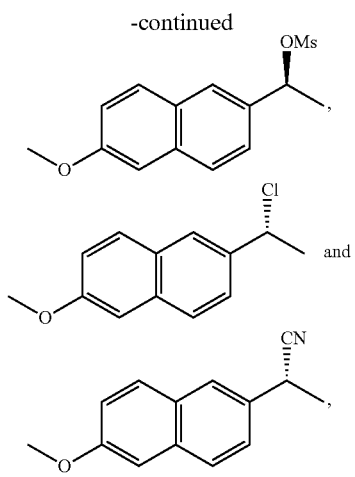

or a pharmaceutically acceptable salt thereof.

In one aspect, a compound is:

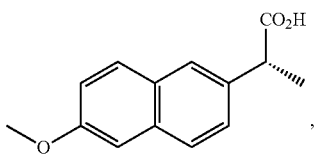 [SMILES: COc1ccc2cc([C@@H](C)C(=O)O)ccc2c1]

or a pharmaceutically acceptable salt thereof.

F. Pharmaceutical Compositions and Formulations

When employed as pharmaceuticals, the compounds provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including, for example, transdermal, epidermal, ophthalmic and to mucous membranes including, for example, intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial (e.g., intrathecal or intraventricular, administration). Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, and powders. Conventional pharmaceutical carriers, aqueous, powder or oily bases, thickeners, and the like may be necessary or desirable.

Also provided are pharmaceutical compositions that contain, as the active ingredient, a compound provided herein or a pharmaceutically acceptable salt thereof, in combination with one or more pharmaceutically acceptable carriers (excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

G. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Initial Efforts Towards the Development of a New Route to Ibuprofen

At least two strategies are known for the manufacture of ibuprofen. The Boots process is six steps with several inefficient, high waste steps. The BASF process, while three steps, uses a heavy and expensive catalyst. Here, a new synthetic route to ibuprofen is described (FIG. 1).

Figure 2:
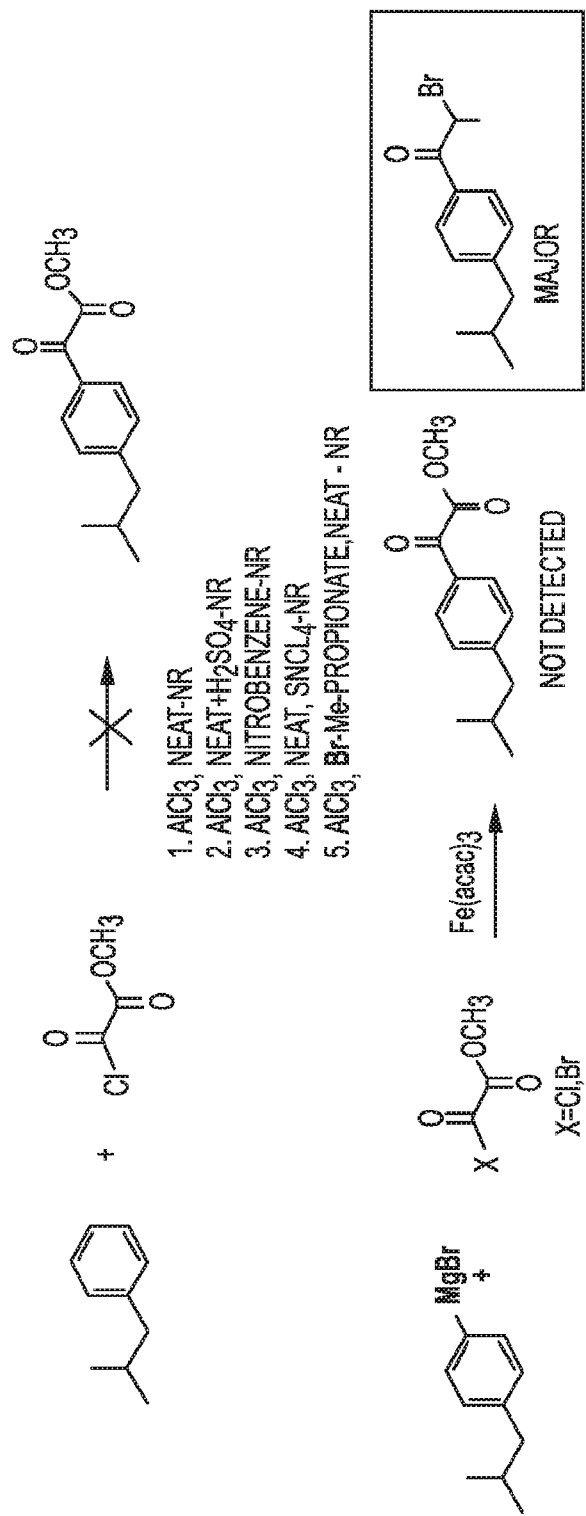
FIG. 2 shows a representative attempt to synthesize a methyl propionate derivative as an ibuprofen precursor.

A methyl propionate route to ibuprofen was initially attempted as shown in FIG. 2. One last attempt using a methyl propionate derivative yielded only a 1:1 mixture of starting materials (Scheme 10).

SCHEME 10.

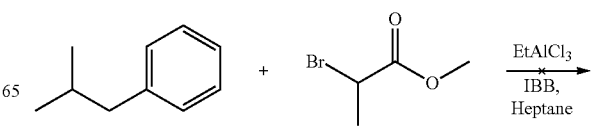

-continued

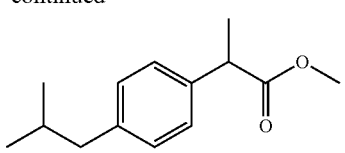

In view of these results, an alternative route via acetophenone was proposed (Table 1).

TABLE 1

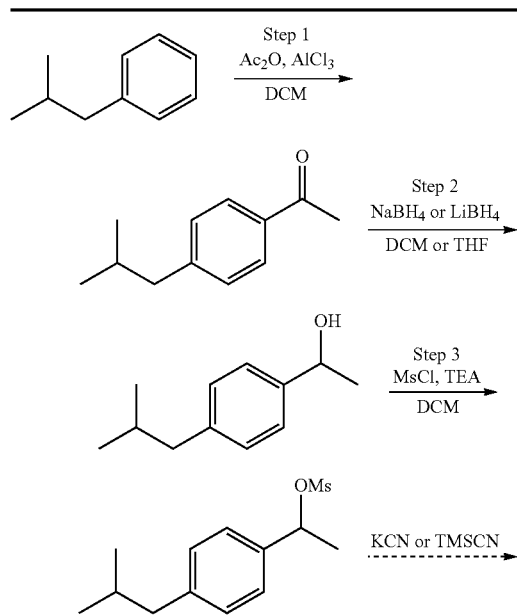

| Step | Exp. | Conditions | Result |
|---|---|---|---|
| 1 | 27 | Ac$_2$O, AlCl$_3$ (2.2 eq), 0° C., 1 h | 98% conversion, 99% result |
| 2 | 28A.1 | NaBH$_4$ (2.2. eq), DCM, rt, 1 h | No reaction |
| 2 | 28A.2 | NaBH$_4$ (2.2. eq), DCM, MeOH, rt, 1 h | 76% conversion |
| 2 | 28B | NaBH$_4$ (2.2. eq), EtOH, rt, 1 h | 95% conversion |
| 2 | 31A | LiBH$_4$ (3.0M THF, 2.2. eq), THF, rt, 1 h | 98% conversion |
| 2 | 31B | LiBH$_4$ (3.0M THF, 2.2. eq), DCM, rt, 1 h | 94% conversion |
| 3 | 30A | TEA (1.4 eq), MsCl (1.2 eq), THF, rt, 1 h | No reaction |
| 3 | 30B.1 | TEA (1.4 eq), MsCl (1.2 eq), THF, rt, 3 h | No reaction (new bottle of MsCl) |
| 3 | 30B.2 | TEA (1.4 eq), MsCl (1.2 eq), THF, rt, overnight | No reaction |
| 3 | 32 | TEA (1.4 eq), MsCl (1.2 eq), DCM, rt, 1 h | 85% pending work-up |

Figure 3:
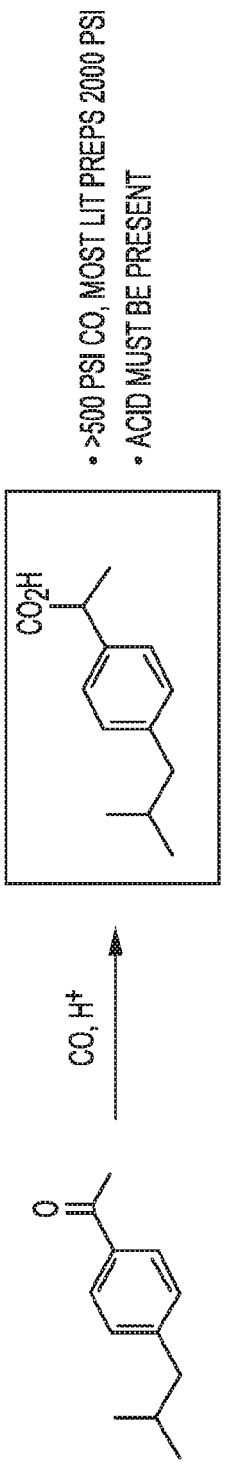
FIG. 3 shows a representative synthetic route to ibuprofen via carbonyl insertion.

Additional strategies investigated are detailed in FIG. 3 and Table 2.

TABLE 2

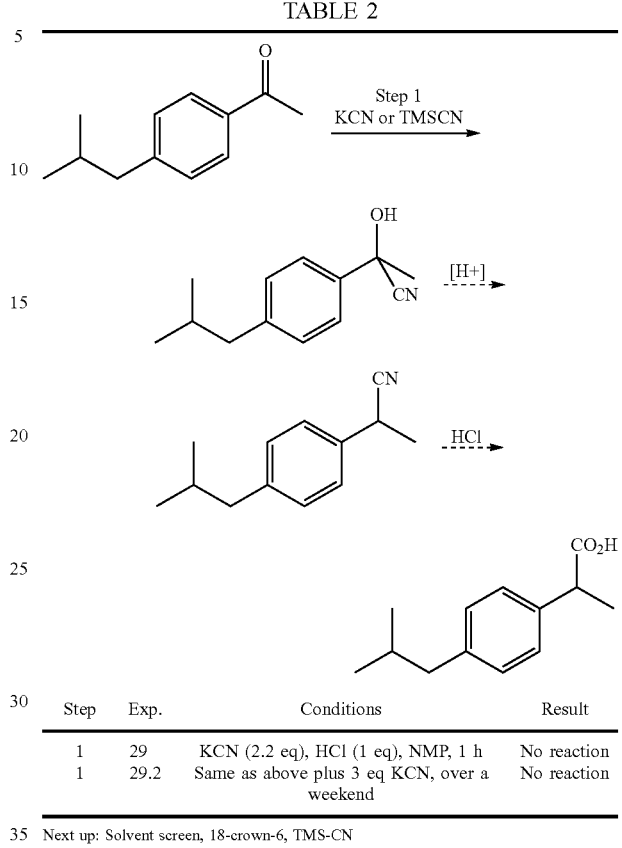

| Step | Exp. | Conditions | Result |
|---|---|---|---|
| 1 | 29 | KCN (2.2 eq), HCl (1 eq), NMP, 1 h | No reaction |
| 1 | 29.2 | Same as above plus 3 eq KCN, over a weekend | No reaction |

Next up: Solvent screen, 18-crown-6, TMS-CN

As shown in Table 3, it was also explored whether the cyanide could be accessed directly from the chloride.

TABLE 3

| Exp. | Stoich. | Solvent | Carrier | Conditions | Result |
|---|---|---|---|---|---|
| JK-44.1 | 1:3 | IPA/H$_2$O | IPA | 10 min., 120° C. | 43% (HPLC) |
| JK-44.2 | 1:3 | IPA/H$_2$O | IPA | 10 min., 160° C. | 53% (HPLC) |
| JK-44.3 | 1:3 | IPA/H$_2$O | IPA | 10 min., 200° C. | Over-pressure, not detected |
| JK-44.4 | 1:6 | IPA/H$_2$O | IPA | 10 min., 120° C. | 64% (HPLC) |
| JK-44.5 | 1:6 | IPA/H$_2$O | IPA | 10 min., 160° C. | 69% (HPLC) |
| JK-44.6 | No CN | IPA | IPA | 10 min., 160° C. | No reaction |
| JK-46.1 | 1:3 | EtOH/H$_2$O | EtOH | 10 min., 120° C. | 30% (HPLC) |

TABLE 3-continued

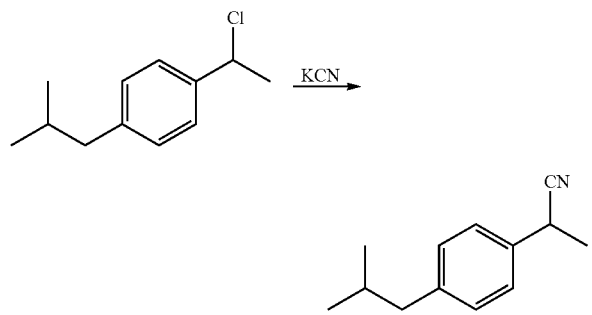

| Exp. | Stoich. | Solvent | Carrier | Conditions | Result |
|---|---|---|---|---|---|
| JK-46.2 | 1:3 | EtOH/H$_2$O | EtOH | 10 min., 160° C. | 34% (HPLC) |
| JK-46.3 | 1:3 | EtOH/H$_2$O | EtOH | 10 min., 200° C. | 32% (HPLC) |
| JK-46.4 | 1:6 | EtOH/H$_2$O | IPA | 20 min., 160° C. | 32% (HPLC) |
| JK-46.5 | 1:6 | EtOH/H$_2$O | IPA | 20 min., 200° C. | 25% + 17% impurities (HPLC) |
| JK-47.1 | 1:3 | EtOH/H$_2$O | EtOH | 10 min., 120° C. | 33% (HPLC) |

TABLE 3-continued

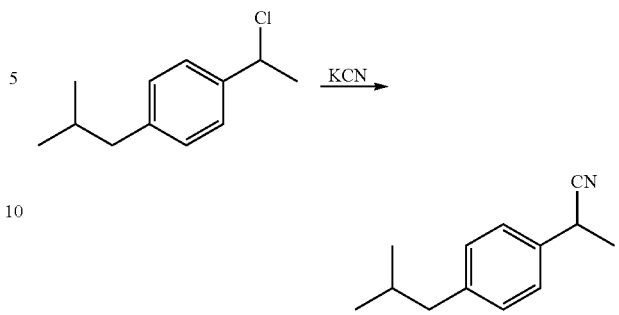

| Exp. | Stoich. | Solvent | Carrier | Conditions | Result |
|---|---|---|---|---|---|
| JK-47.2 | 1:3 | EtOH/H$_2$O | EtOH | 10 min., 160° C. | 32% (HPLC) |
| JK-47.3 | 1:3 | EtOH/H$_2$O | EtOH | 10 min., 200° C. | 34% (HPLC) |

Figure 4:
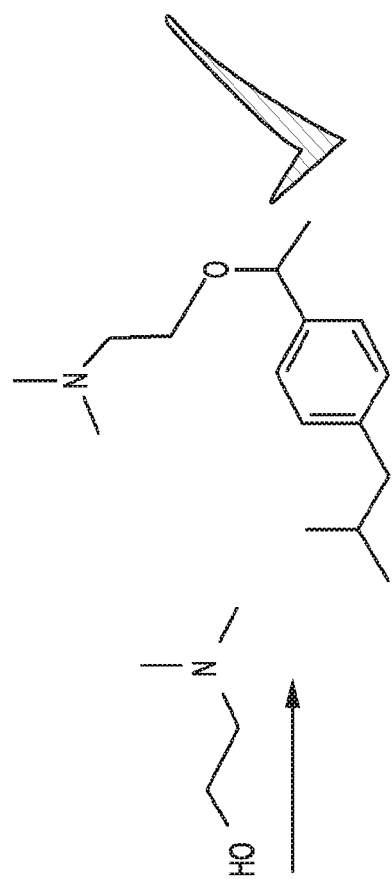
FIG. 4 shows a representative test reaction involving the nucleophilic substitution of a chloride.
Figure 4:
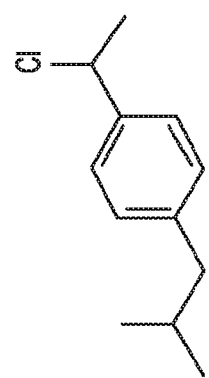

See FIG. 4 for a test reaction.

a. Step 1: Acylation

Figure 5:
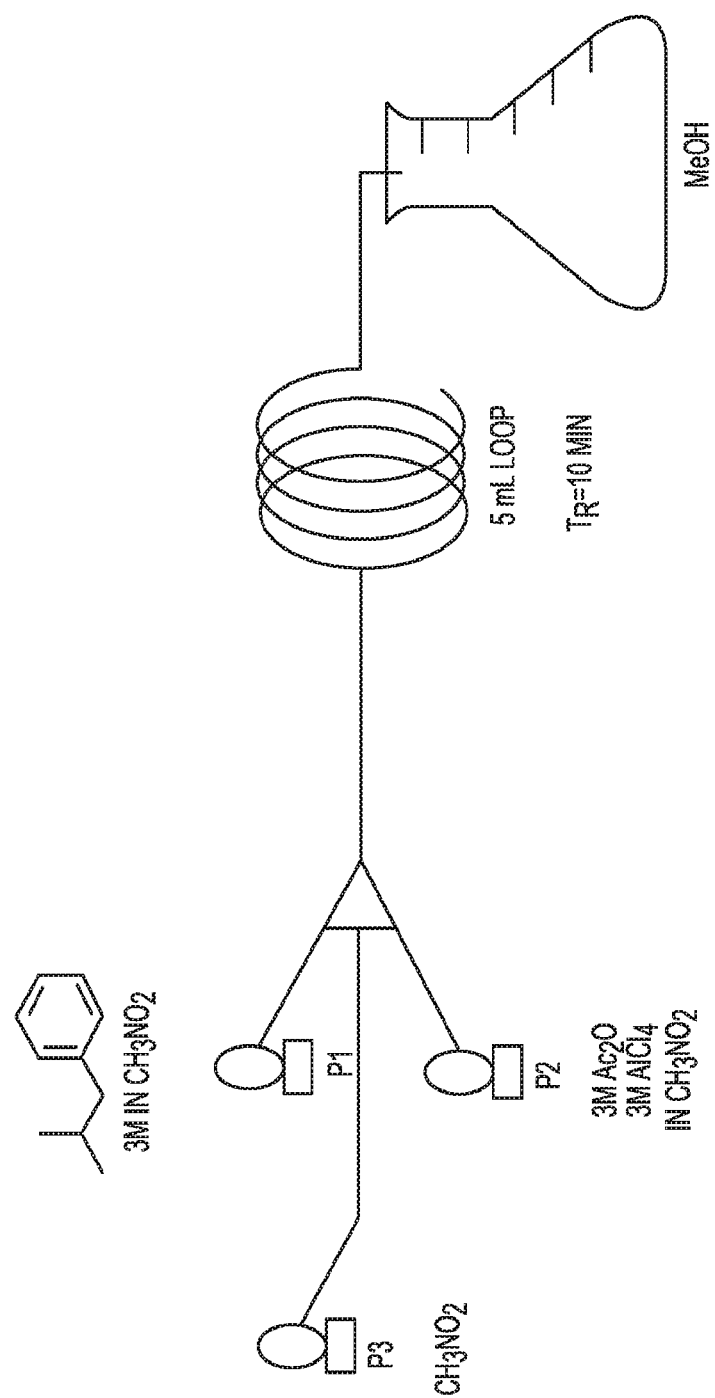
FIG. 5 shows a representative diagram illustrating the acylation step via a syringe pump.

A list of conditions to facilitate the transformation from isobutylbenzene to 1-(4-isobutylphenyl)ethanone using a syringe pump is shown in Table 4. See also FIG. 5.

TABLE 4

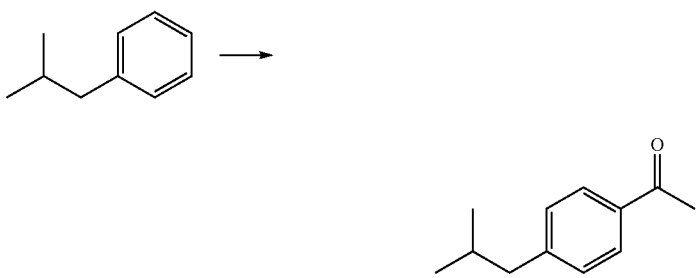

| Exp | Lewis Acid | AcX | Solvent | Stoich. | Temp. | Result |
|---|---|---|---|---|---|---|
| JK-50 | EtAlCl$_2$ (0.9M Hep) | Ac$_2$O | DCM | 1:1:0.2 | 0° C. | Complete conversion + impurities |
| JK-51 | EtAlCl$_2$ (0.9M Hep) | Ac$_2$O | XS IBB | 2.2:1:0.2 | 0-rt, 1 h | Gelled out, no reaction |
| JK-53A | 1.4M AlCl$_3$ in CH$_3$NO$_2$ | Ac$_2$O | IBB | 1:1:1 | 0-rt | Gelled out, 22% (HPLC) |
| JK-53B.1 | 1.4M AlCl$_3$ in CH$_3$NO$_2$ | Ac$_2$O | CH$_3$NO$_2$ | 1:1:0.3 | rt, 40° C. | No reaction |
| JK-53B.2 | Above + 100 mg AlCl$_3$ | Ac$_2$O | CH$_3$NO$_2$ | 1:1:0.8 | rt, 5 min | 90% (HPLC) |
| JK-55A | 3M AlCl$_3$/3M Ac$_2$O Soln in CH$_3$NO$_2$ | (Ac$_2$O) | CH$_3$NO$_2$ | 1:1:1 | rt, 5 min | Complete conversion |
| JK-55B | 3M AlCl$_3$ in CH$_3$NO$_2$ | Ac$_2$O | Ac$_2$O | 1:12:1 | | Gel on addition of AlCl$_3$ solution |
| JK-55C | 3M AlCl$_3$/3M Ac$_2$O Soln in CH$_3$NO$_2$ | (Ac$_2$O) | XS IBB | 1:1:1 | rt | Gel on addition of AlCl$_3$ solution |
| JK-56 | 3M AlCl$_3$/3M Ac$_2$O Soln in CH$_3$NO$_2$ | (Ac$_2$O) | CH$_3$NO$_2$ | 1:1:1 | rt/10 min | 100% (HPLC) | b. Step 2: Reduction

A list of conditions explored to facilitate the transformation from 1-(4-isobutylphenyl)ethanone to 1-(4-isobutylphenyl)ethan-1-ol using a syringe pump is shown in Table 5.

TABLE 5

| Exp | Ketone | Reducing Agent | Conditions | Result |
|---|---|---|---|---|
| JK-52A | JK-50 (work-up) | DIBAL/tol | 1:1, 0° C. | Complete |
| JK-52B | JK-50 (work-up) | LiBH$_4$/THF | 1:1, 0° C. | Complete |
| JK-57A | JK-56 MeOH quench | 3M LiBH$_4$/THF | 1:1:2, RT | Crude HPLC ~10%; 19 mg (7%) isolated |
| JK-57B | JK-56 work-up | 3M LiBH$_4$/THF | TBD | |
| JK-58A | JK-56 MeOH quench | NaBH$_4$ | 1:2.2, RT | |
| JK-58B | JK-56 work-up | NaBH$_4$ | TBD | |
| JK-59A | JK-56 MeOH quench | AlO-iPr/IPA | 1:1, RT | |
| JK-59B | JK-56 work-up | AlO-iPr/IPA | TBD | |

Note,
LiBH$_4$ reduction has been done in flow. Difference here is the acetophenone now contains MeOH from F.C. quench.

The reaction mixtures from JK-52A and -52B were treated with 10 eq. concentrated HCl (Scheme 11). However, HPLC indicated that no reaction had occurred. Without wishing to be bound by theory, it is possible there was a vial headspace issue.

SCHEME 11.

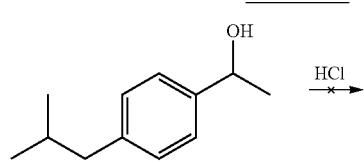

An alternative strategy to access the cyanide was also attempted via the syringe pump flow system, as shown in Table 6.

TABLE 6

| Exp. | Lewis Acid | AcX | Solvent | Stoich. | Temp. | Result |
|---|---|---|---|---|---|---|
| JK-62A | 2M AlCl$_3$ in CH$_3$NO$_2$ (2.2 eq) | Ac$_2$O | IBB | 1:1:2.2 | RT/15 min | Complete (1H NMR, HPLC) |
| JK-62B | 2M AlCl$_3$ in CH$_3$NO$_2$ (2.2 eq) | AcCl | IBB | 1:1:2.2 | RT/15 min | Complete (1H NMR, HPLC) |

A summary of conditions to facilitate the transformation from 1-(4-isobutylphenyl)ethanone to 1-(4-isobutylphenyl)ethan-1-ol using either a vial reaction or the syringe pump flow system is shown in Table 7.

TABLE 7

| Exp | Ketone | Reducing Agent | Conditions | Result |
|---|---|---|---|---|
| Vial Reactions | | | | |
| JK-57 | Flow F.C. MeOH quench | 3M LiBH$_4$/THF | 1:1:2, RT | Crude HPLC ~10%; 19 mg (7%) isolated |

TABLE 7-continued

| Exp | Ketone | Reducing Agent | Conditions | Result |
|---|---|---|---|---|
| JK-58 | Flow F.C. MeOH quench | NaBH$_4$ | 1:2.2, RT | 98% (1H NMR), 20 h |
| JK-59 | Flow F.C. MeOH quench | AlO-iPr/IPA | 1:1, RT | No reaction (1H NMR) |
| Syringe Pump Flow System | | | | |
| JK-60 | JK-50wu | 1.2M NaBH$_4$/MeOH | 2.2:1, 5:1 | No reaction |
| JK-61 | JK-50wu | 1.2M NaBH$_4$/MeOH | 2.2:1 | 4% (HPLC) |
| JK-63A | JK-62A + toluene | 1M DIBAL/toluene | 1:1, 1:2 | 70% (1 eq, 15 min-16 h), 98% (2 eq, 30 min) |
| JK-63B | JK-62B + toluene | 1M DIBAL/toluene | 1:1, 1:2 | 53% (1 eq, 15 min-16 h), 99% (2 eq, 30 min) |
| JK-63C | JK-27wu | 1M DIBAL/toluene | 1:1 | 98% (1 eq, 15 min) | c. Step 3: Chlorination

A summary of conditions to facilitate the transformation from 1-(4-1-(4-isobutylphenyl)ethan-1-ol to 1-(1-chloroethyl)-4-isobutylbenzene using vial reactions is shown in Table 8.

TABLE 8

| Exp | R—OH | Conditions | Result |
|---|---|---|---|
| JK-64A | JK-63A | Toluene rxn mix/20 eq conc HCl, 1 h | ~95% (1H NMR) |
| JK-64B | JK-63B | Toluene rxn mix/20 eq conc HCl, 1 h | ~95% (1H NMR) |
| JK-64C | JK-63C | Toluene rxn mix/20 eq conc HCl, 4 h | Starting material consumed + impurities, ~80% (1H NMR) |

Figure 6:
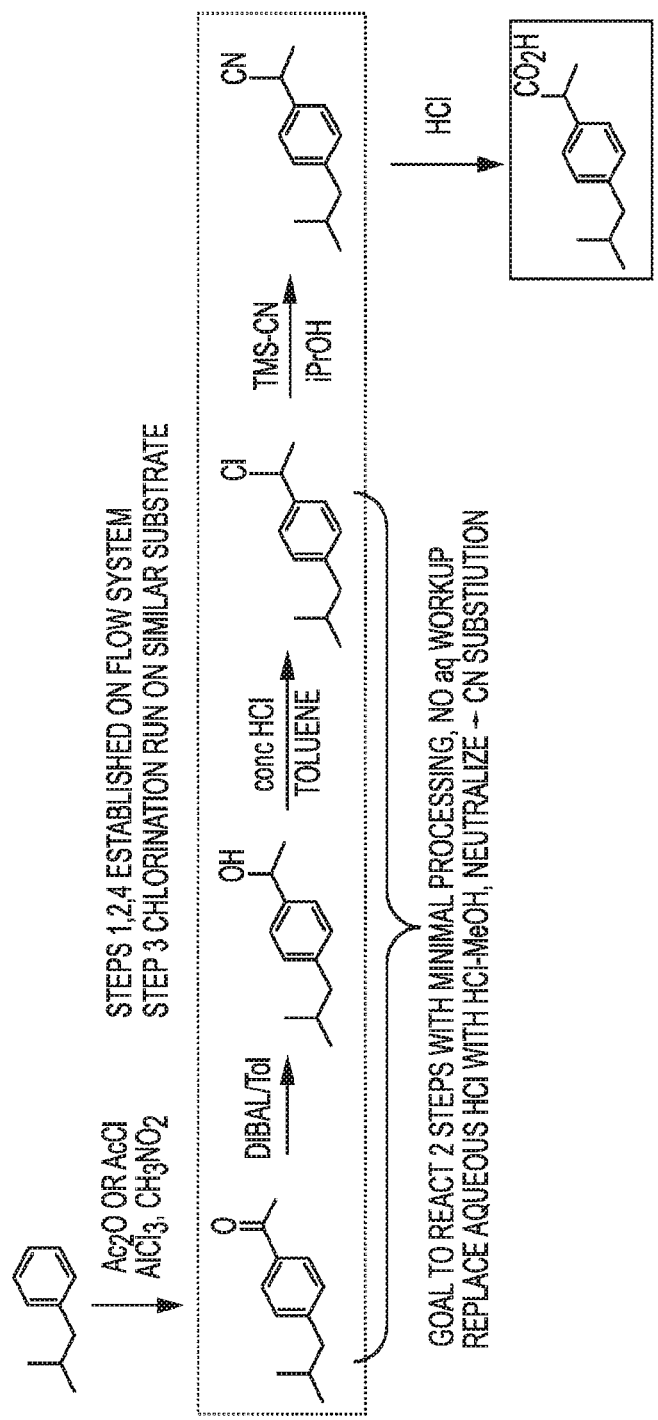
FIG. 6 shows a representative synthetic route to ibuprofen via a flow system.

FIG. 6 shows a synthetic route to ibuprofen.

To establish whether the chlorination could be run effectively in flow, the chlorination was performed on the AutoSyn system. The chemical conversion was successful. The LLS proved problematic, however, passing significant aqueous phase with the organic phase. Also, the BPR adjustment requires too much user input, and adjustments had to be made constantly during the run. A BPR>100 psi was needed for the reaction.

d. Step 4: Cyanation

Contrary to the literature reports, vial reactions of the cyanide substitution afforded poor results. Thus, screening conditions in flow may give better conversions (Table 9).

TABLE 9

| Exp | R—CN | Solvent/Carrier | Conditions | Result |
|---|---|---|---|---|
| JK-67.1 | TMS-CN | IPA/IPA | 600 μL plug (0.15M), 1:2, 160° C., 10 min | New peak RRT 1.03, suspect HMR |
| JK-67.2 | TMS-CN | IPA/IPA | 600 μL plug (0.15M), 1:2, 140° C., 10 min | New peak RRT 1.03, suspect HMR |
| JK-67.3 | — | IPA/IPA | 300 μL plug (0.3M), 1:0, 160° C., 10 min | New peak RRT 1.03, suspect HMR |
| JK-73.1 | TMS-CN | Tol/Tol | 750 μL plug (0.3M), 1:2, 120° C., 15 min | No reaction |

TABLE 9-continued

[Structure: 1-chloro-1-(4-isobutylphenyl)ethane → 2-(4-isobutylphenyl)propanenitrile]

| Exp | R—CN | Solvent/Carrier | Conditions | Result |
|---|---|---|---|---|
| JK-73.2 | NaCN | Tol-H2O/Tol | 750 μL plug (0.3M), 1:2, 120° C., 15 min | No reaction |
| JK-73.3 | NaCN/TBAI | Tol-H2O/Tol | 750 μL plug (0.3M), 1:2, 120° C., 15 min | No reaction |

Figure 7A:
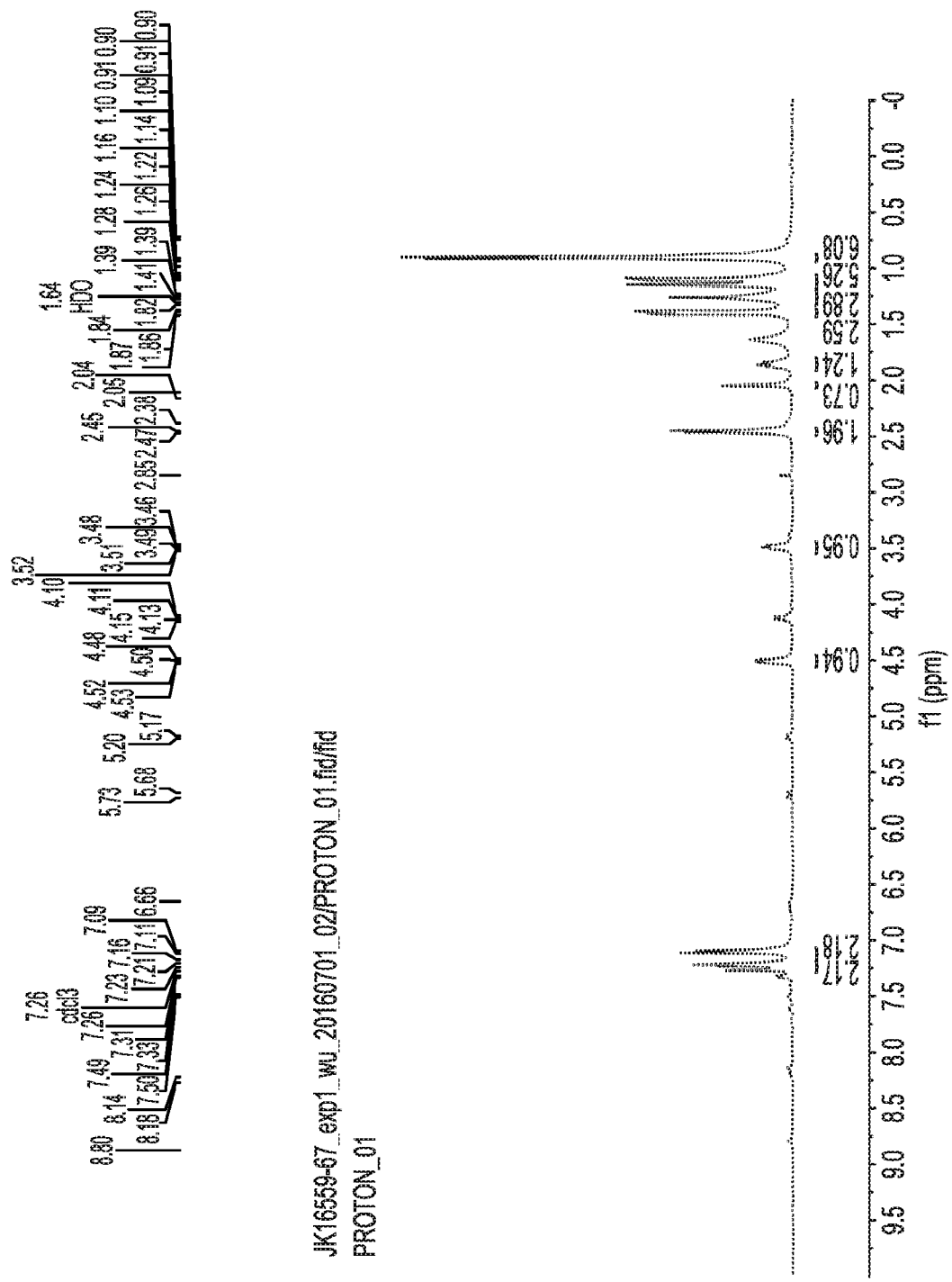
FIG. 7A and FIG. 7B show representative $^1$H NMR (8A) and $^{13}$C NMR (8B) spectra of JK-67.1.
Figure 7B:
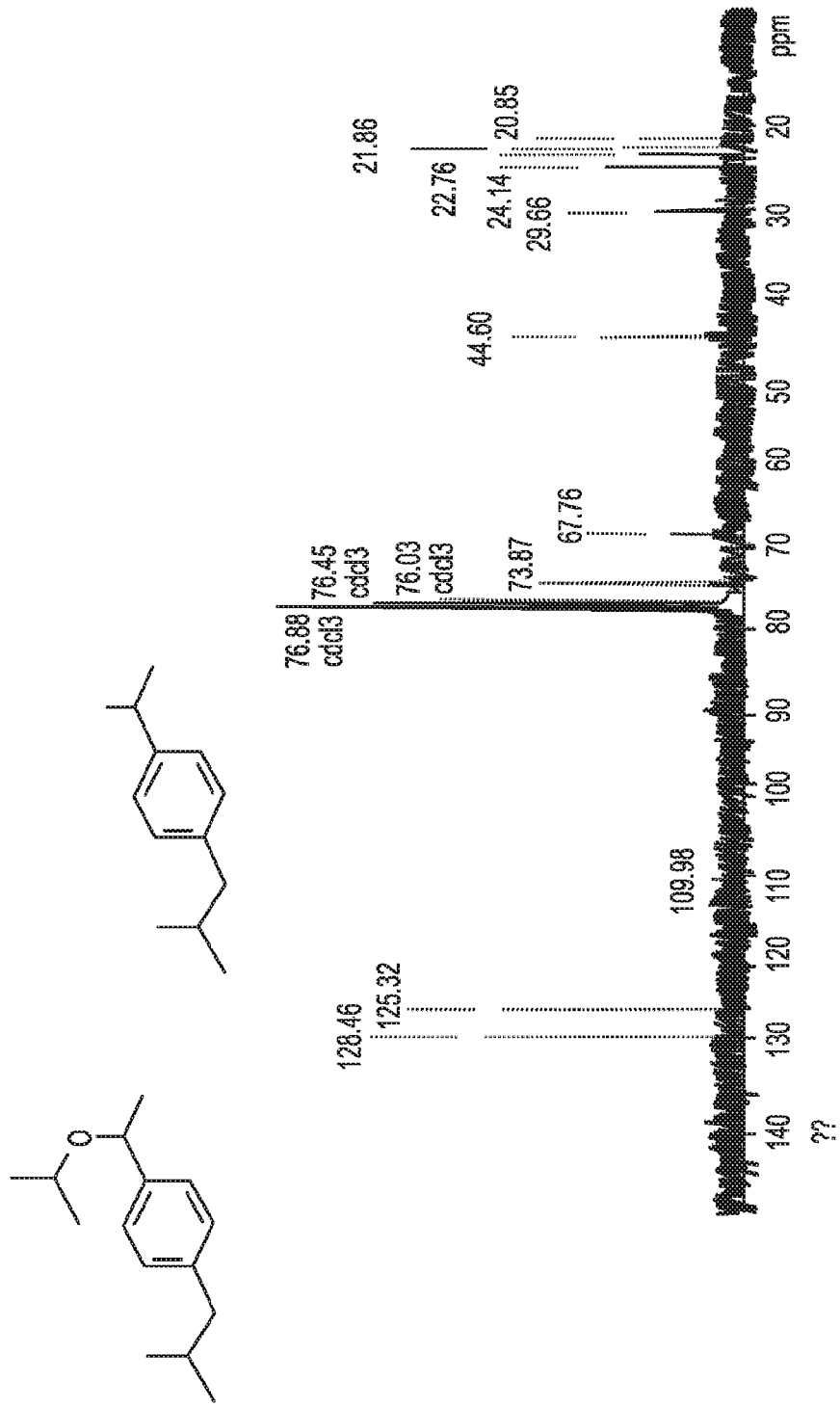

Representative $^1$H NMR and $^{13}$C NMR spectra of JK-67.1 are shown in FIG. 7A and FIG. 7B, respectively. The isopropyl alcohol may give possible isopropyl addition and toluene gives no reaction. Polar aprotic solvents (e.g., ACN and DMF) could be explored (NMP is not compatible).

Figure 8:
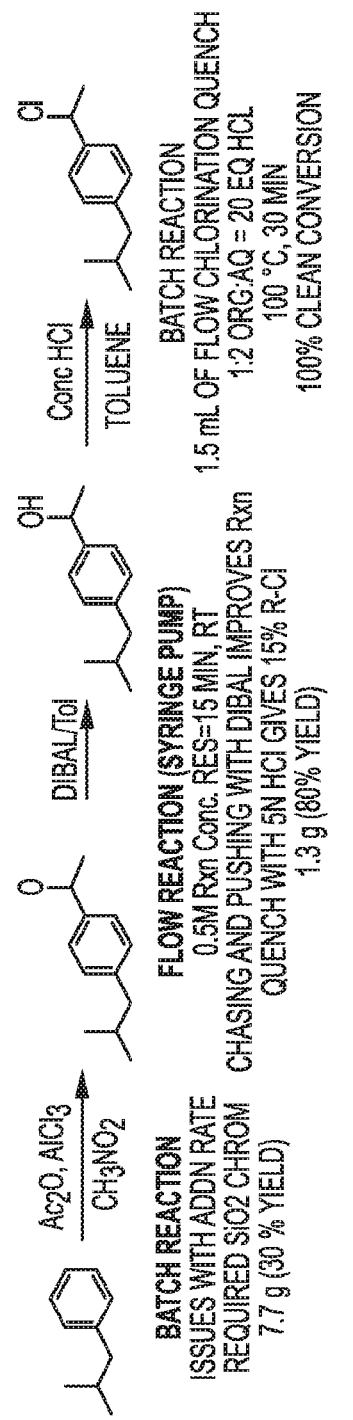
FIG. 8 shows a representative synthetic route to the benzyl chloride intermediate using both batch and flow reactions.

As shown in FIG. 8, the benzyl chloride intermediate was resynthesized to prepare more of the chloride analog for development of the CN substation, to repeat the DIBAL reduction on a significant scale, and to gain additional information about the HCl quench. The Friedel-Crafts acylation in $CH_3NO_2$ is better suited for flow. A side reaction was observed with time in the pot. 1.6 g of acetophenone intermediate was reduced in flow at 0.5M. Quenching with 5N HCl at RT gives 15% of the chloride analog. Heating at 100° C. for 30 min gives a complete conversion.

Figure 9:
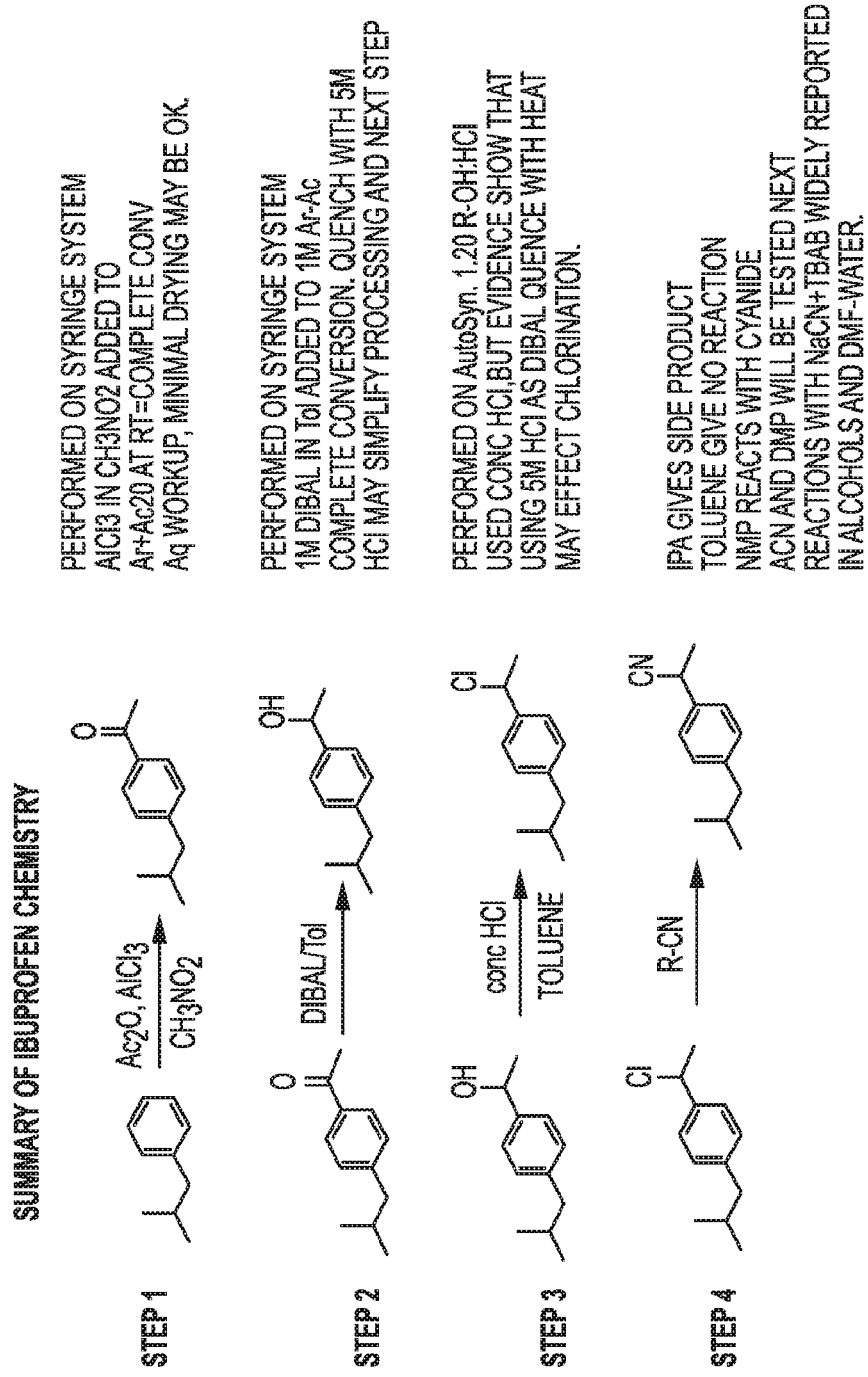
FIG. 9 shows a representative summary of Steps 1-4 to ibuprofen.

A summary of Steps 1-4 of the ibuprofen chemistry is shown in FIG. 9.

e. Applying VapourTec to the Synthesis of Ibuprofen

Data corresponding to the chlorination of ibuprofen is shown in Tables 10 and 11.

TABLE 10

| 16554-68 | SM:5M HCl (flow rate) | 5M HCl (eq) | Conversion by NMR |
|---|---|---|---|
| a | 1:1 | 20 | 50 |
| b | 1:2 | 40 | 65 |
| c | 1:5 | 100 | 44 |

TABLE 11

| | HCl (M) | HCl (equiv) | % conv. By NMR | Notes |
|---|---|---|---|---|
| Autosyn | 6 | 24 | 69 | LLE membrane broke and clogged |
| VapourTec | 8 | 32 | 100 | — |
| VapourTec | 10 | 40 | 100 | Clogged reactor and bpr |

Figure 10:
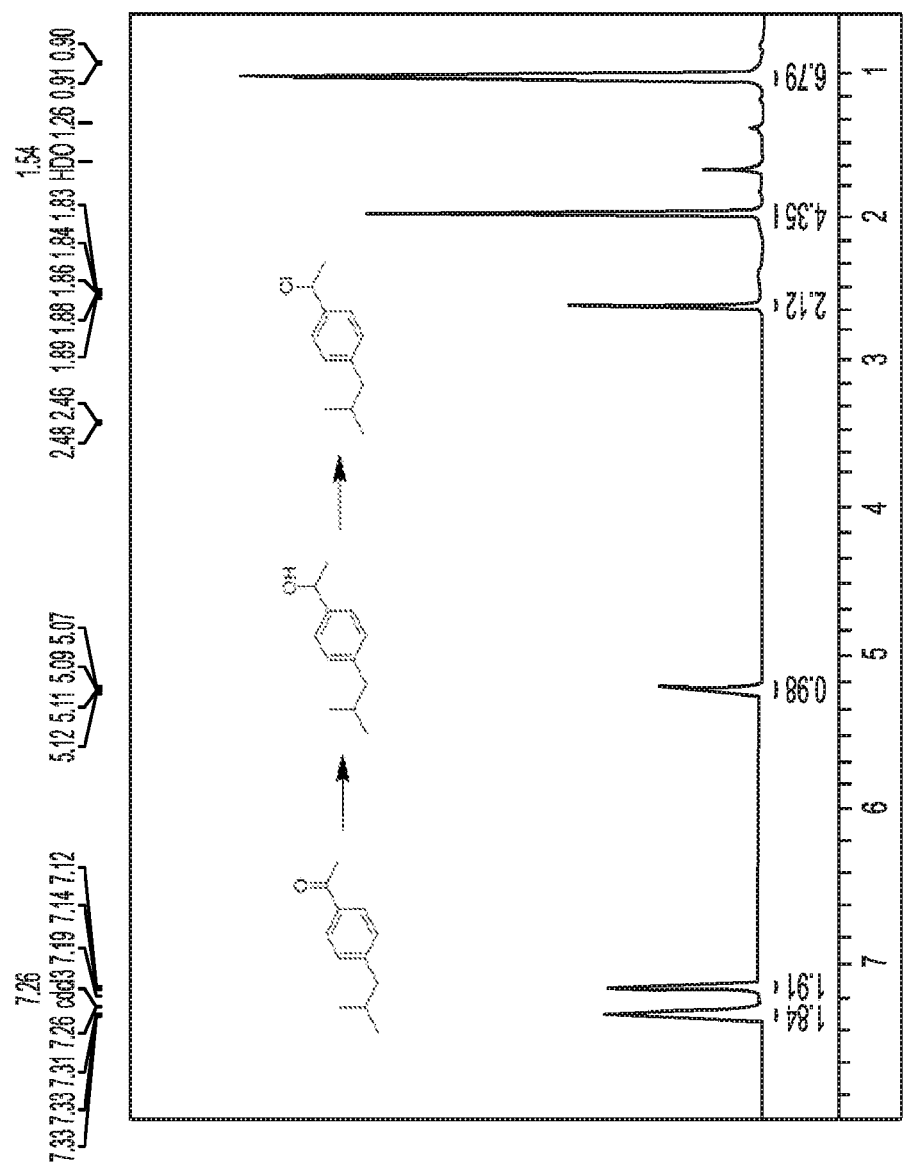
FIG. 10 shows a representative $^1$H NMR spectrum of the chloro derivative.
Figure 11:
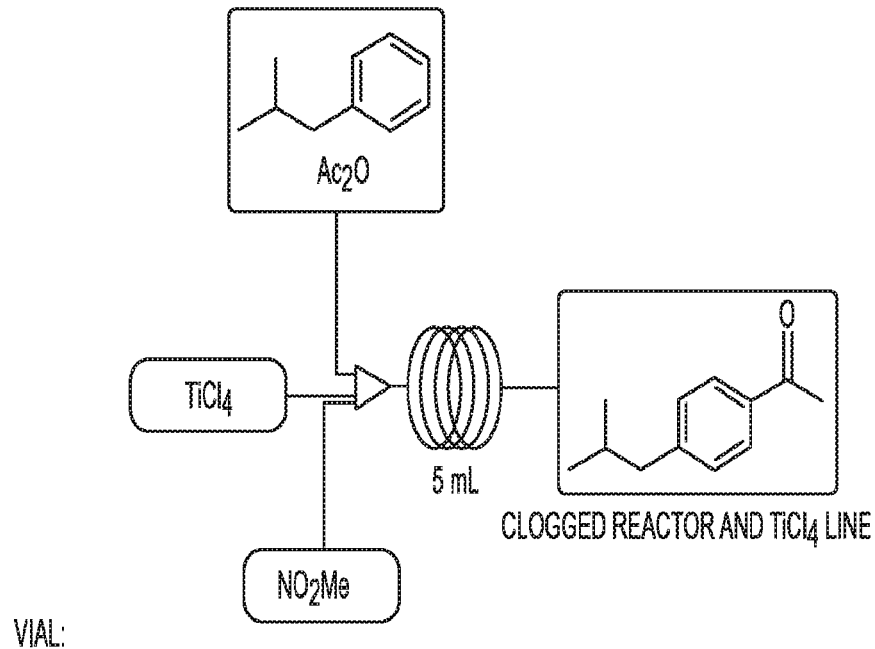
FIG. 11 shows a representative diagram illustrating the acylation step via a syringe pump.

A $^1$H NMR corresponding to the chloro derivative obtained after performing the reduction and chlorination steps on VapourTex is shown in FIG. 10.
A diagram illustrating the Friedel-Crafts step on the VapourTec system is shown in FIG. 11.

Figure 12:
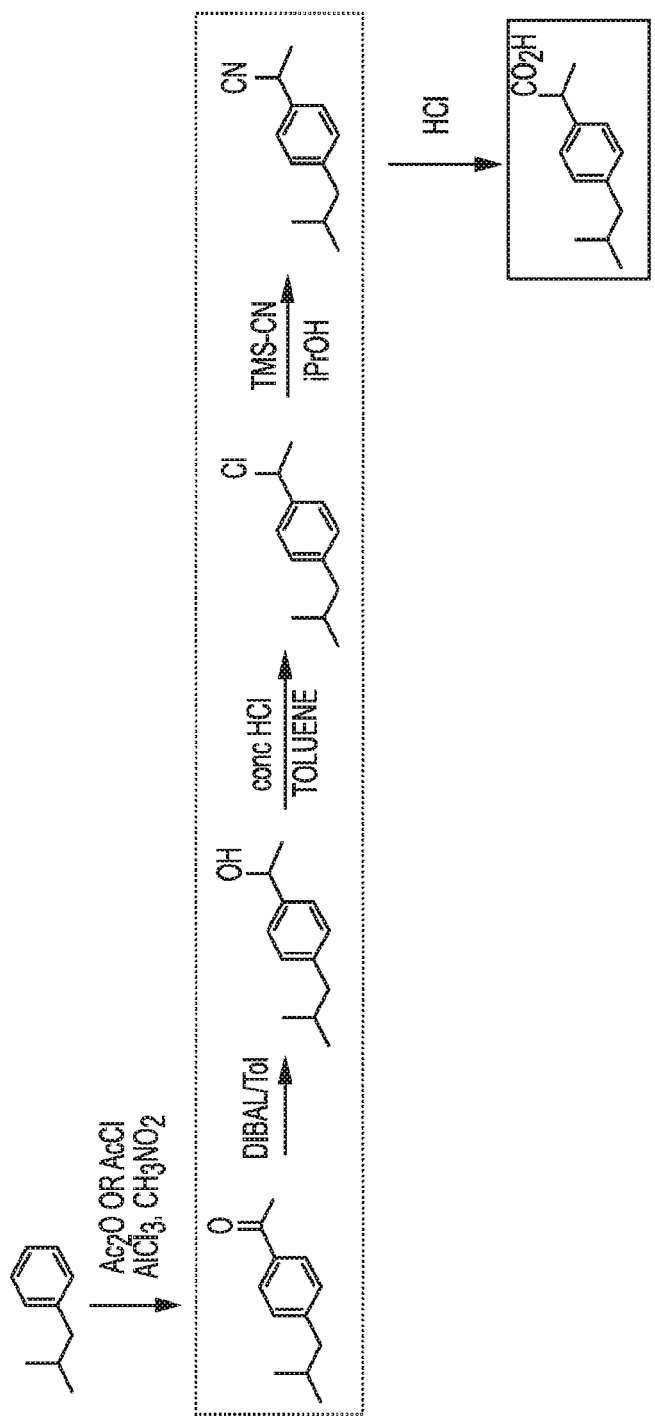
FIG. 12 shows a representative synthetic route to ibuprofen on the VapourTec system.
Figure 13A:
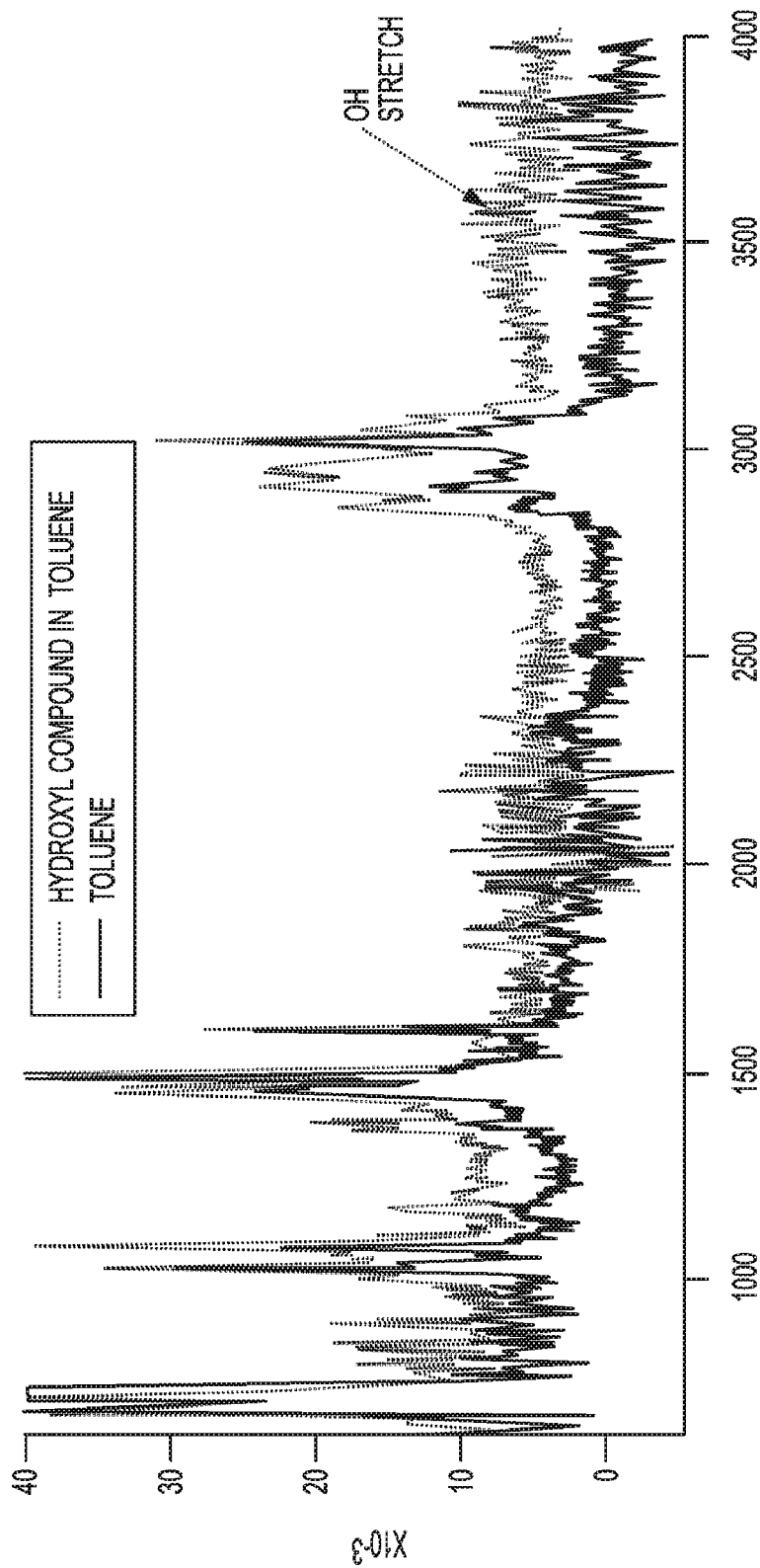
FIG. 13A-D show representative FTIR spectra of the hydroxyl (13A), chloro (13B), and carbonyl (13C, minus solvent; 13D, in toluene) compounds.
Figure 13B:
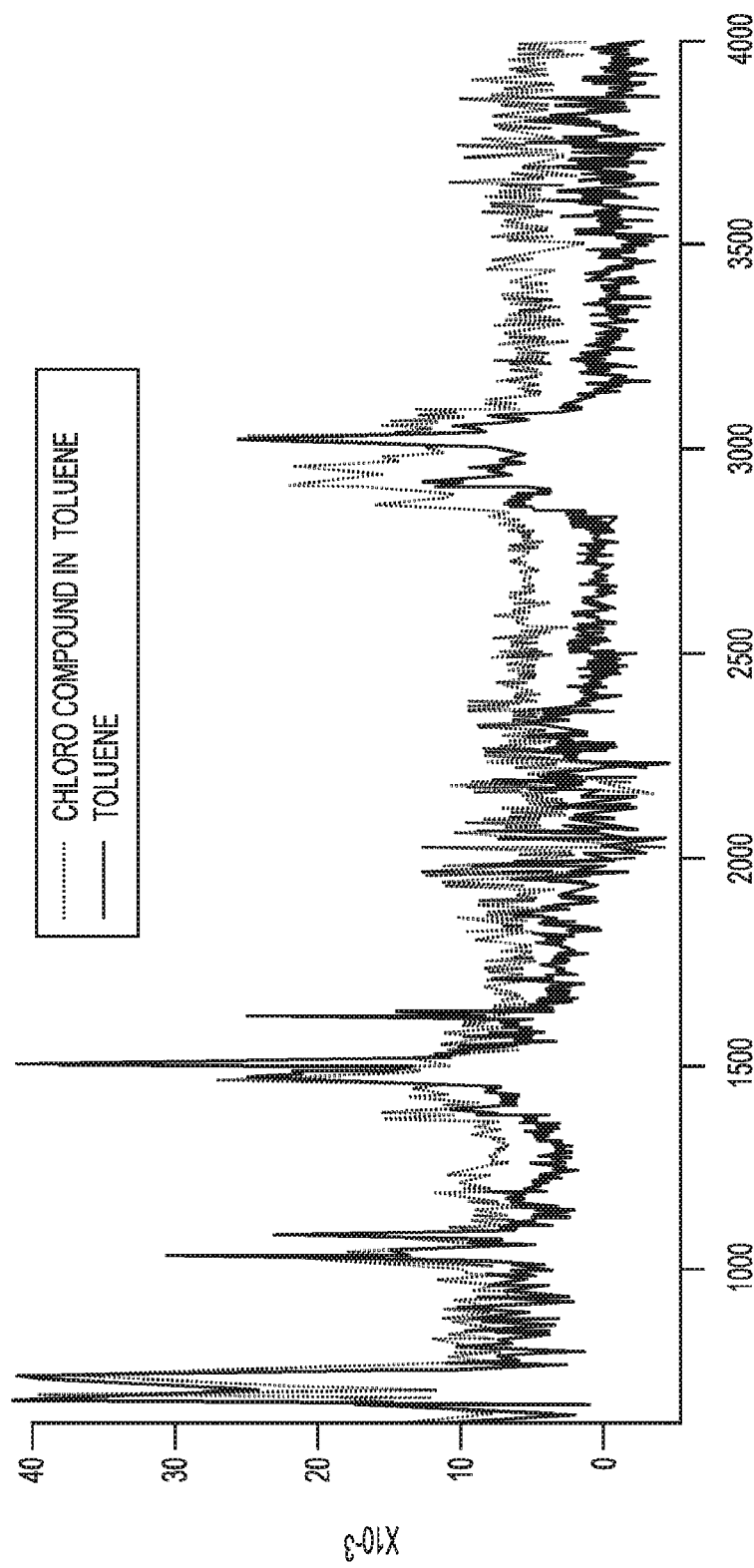
Figure 13C:
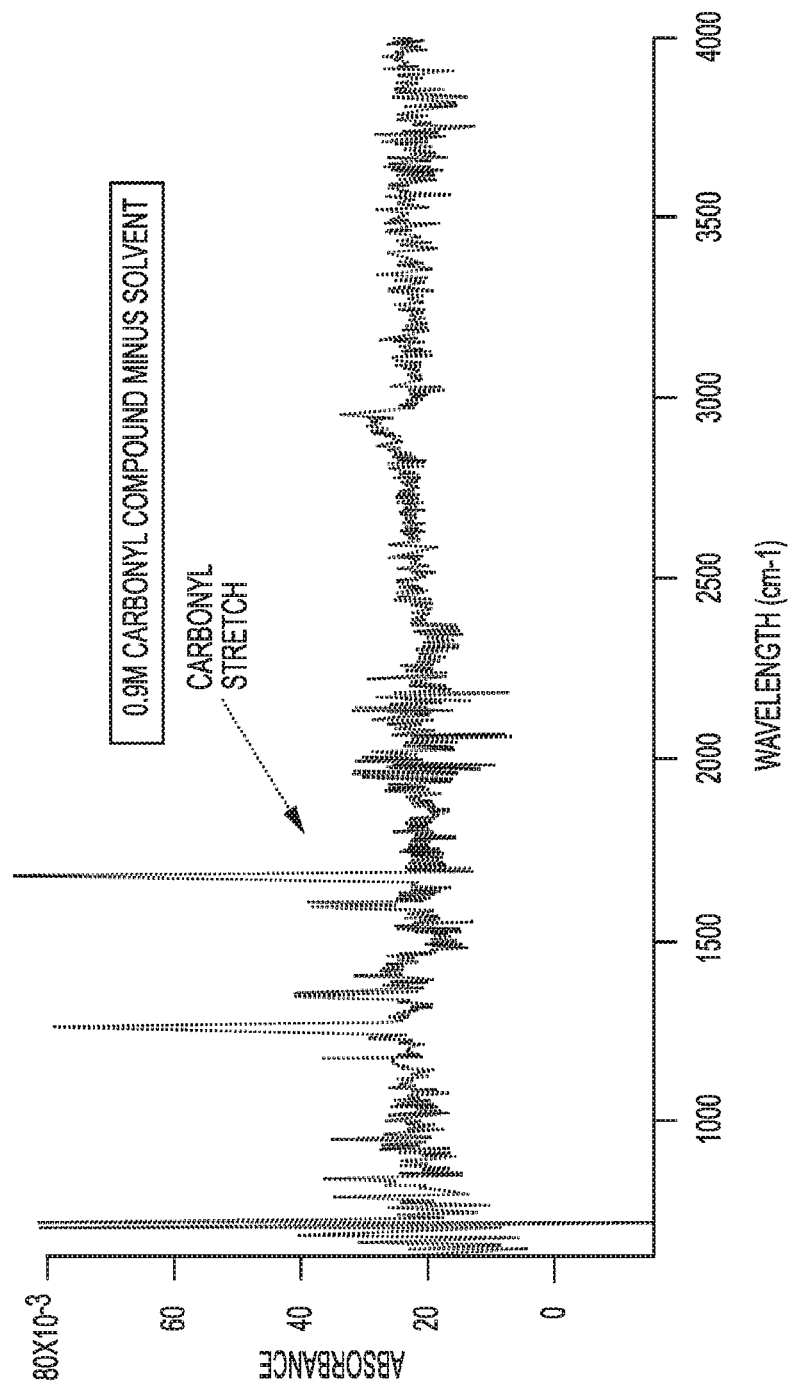
Figure 13D:
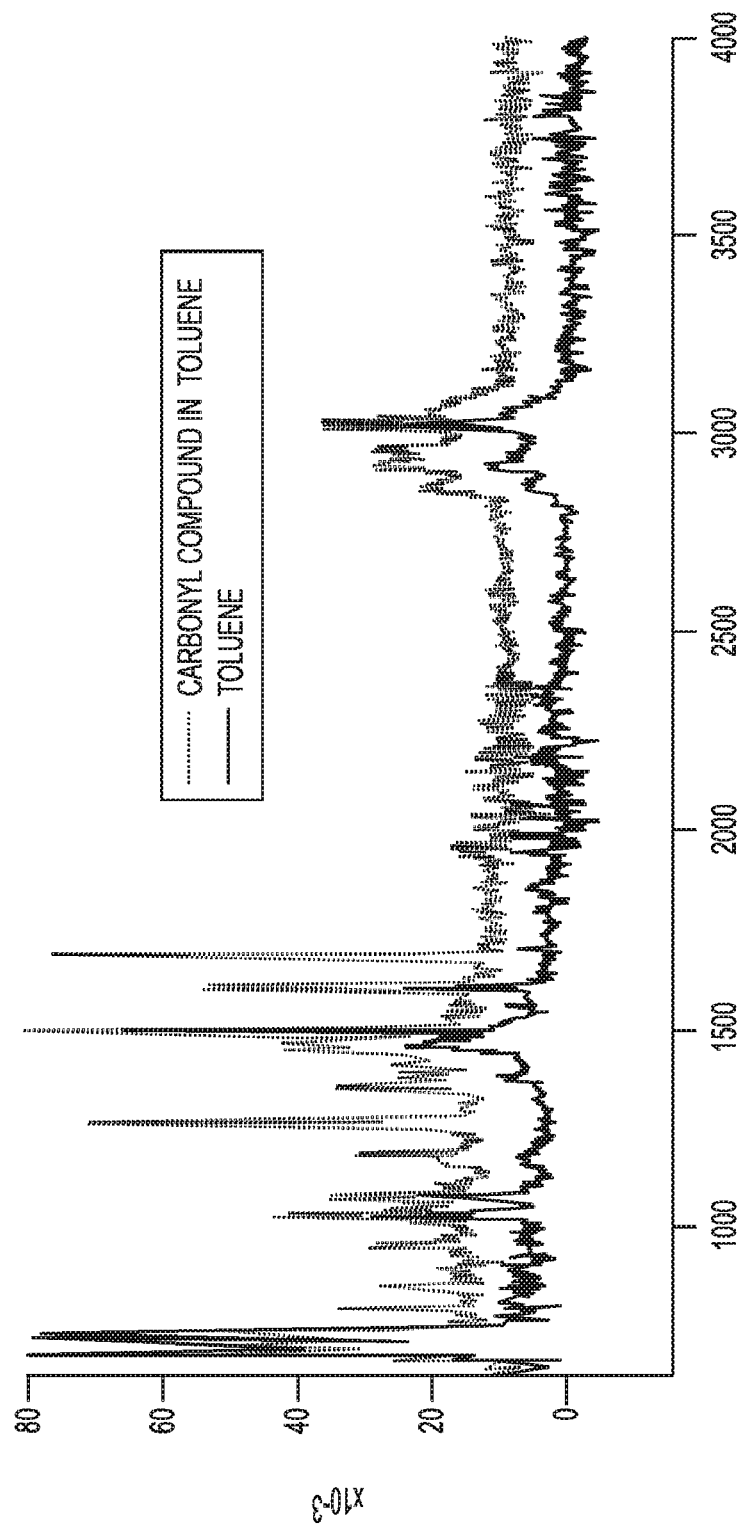

A summary of the synthesis of ibuprofen on the VapourTec system is shown in FIG. 12.

2. Optimization of Step 4

A list of conditions for the cyanide substitution using the Synfini flow screen with acetonitrile is shown in Table 12.

TABLE 12

[Structure: 1-chloro-1-(4-isobutylphenyl)ethane → 2-(4-isobutylphenyl)propanenitrile]

| Exp | R—CN | Solvent/Carrier | Conditions | Result |
|---|---|---|---|---|
| JK-79A | NaCN | ACN-H$_2$O (1:3)/ACN | 900 μL plug (0.17M), 1:5, 120° C., 10 min | New peak RRT 0.86 (31%) |
| JK-79B | KCN | ACN-H$_2$O (1:3)/ACN | 900 μL plug (0.17M), 1:5, 120° C., 10 min | New peak RRT 0.86 (16%) |
| JK-79C | NaCN/TBAI | ACN-H$_2$O (1:3)/ACN | 900 μL plug (0.17M), 1:5:0.2, 140° C., 10 min | New peak RRT 0.86 (25%) |

A list of conditions for the cyanide substitution using a solvent screen in vials is shown in Table 13.

TABLE 13

| Exp | Method | Reagents | Solvent | Conditions | Result |
|---|---|---|---|---|---|
| JK-77A | Vial | 2.4 eq NaCN + 0.2 eq TBAI | Tol | 90° C./4 h | No reaction |
| JK-77B | Vial | 5 eq NaCN + 0.2 eq TBAI | DMF | 90° C./4 h | New peak RRT 0.86 (58%) |
| JK-77C | Vial | 5 eq NaCN + 0.2 eq TBAI | DMSO | 90° C./4 h | New peak RRT 0.86 (78%) |
| JK-77D | Vial | 5 eq NaCN + 0.2 eq TBAI | ACN | 90° C./4 h | New peak RRT 0.86 (4%) |
| JK-77E | Vial | 5 eq NaCN + 0.2 eq TBAI | 2-Me-THF | 90° C./4 h | New peak RRT 0.86 (17%) |

Off-line FTIR spectra were taken for toluene solutions of the carbonyl, hydroxyl, and chloro precursors to ibuprofen (see FIG. 12 and FIG. 13A-D). The concentrations ranged from 0.9M to 0.22M. The 0.9M solution of the carbonyl compound gave a decent spectrum but the ~0.2M solutions had to be concentrated by evaporating the solvent to improve the quality of the spectra. The neat toluene spectrum was fairly noisy.

In summary, isopropyl alcohol was ruled out as a solvent because it is reactive. A mixture of toluene-water did not work in flow with NaCN/NaCN+ TBAI. The peak at RRT 0.86 isolated (JK-77B) matches the literature reference for R—CN. DMSO and DMF offered promising results.

A list of conditions screened using DMF in flow is shown in Table 14. Poor conversion was achieved using DMF and TBAI in flow. Apparent decomposition of DMF was observed at temperatures greater than 160° C.

TABLE 14

| Exp | Method | Reagents | Solvent | Conditions | Result |
|---|---|---|---|---|---|
| JK-80A | Flow | 5 eq NaCN | DMF | 140° C./20 min | 17% (HPLC) + impurities |
| JK-80B | Flow | 5 eq NaCN + 0.2 eq TBAI | DMF | 140° C./20 min | 14% + impurities |
| JK-80C | Flow | 20 eq NaCN + 0.2 eq TBAI | DMF | 200° C./40 min | 17% + impurities, severe darkening of DMF push solvent |
| JK-80D | Flow | 20 eq NaCN + 0.2 eq TBAI | DMF | 160° C./20 min | 24% + impurities |

A list of conditions using benzyltriethylammonium chloride (TEBAC) in vials is shown in Table 15. A 1:1:1 DMSO-Toluene-Water mixture gave complete conversion at 7 h. Toluene gave near complete conversion. Water does not appear to promote extended reaction times.

TABLE 15

| Exp | Method | Reagents | Solvent | Conditions | Result (anhydrous)/7 h | Result (with H$_2$O)/+2 h |
|---|---|---|---|---|---|---|
| JK-80A | Vial | 6 eq NaCN/ 0.1 eq TEBAC | DMF | 100° C. | 85% | 87% |
| JK-80B | Vial | 6 eq KCN/ 0.1 eq TEBAC | DMF | 100° C. | 68% | 70% |
| JK-80C | Vial | 6 eq KCN | DMF | 100° C. | 64% | 64% |
| JK-80D | Vial | 6 eq NaCN/ 0.1 eq TEBAC | Toluene* | 100° C. | 95% | 94% |
| JK-80E | Vial | 6 eq KCN/ 0.1 eq TEBAC | Toluene* | 100° C. | 95% | 95% |
| JK-80F | Vial | 6 eq KCN | Toluene* | 100° C. | 94% | 94% |
| JK-80G | Vial | 6 eq KCN/ 0.1 eq TEBAC | EtOH | 100° C. | 13% | 17% |
| JK-80H | Vial | 6 eq KCN/ 0.1 eq TEBAC | DMSO/Tol/H$_2$O (1:1:1) | 100° C. | 100% | — |

*Contradicts Flow result. Changes: TEBAC/vial.

To test toluene as a carrier solvent, DMSO as a plug additive, and to compare sodium cyanide and potassium cyanide, a series of conditions using Plug-Flow, toluene as the carrier solvent, and R—Cl in toluene were explored for the cyanation (Table 16). Although toluene works in the vial, it was not suitable as a push solvent. Slight promotion was achieved using DMSO in the plug, but still bi-phasic. No real change was observed with potassium cyanide versus sodium cyanide.

TABLE 16

| Exp | XCN | Plug (tol:H$_2$O:DMSO) | Eq (R—Cl:XCN:TEBAC) | Time | Temp. | Result (HPLC) |
|---|---|---|---|---|---|---|
| JK-86A | NaCN | 1:1:1 | 1:6:0.2 | 10 min | 160° C. | 10% |
| JK-86B | KCN | 1:1:1 | 1:6:0.2 | 10 min | 160° C. | 9% |
| JK-86C | NaCN | 1:1:0 (no DMSO) | 1:6:0.2 | 10 min | 160° C. | 6% |
| JK-86D | KCN | 1:1:0 (no DMSO) | 1:6:0.2 | 10 min | 160° C. | <5% |
| JK-86E | NaCN | 1:1:1 | 1:6:0.2 | 20 min | 120° C. | <5% |
| JK-86F | NaCN | 1:1:0 (no DMSO) | 1:6:0.2 | 20 min | 120° C. | <1% |

To test DMSO as the carrier solvent and DMSO as a plug additive, a series of conditions using Plug-Flow and DMSO as the carrier solvent were explored (Table 17). DMSO as a carrier solvent and 24 eq. KCN improved the reaction (see JK-86D: 5% to JK-87B: 32%), although the plug is still bi-phasic. Toluene in the plug with water in carrier decreases the rate by 0.5 times. Mixing/miscibility appears to be an issue.

TABLE 17

| Exp | XCN | Plug (tol:H₂O:DMSO) | Eq (R—Cl:XCN:TEBAC) | Time | Temp. | Result (HPLC) |
|---|---|---|---|---|---|---|
| JK-87A | KCN | 0:1:1 (no toluene) | 1:24:0.2 | 10 min | 160° C. | 32% |
| JK-87B | KCN | 1:1:0 (no DMSO) | 1:26:0.2 | 10 min | 160° C. | 17% |

To test a 3:1 mixture of DMSO-water as the carrier solvent with R—Cl in toluene, a series of conditions using Plug-Flow, 1.5M NaCN, 0.2M TEBAC in 3:1 DMSO-water mixture were explored (Table 18). Mixing issues were still evident when injecting a 0.5 mL plug of toluene into 3:1 DMSO-water.

TABLE 18

| Exp | XCN | Plug | Eq (R—Cl:XCN:TEBAC) | Time | Temp. | Result (HPLC) |
|---|---|---|---|---|---|---|
| JK-88A | NaCN | Toluene (0.25M) | 1:6:0.8 | 10 min | 120° C. | <3% |
| JK-88B | KCN | Toluene (0.25) | 1:6:0.8 | 10 min | 140° C. | <3% |

To test if TEBAC in a DMSO carrier promotes phase transfer, a series of conditions using Plug-Flow and 0.1M TEBAC in DMSO (~saturated) were explored (Table 19). Potassium cyanide and sodium cyanide gave a similar result at a relatively low temperature. Low conversion was observed even with no toluene in the plug and TEBAC in a DMSO carrier. Worse conversion was observed compared to JK-87A (DMSO carrier, no TEBAC).

TABLE 19

| Exp | XCN | Plug (tol:H₂O:DMSO) | Eq (R—Cl:XCN:TEBAC) | Time | Temp. | Result (HPLC) |
|---|---|---|---|---|---|---|
| JK-88C | NaCN | 1:1 (no DMSO) | 1:24:0.2 | 10 min | 140° C. | 14-17% |
| JK-88D | KCN | 1:1 (no DMSO) | 1:24:0.2 | 10 min | 140° C. | 13% |
| JK-88E | NaCN | 1:1 (no DMSO) | 1:24:0.2 | 20 min | 120° C. | 13% |
| JK-88F | KCN | 1:1:1 | 1:24:0.2 | 10 min | 160° C. | 20% |
| JK-88G | KCN | 0:1:1 (no toluene) | 1:24:0.2 | 10 min | 160° C. | 23.4% |

3. Vapourtec Runs

Figure 14:
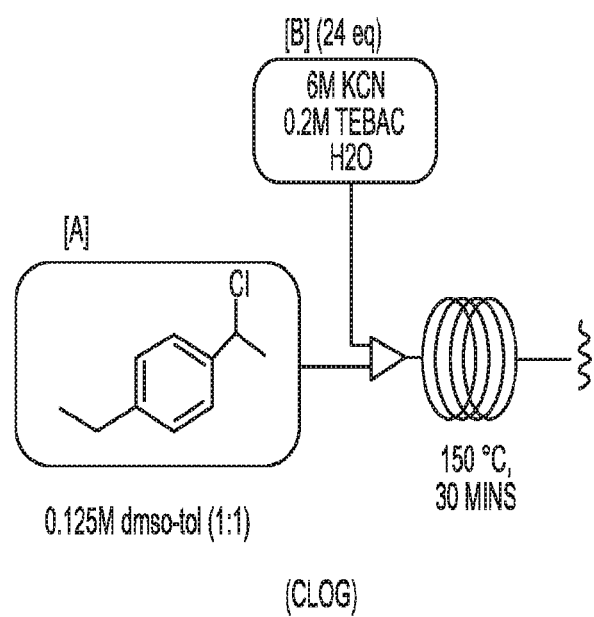
FIG. 14 shows a representative diagram illustrating a VapourTec run.
Figure 15:
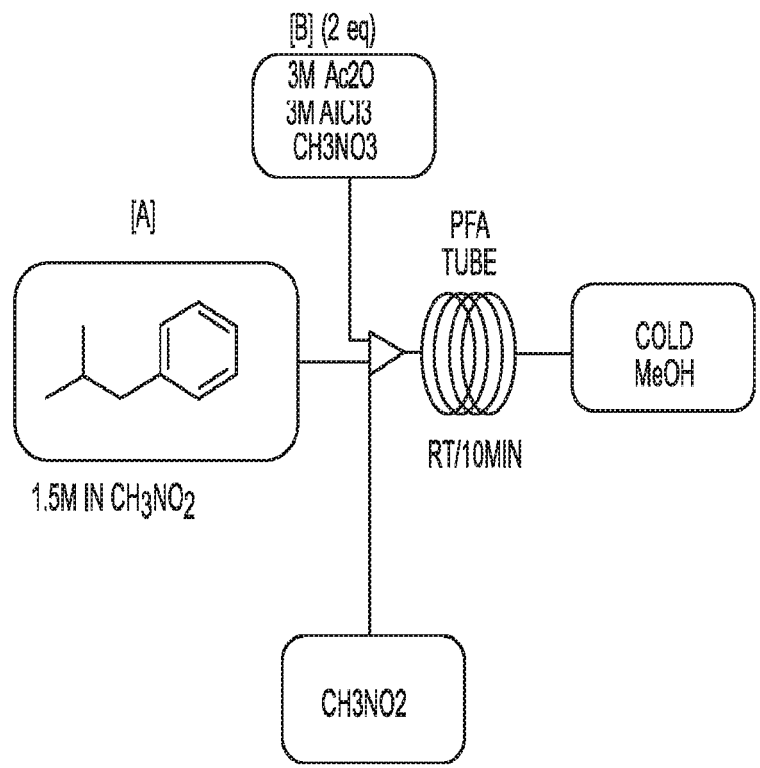
FIG. 15 shows a representative diagram illustrating syringe pump flow Friedel-Crafts (FC) acylation of isobutylbenzene.
Figure 16A:
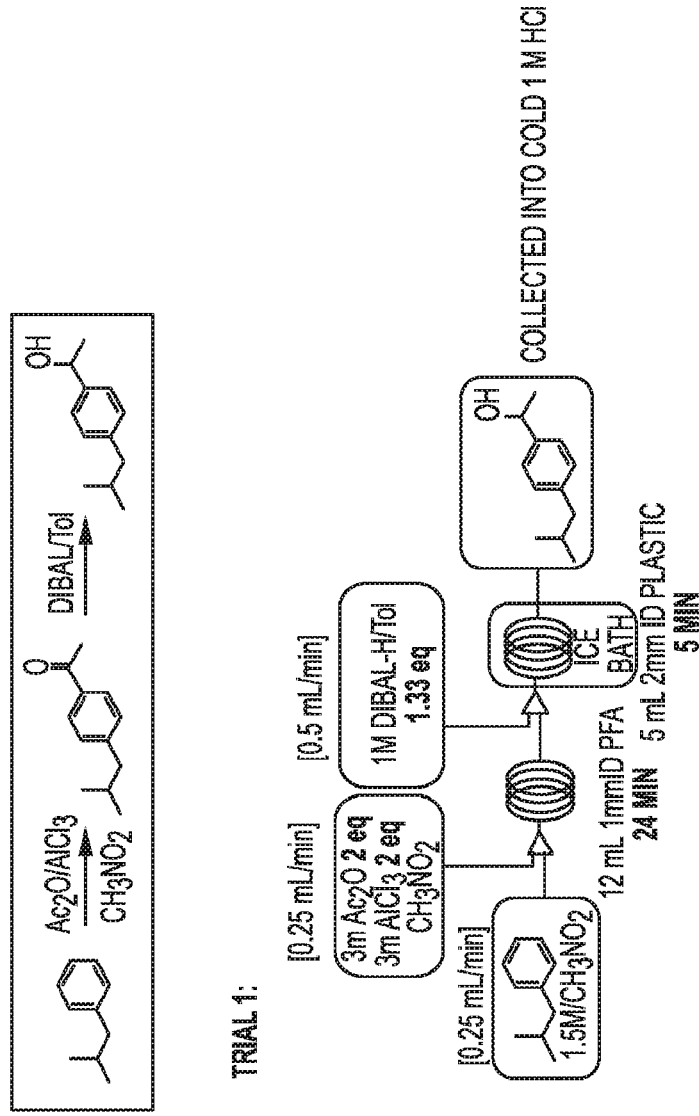
FIG. 16A and FIG. 16B show representative diagrams illustrating the two step flow synthesis of benzyl alcohol using a syringe pump system. Specifically.
Figure 16B:
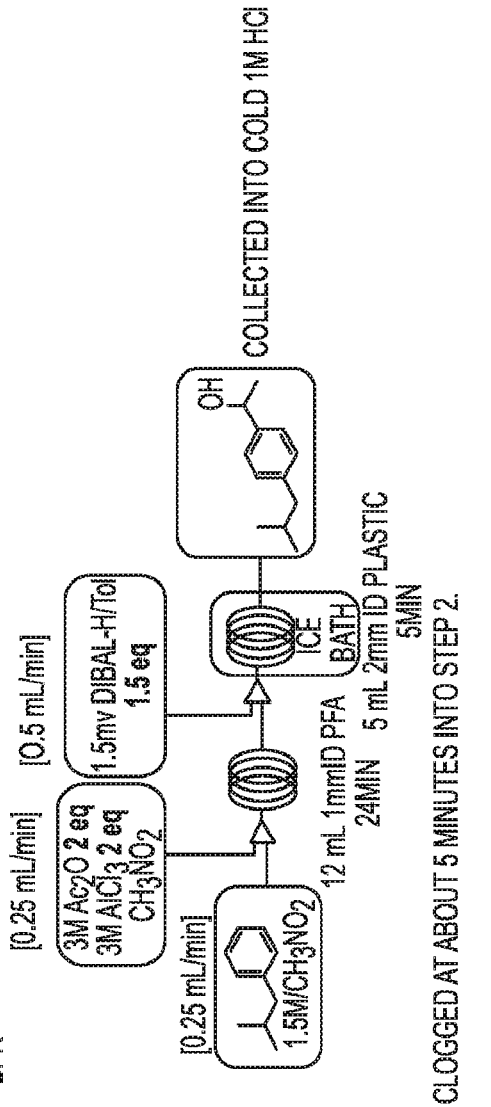

A diagram illustrating a VapourTec run is shown in FIG. 14. A diagram illustrating a syringe pump flow Friedel-Crafts reaction of isobutylbenzene is shown in FIG. 15. A diagram illustrating the two step flow synthesis of benzyl alcohol using a syringe pump system is shown in FIG. 16A and FIG. 16B.

A list of batch reactions comparing heat and sonication with finely ground sodium cyanide is shown in Table 20.

TABLE 20

| Exp | Solvent | Sonic | XCN | R—Cl | TEBAC | Temp. | 2 h | 5 h |
|---|---|---|---|---|---|---|---|---|
| JK-94A | NMP | No | NaCN (2) | 0.5 | 0.5 | 120° C. | 6% | 6% |
| JK-94B | DMSO | No | NaCN (2) | 0.5 | 0.5 | 120° C. | 85% | 85% |
| JK-94C | NMP | Yes | NaCN (2) | 0.5 | 0.5 | 50° C. | 83% + impurities | — |
| JK-94D | DMSO | Yes | NaCN (2) | 0.5 | 0.5 | 50° C. | 63% + impurities | — |

A list of SynFini reactions using anhydrous DMSO, ground sodium cyanide, sonicated and suspended is shown in Table 21. Sonicating the reactor loop did not induce mixing.

TABLE 21

| Exp | Solvent | XCN | R—Cl | TEBAC | Temp. | 10.3 min | 12.7 min |
|---|---|---|---|---|---|---|---|
| JK-95A | DMSO | NaCN (0.3) | 0.3 | 0.15 | 160° C./10 min | 17% | 83% |
| JK-94B | DMSO | NaCN (0.8) | 0.2 | 0.4 | 160° C./10 min | 39% | 61% |

Figure 17:
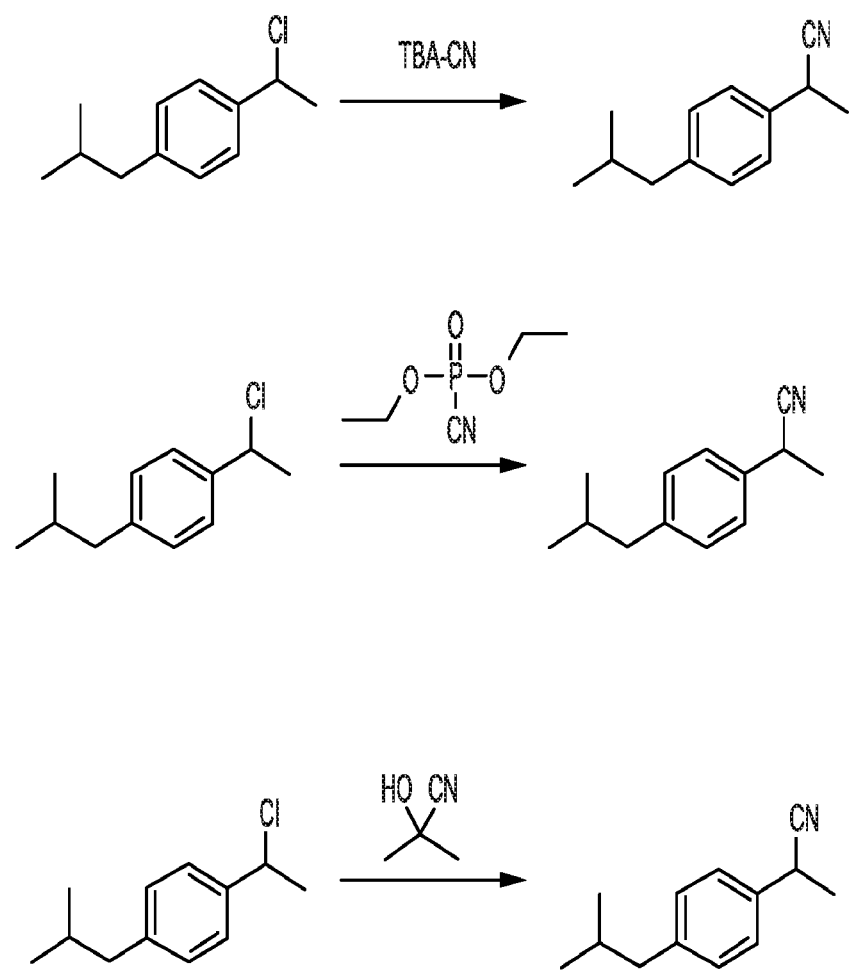
FIG. 17 shows representative alternative synthetic approaches to the cyanation step.

Alternative synthetic approaches to effect the cyanation reaction are shown in FIG. 17.

Figure 18A:
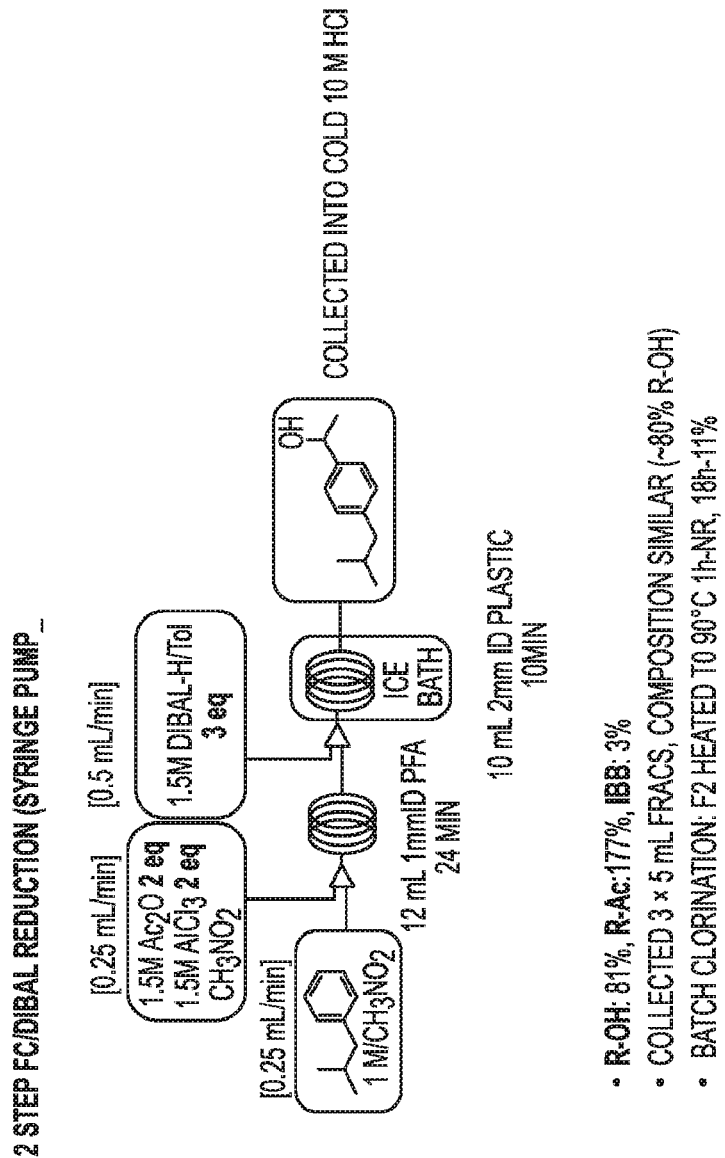
FIG. 18A and FIG. 18B show representative diagrams illustrating the two step FC/DIBAL reduction via a syringe pump.
Figure 18B:
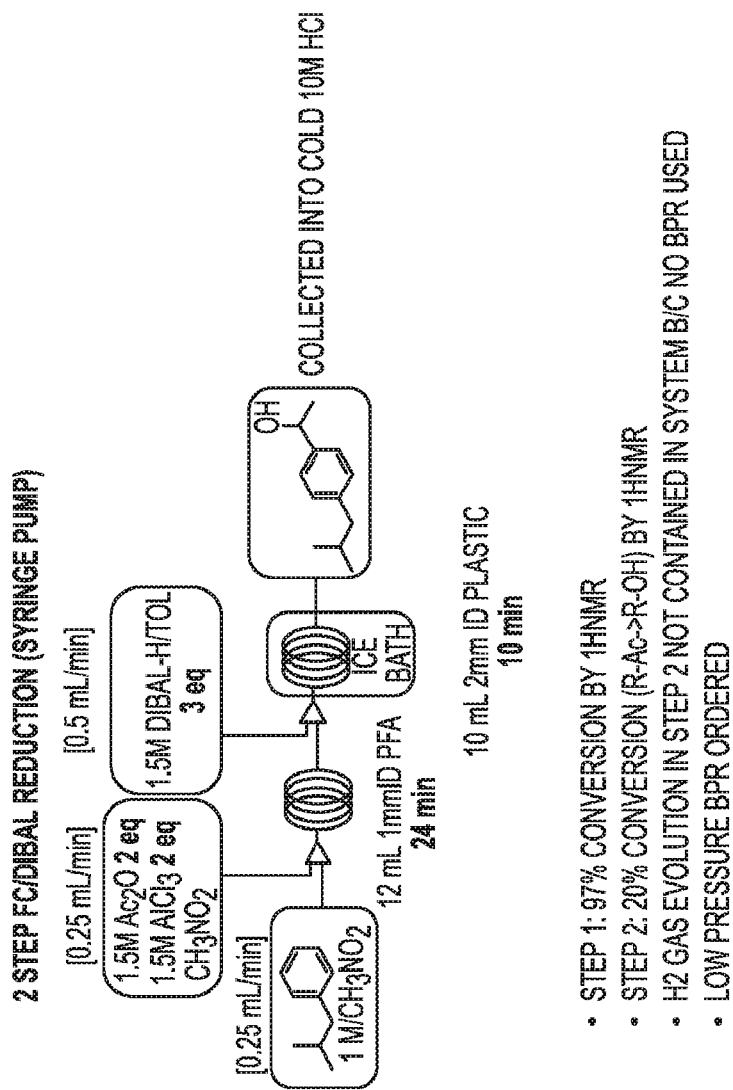
Figure 19:
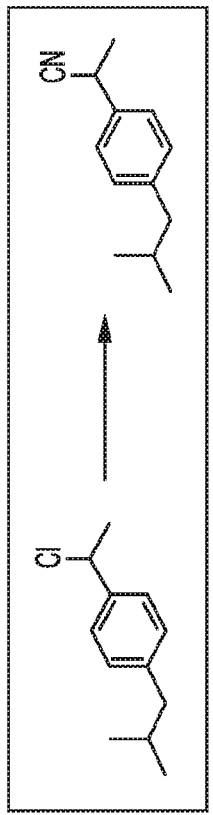
FIG. 19 shows representative reaction parameters of a single step $S_N2$ cyanation via Synfini.
Figure 20:
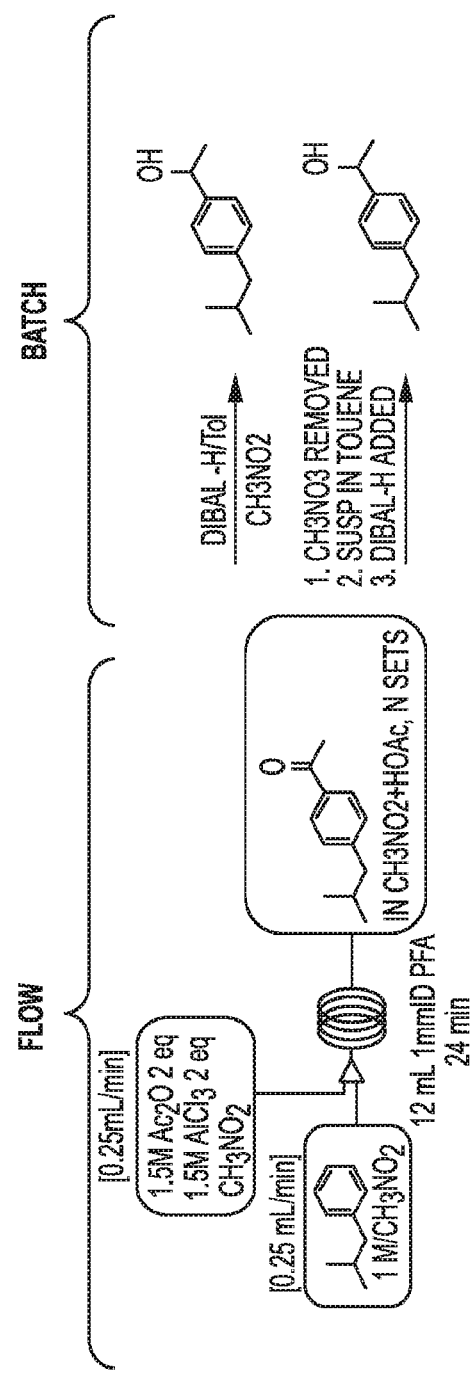
FIG. 20 shows a representative diagram illustrating the combined flow and batch approach to access 1-(4-isobutylphenyl)ethan-1-ol.
Figure 21A:
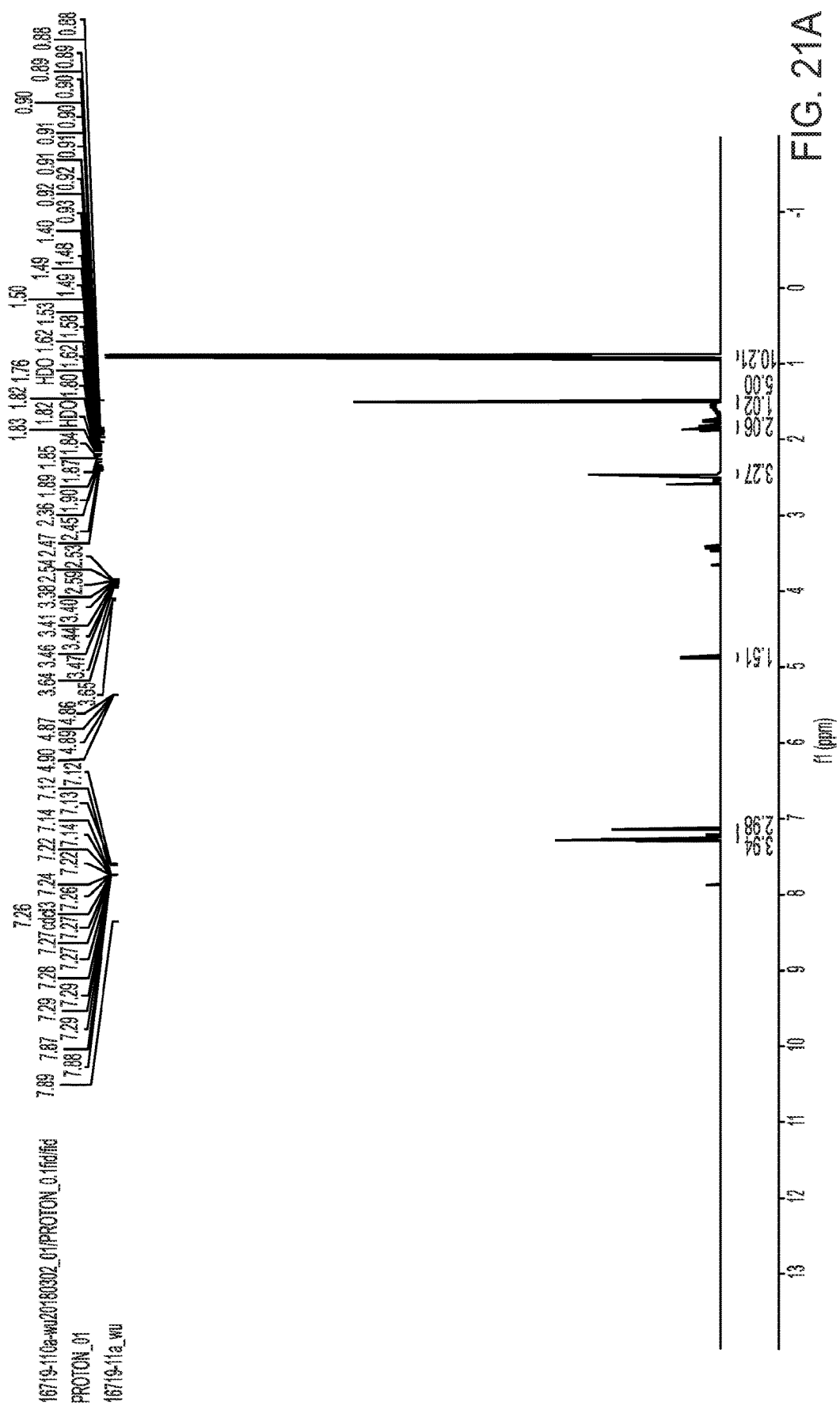
FIG. 21A and FIG. 21B show representative $^1$H NMR spectra of the batch alcohol prepared in FIG. 20 with (21A) and without (21B) nitromethane.
Figure 21B:
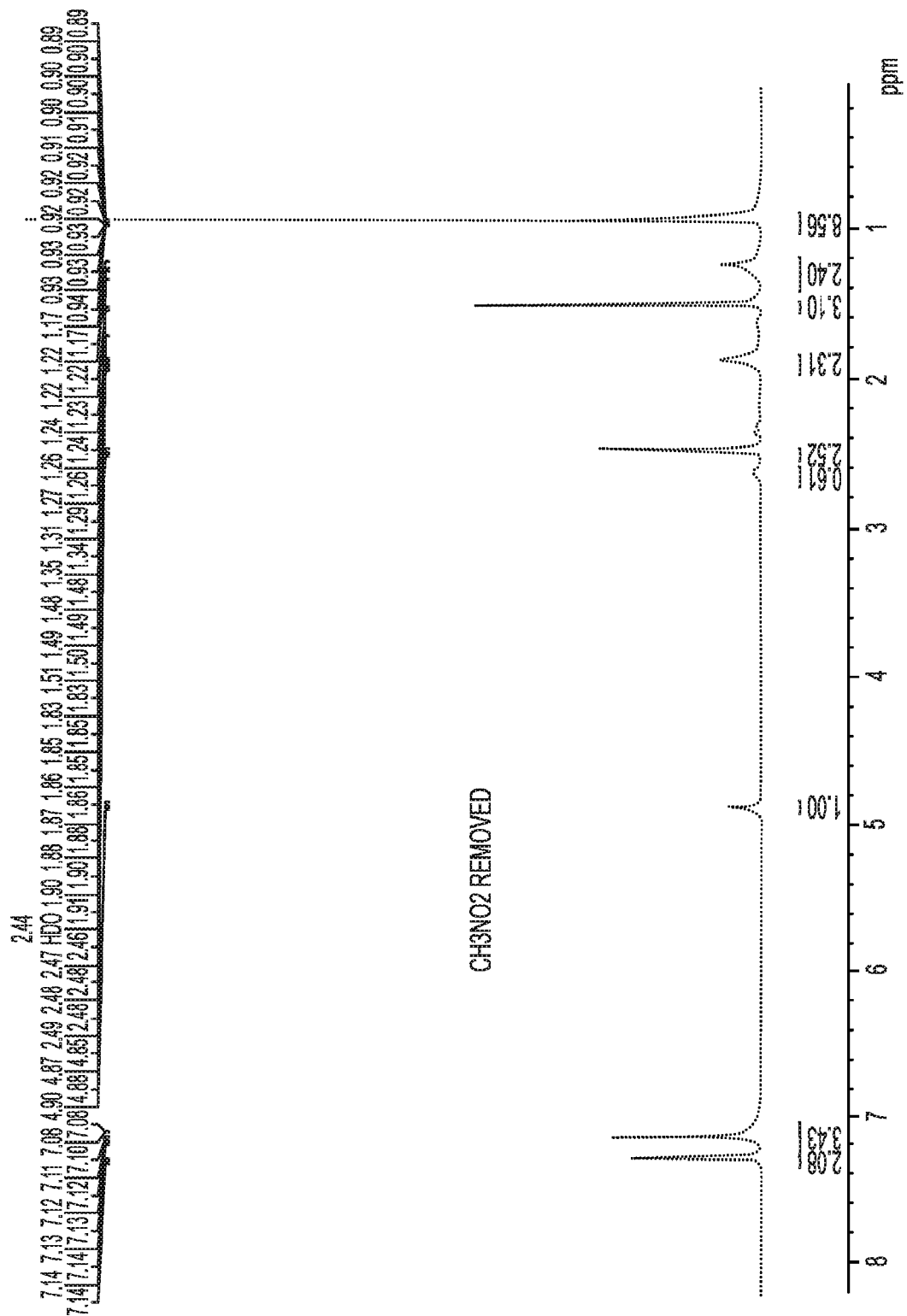

A diagram illustrating the two step FC/DIBAL reduction via a syringe pump is shown in FIG. 18A and FIG. 18B. The reaction parameters of a single step cyanation $S_N2$ via Synfini are shown in FIG. 19. A diagram illustrating the combined flow and batch approach to access 1-(4-isobutylphenyl)ethan-1-ol is shown in FIG. 20. A $^1$H NMR spectra of the batch alcohol with and without nitromethane is shown in FIG. 21A and FIG. 21B, respectively.

A cyanation vial solvent screen was performed, as shown in Table 22.

TABLE 22

TBACN (54 mg, 0.2 mmol), 1 mL (0.1M) solvent

| Solvent | R—Cl | Result |
|---|---|---|
| DMSO | 20 mg (0.1 mmol) | 90% by TLC, NMR suspect |
| CAN | 20 mg (0.1 mmol) | 90% by TLC, 89% by NMR |
| Tol-Water (10:1) | 20 mg (0.1 mmol) | 10% by TLC |

Figure 22:
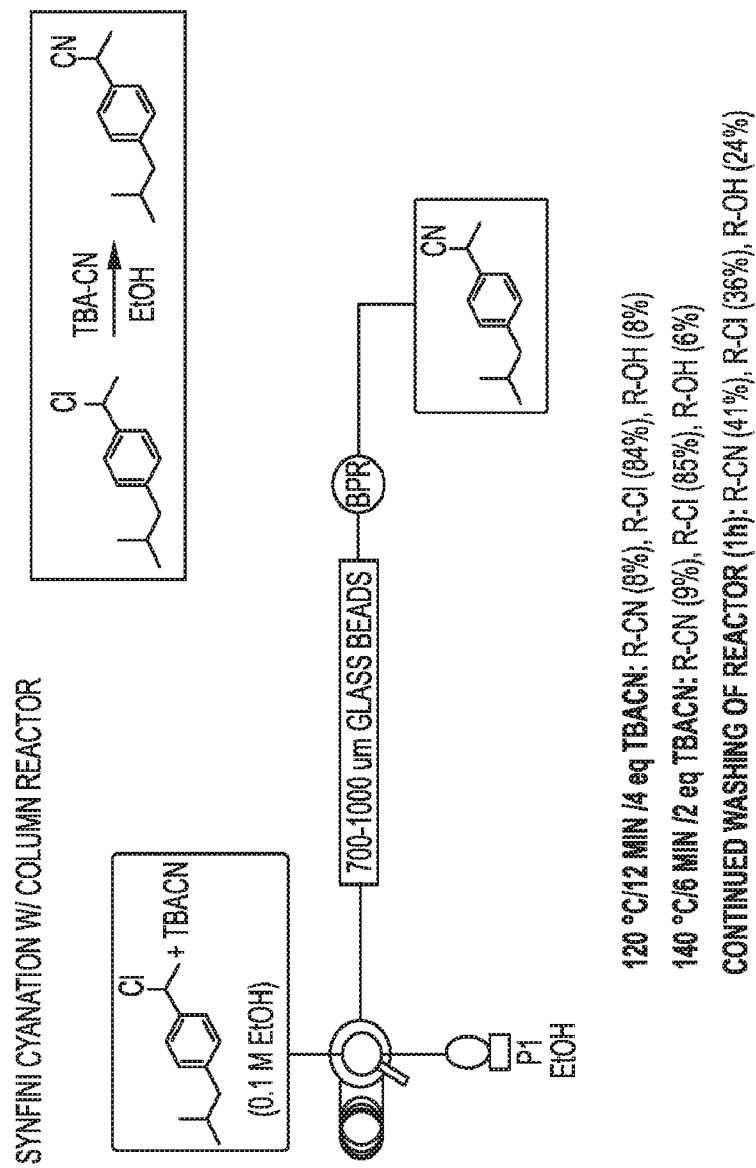
FIG. 22 shows a representative diagram illustrating the Synfini cyanation with a column reactor.
Figure 23:
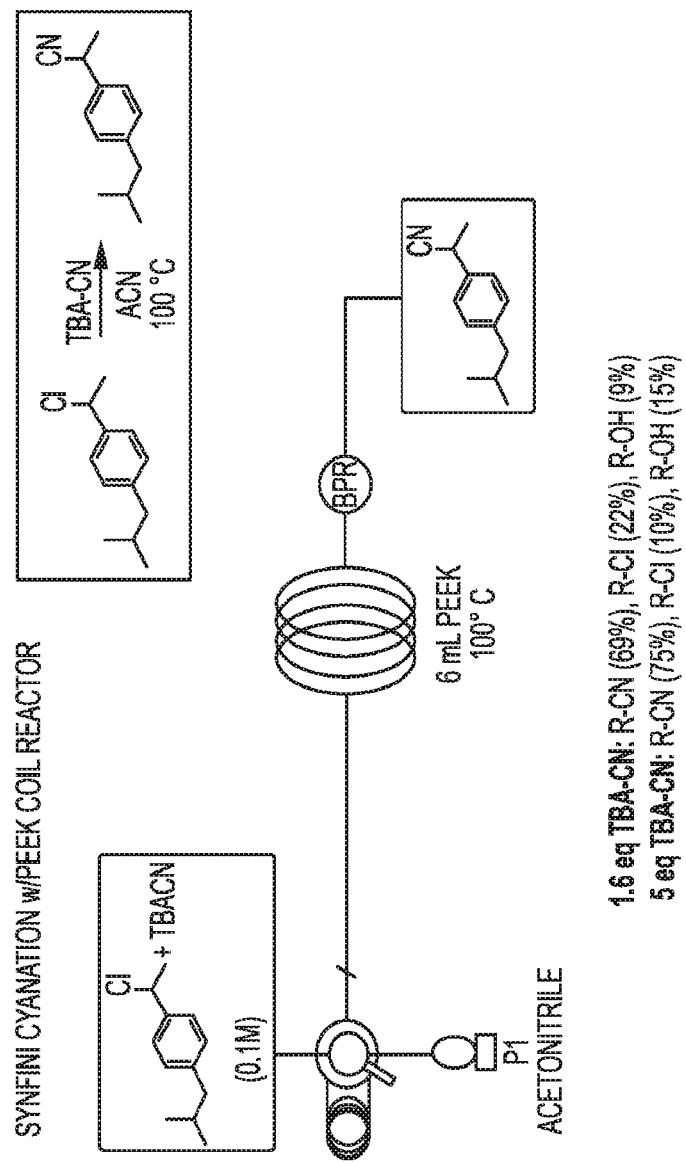
FIG. 23 shows a representative diagram illustrating the Synfini cyanation with a PEEK coil reactor.

A diagram illustrating the Synfini cyanation reaction with a column reactor is shown in FIG. 22. A diagram illustrating the Synfini cyanation reaction with a PEEK coil reactor is shown in FIG. 23.

Figure 24:
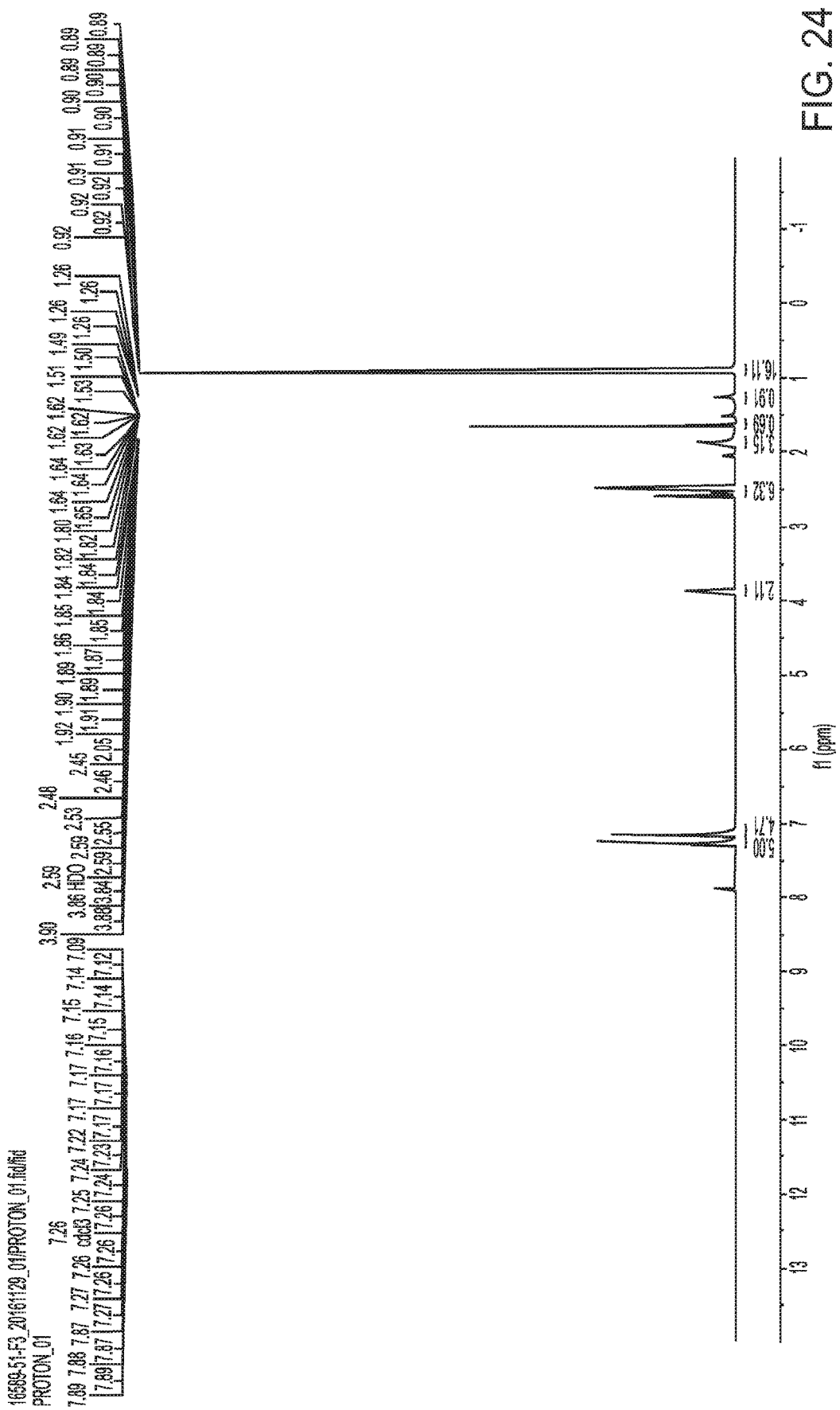
FIG. 24 shows a representative $^1$H NMR spectrum of the nitrile derivative.

A $^1$H NMR of 2-(4-isobutylphenyl)propanenitrile is shown in FIG. 24.

A list of conditions to hydrolyze the nitrile to a carboxylic acid is shown in Table 23.

TABLE 23

Figure 25A:
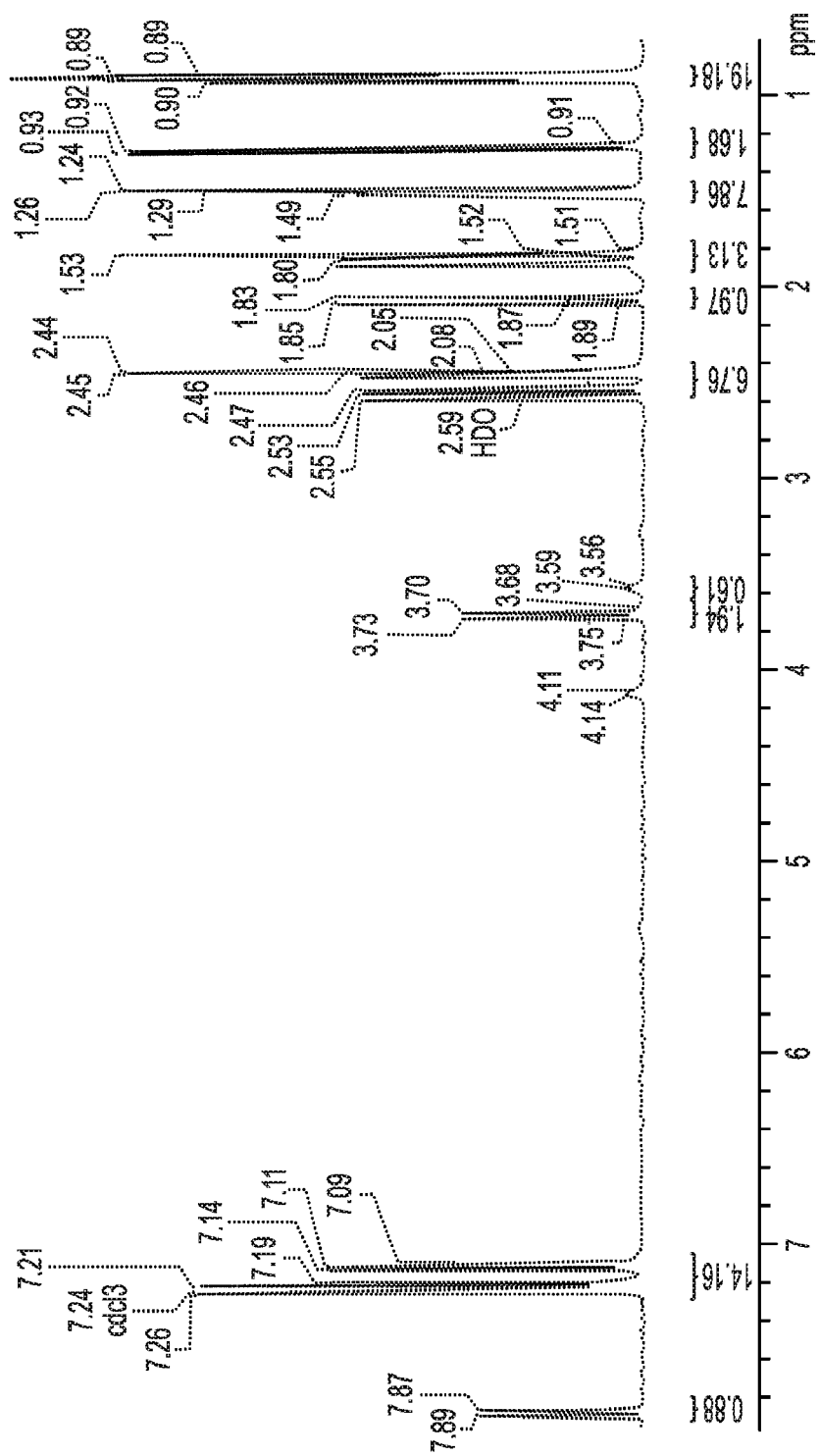
FIG. 25A-C show representative $^1$H NMR spectra of ibuprofen, prepared via the cyanation conditions listed in Table 23.
Figure 25B:
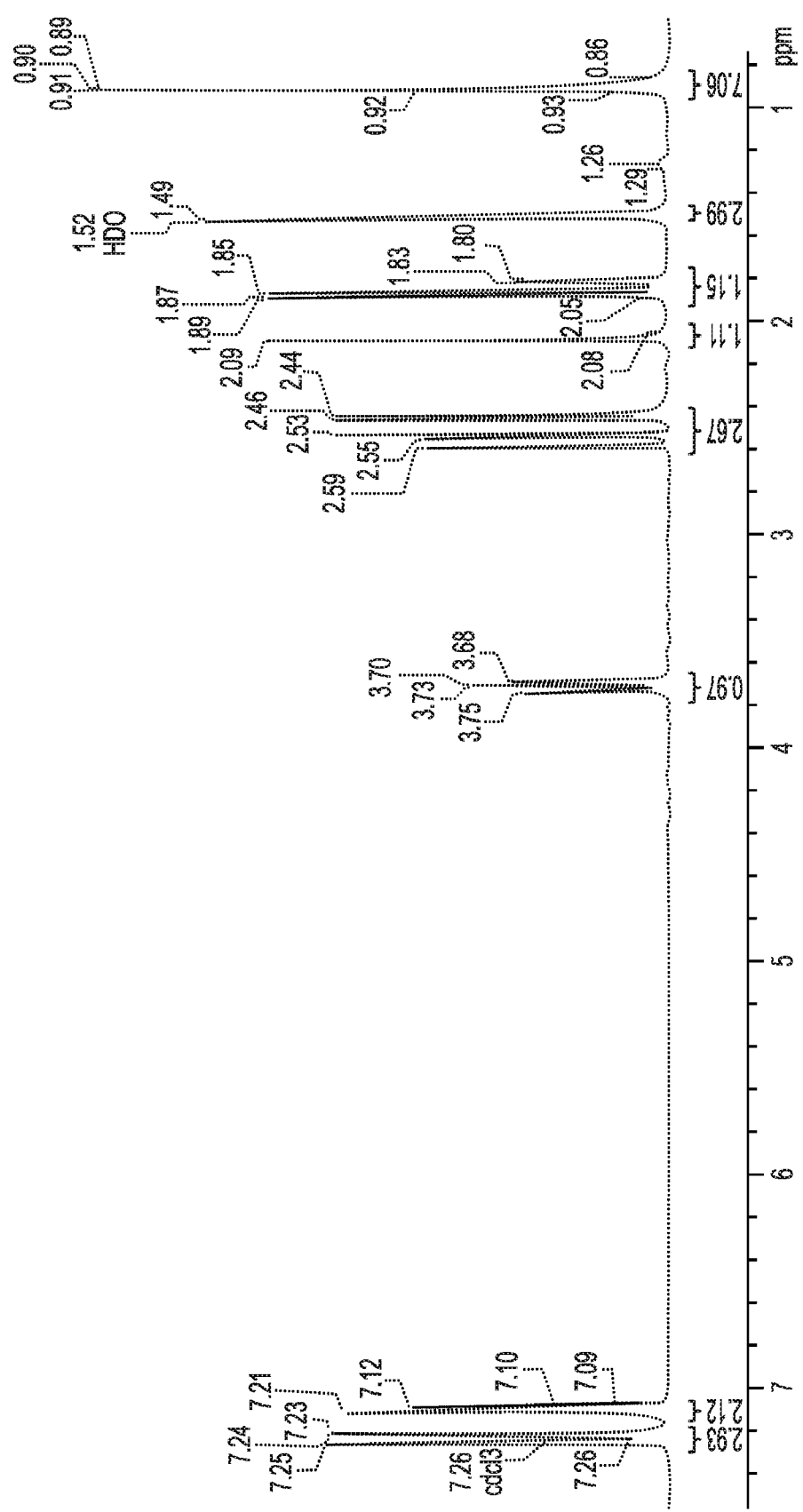
Figure 25C:
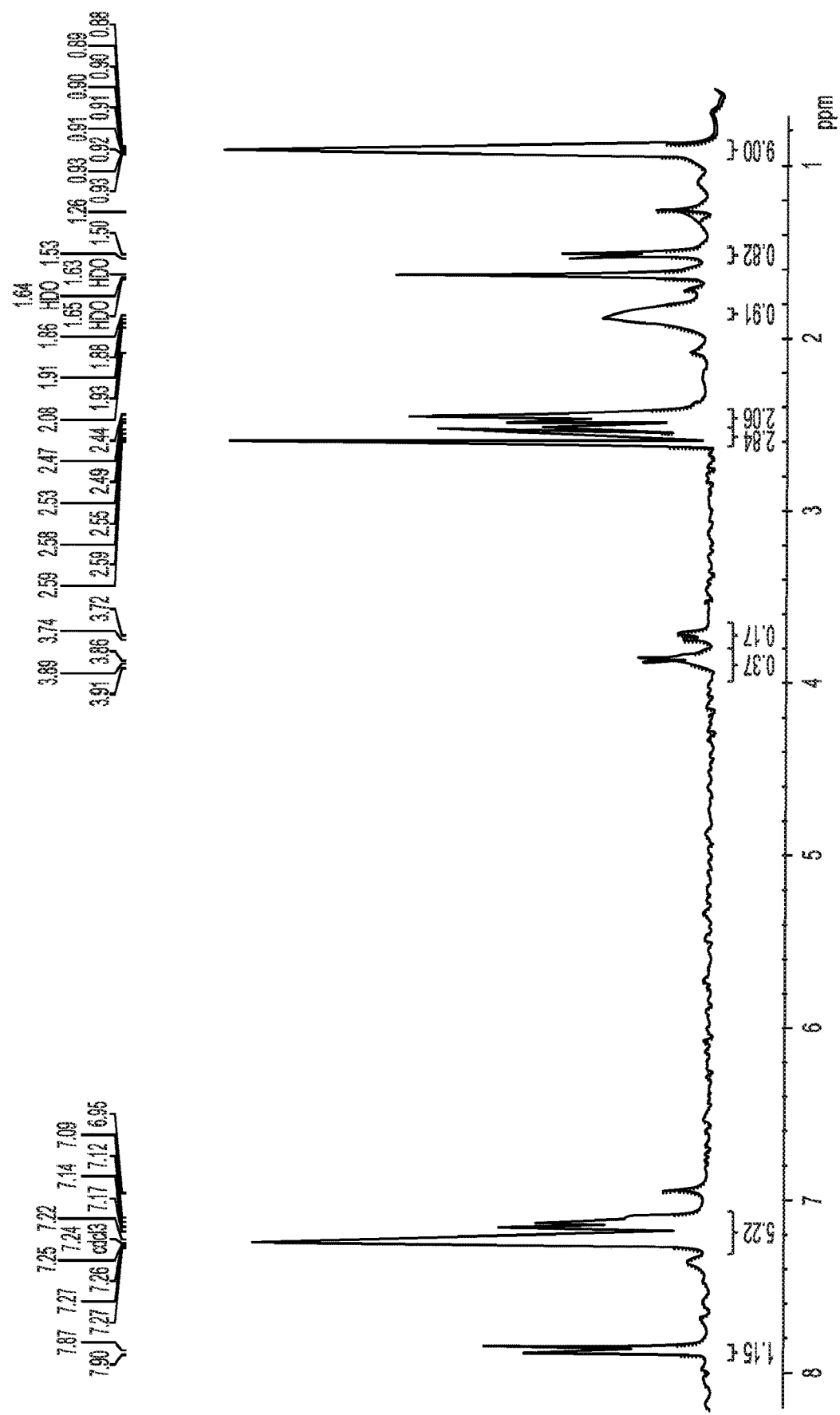

| Conditions | Results | Notes | $^1$H NMR spectra |
|---|---|---|---|
| 50% KOH, ethanol, 80° C. | 70% crude | Miscible, oiled out after 4 hrs | FIG. 25A |
| AcOH:H$_2$SO$_4$:H$_2$O (3:3:1), 110° C. | 66% crude | Not miscible in the beginning, miscible at 110° C., oiled out after 5 hrs | FIG. 25B |
| KOH, ethylene glycol:H$_2$O, 110° C. | 66% crude | Not miscible in the beginning, not miscible at 110° C. | FIG. 25C |

4. Step 5: Hydrolysis

Figure 26:
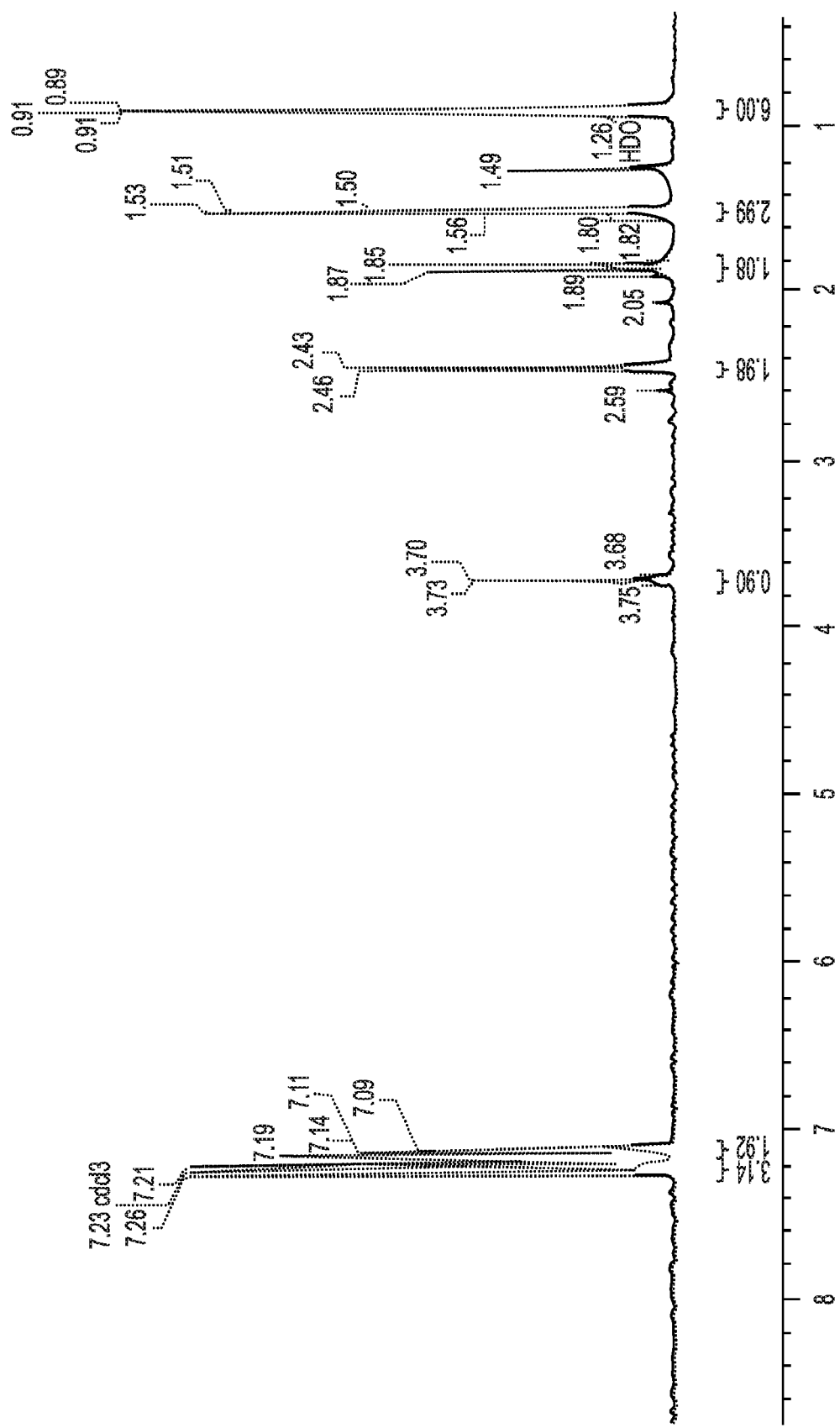
FIG. 26 shows a representative $^1$H NMR spectrum of the carboxylic acid derivative.
Figure 27A:
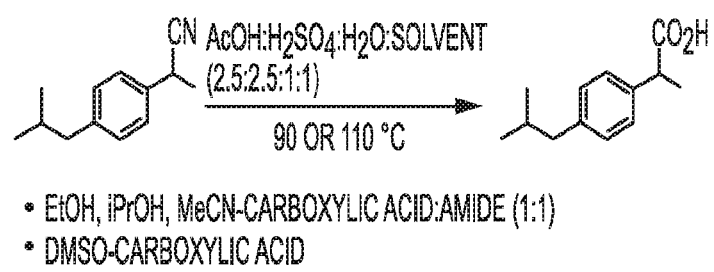
FIG. 27A and FIG. 27B show representative summaries of the solvent screen for the hydrolysis step.
Figure 27B:
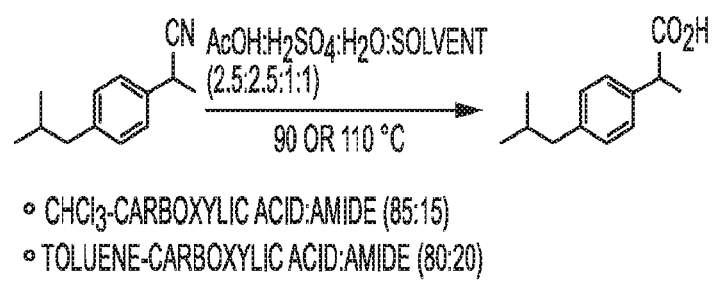
Figure 29:
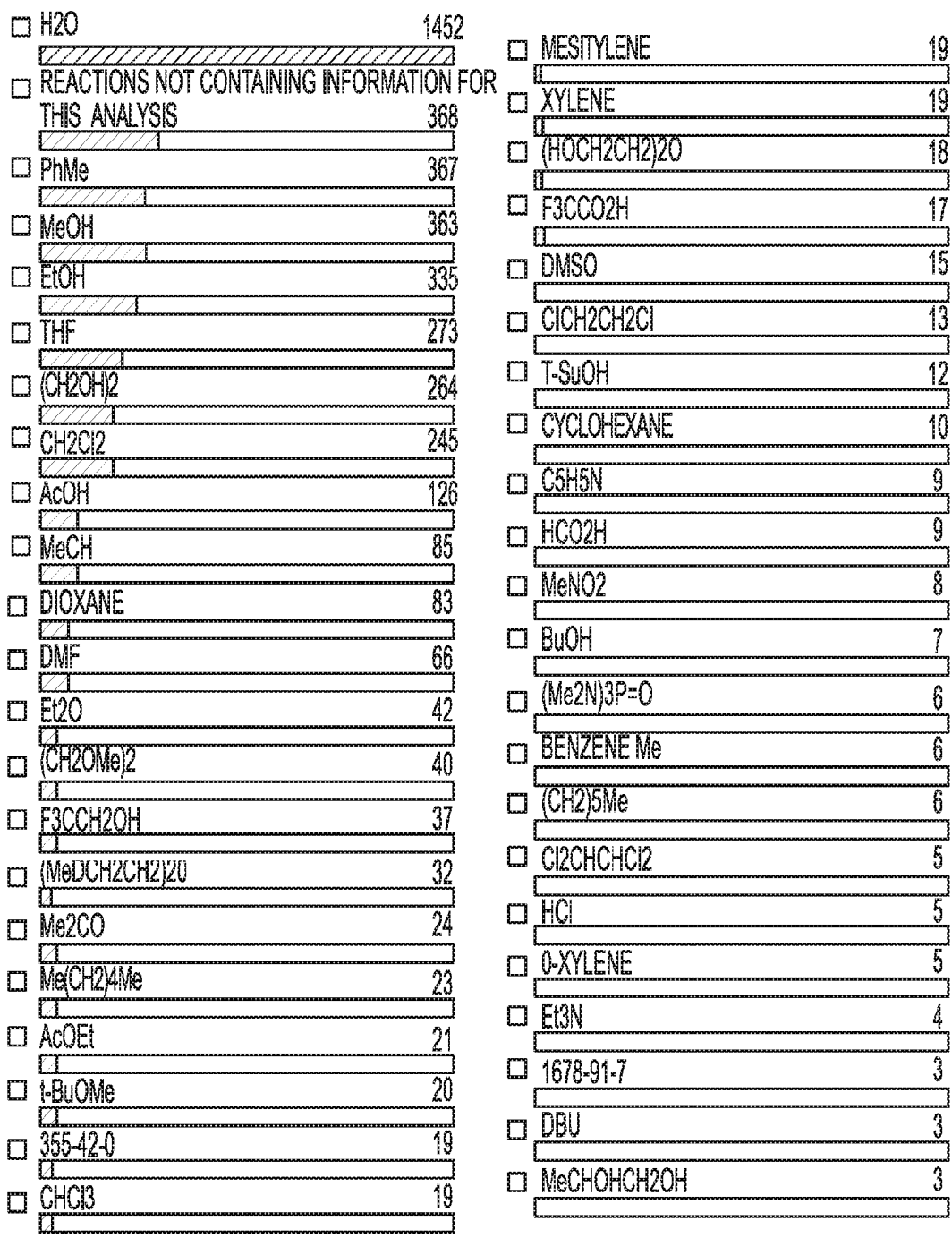
FIG. 29 shows a representative list of solvents previously used in hydrolysis reactions.

A $^1$H NMR spectra of the product carboxylic acid is shown in FIG. 26.

Figure 30A:
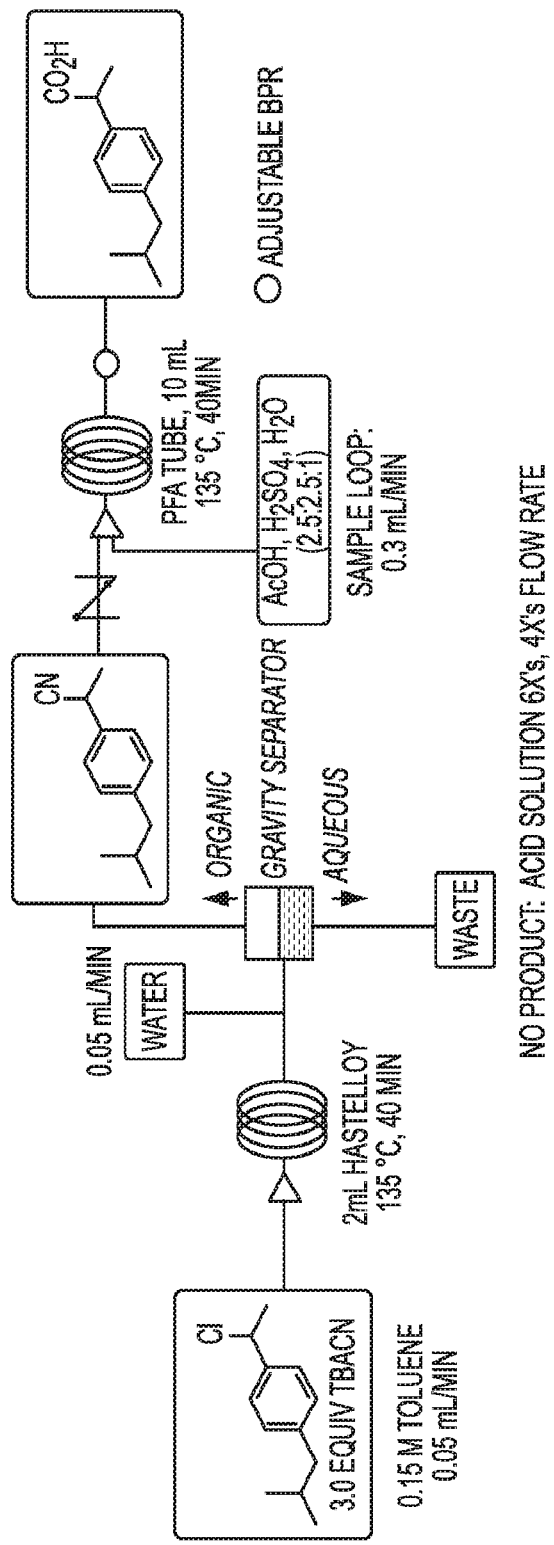
FIG. 30A and FIG. 30B show representative diagrams illustrating the synthesis of ibuprofen via Autosyn.
Figure 30B:
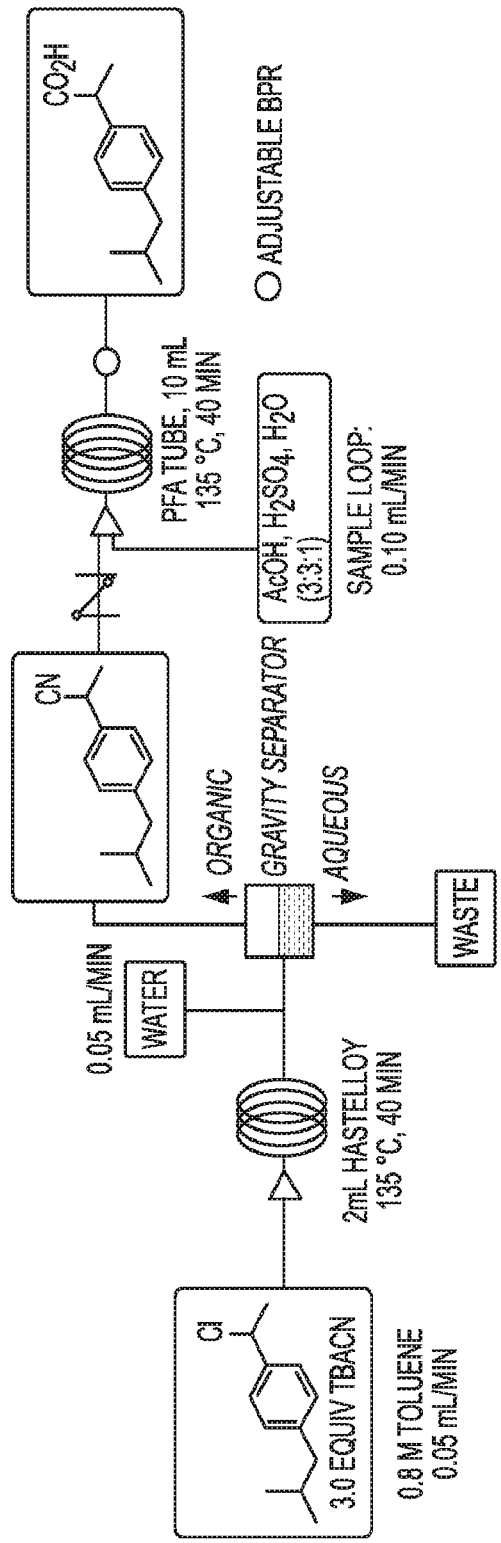

As shown in FIG. 30, and Table 24, a variety of conditions were explored to reduce the amount of TBACN.

TABLE 24

| Entry | TBACN equiv. | Temp. | Solvent | Results/comments |
|---|---|---|---|---|
| 1 | 5.0 | 120° C. | Toluene | Product |
| 2 | 1.5 | 120° C. | Toluene | SM:Prod.—78:22 |
| 3 | 3.0 | 120° C. | Toluene | SM:Prod.—20:80 + impurity |
| 4 | 3.0 | 135° C. | Toluene | Prod. + impurity |
| 5 | 2.0 | 135° C. | Toluene | SM:Prod—18:82 + impurity |
| 6 | 2.5 | 145° C. | Toluene | Prod. + impurity |
| 7 | 5.0 | 120° C. | Toluene | Prod. + impurity |
| 8 | 5.0 | 120° C. | MeCN | product |

SM: starting material

Figure 30C:
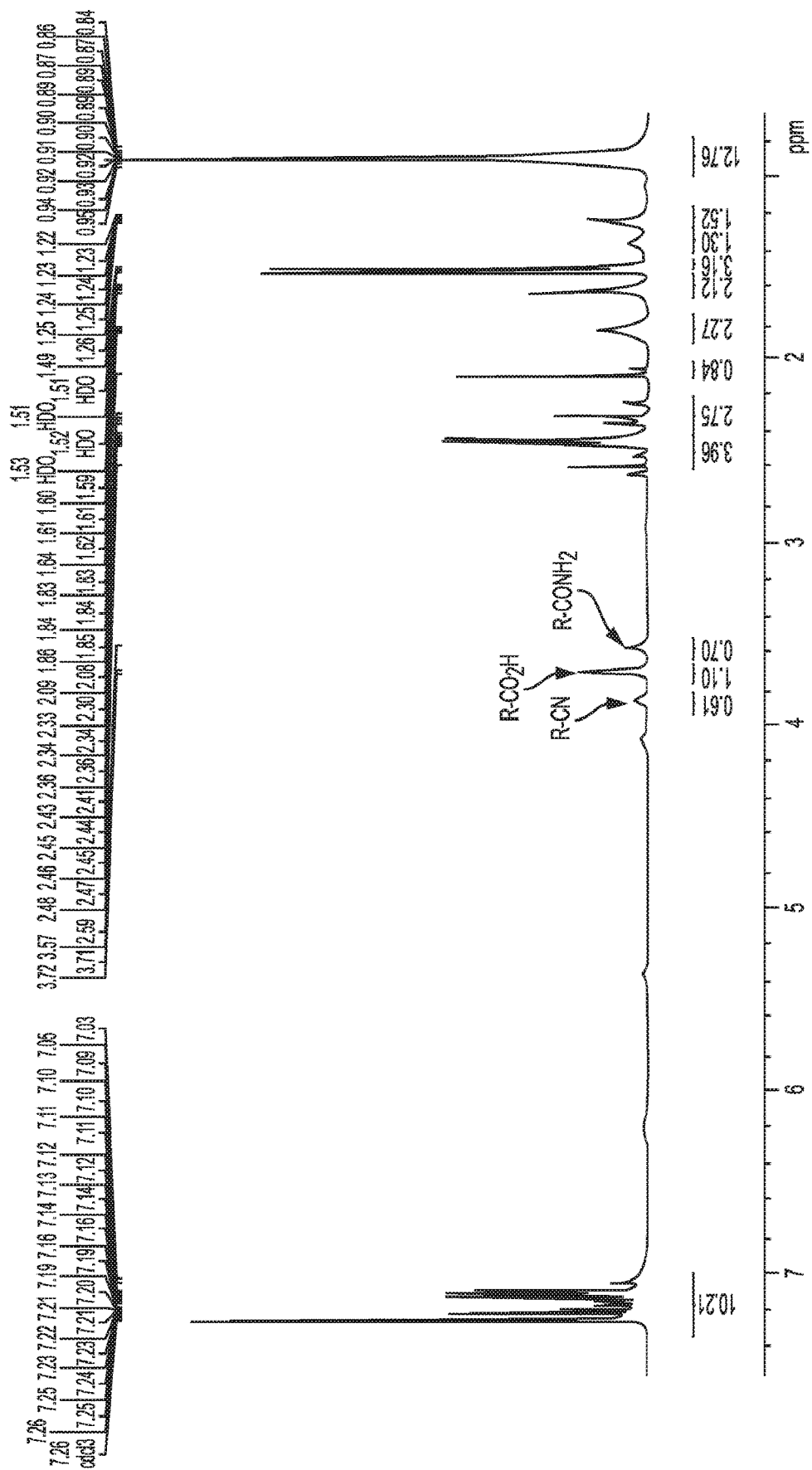
FIG. 30C shows a representative $^1$H NMR spectra of ibuprofen prepared as in FIG. 30B.

A $^1$H NMR spectra of the acid derivative is shown in FIG. 30C.

Figure 31A:
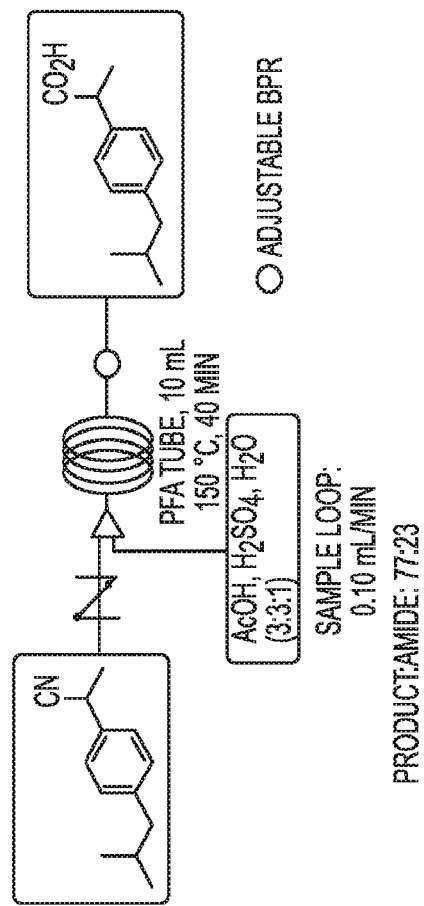
FIG. 31A shows a representative diagram illustrating the conversion of the cyanide to the acid via an Autosyn system at a temperature of 150° C. and a sample loop of 0.10 mL/min.
Figure 31B:
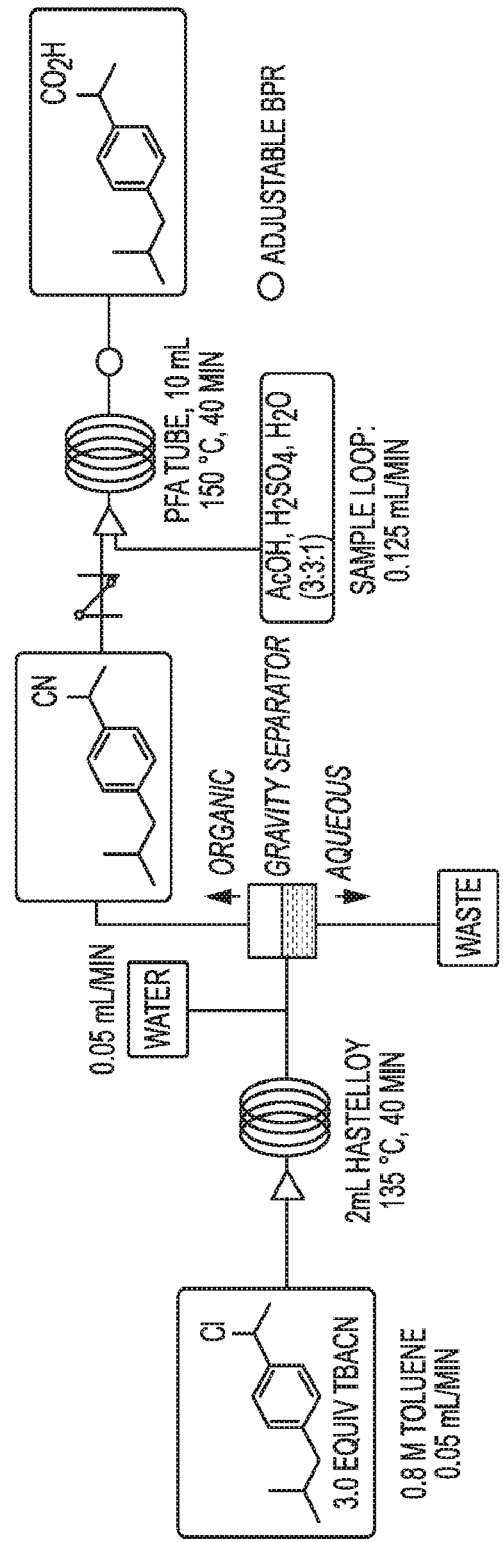
FIG. 31B shows a representative diagram illustrating the synthesis of ibuprofen via an Autosyn system at a temperature of 150° C. and a sample loop of 0.125 mL/min.
Figure 31C:
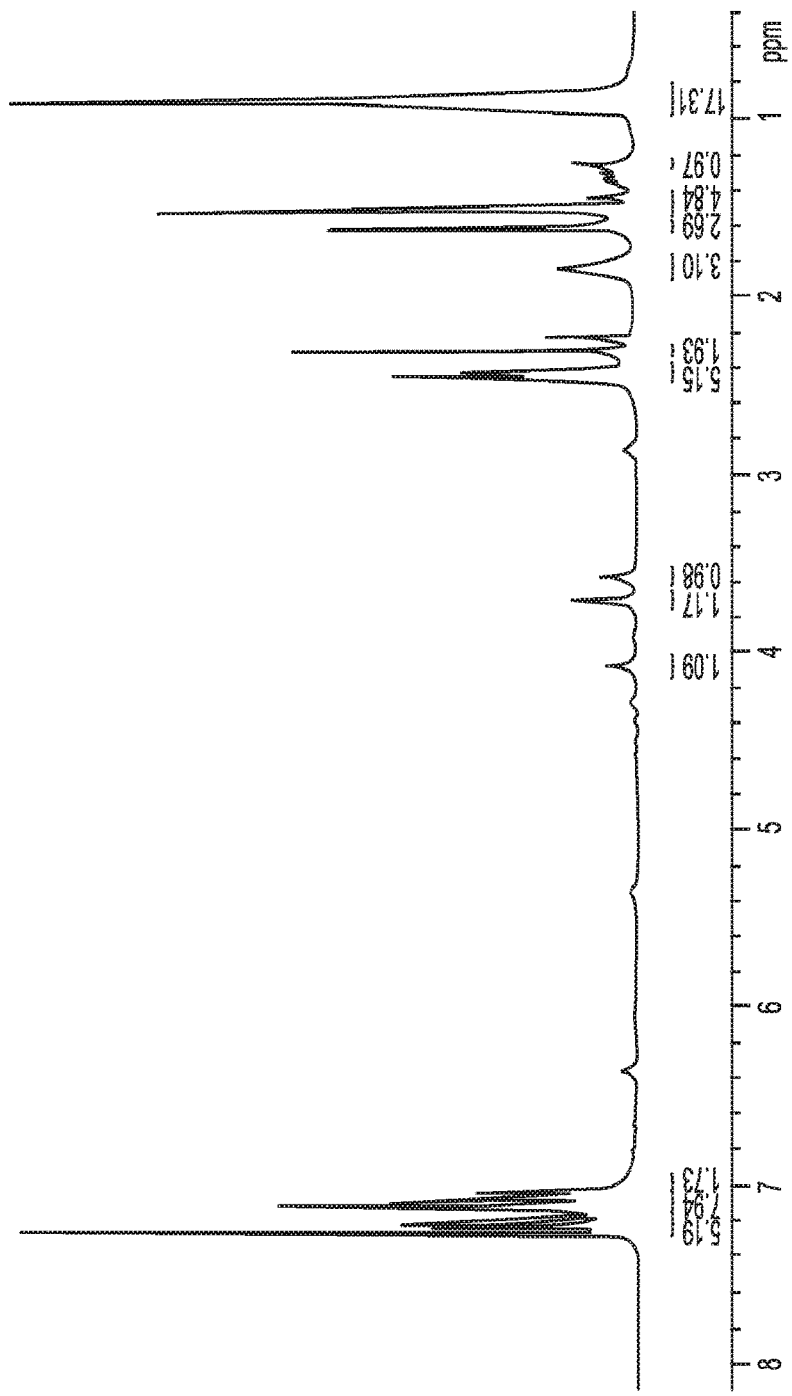
FIG. 31C shows a representative $^1$H NMR spectrum of ibuprofen prepared as shown in FIG. 31B.

A diagram illustrating the conversion of the cyanide to the acid via an Autosyn system at a temperature of 150° C. and a sample loop of 0.10 mL/min. is shown in FIG. 31A. A diagram illustrating the synthesis of ibuprofen via an Autosyn system at a temperature of 150° C. and a sample loop of 0.125 mL/min. is shown in FIG. 31B. A $^1$H NMR spectra of the product acid from FIG. 31B is shown in FIG. 31C.

Figure 32:
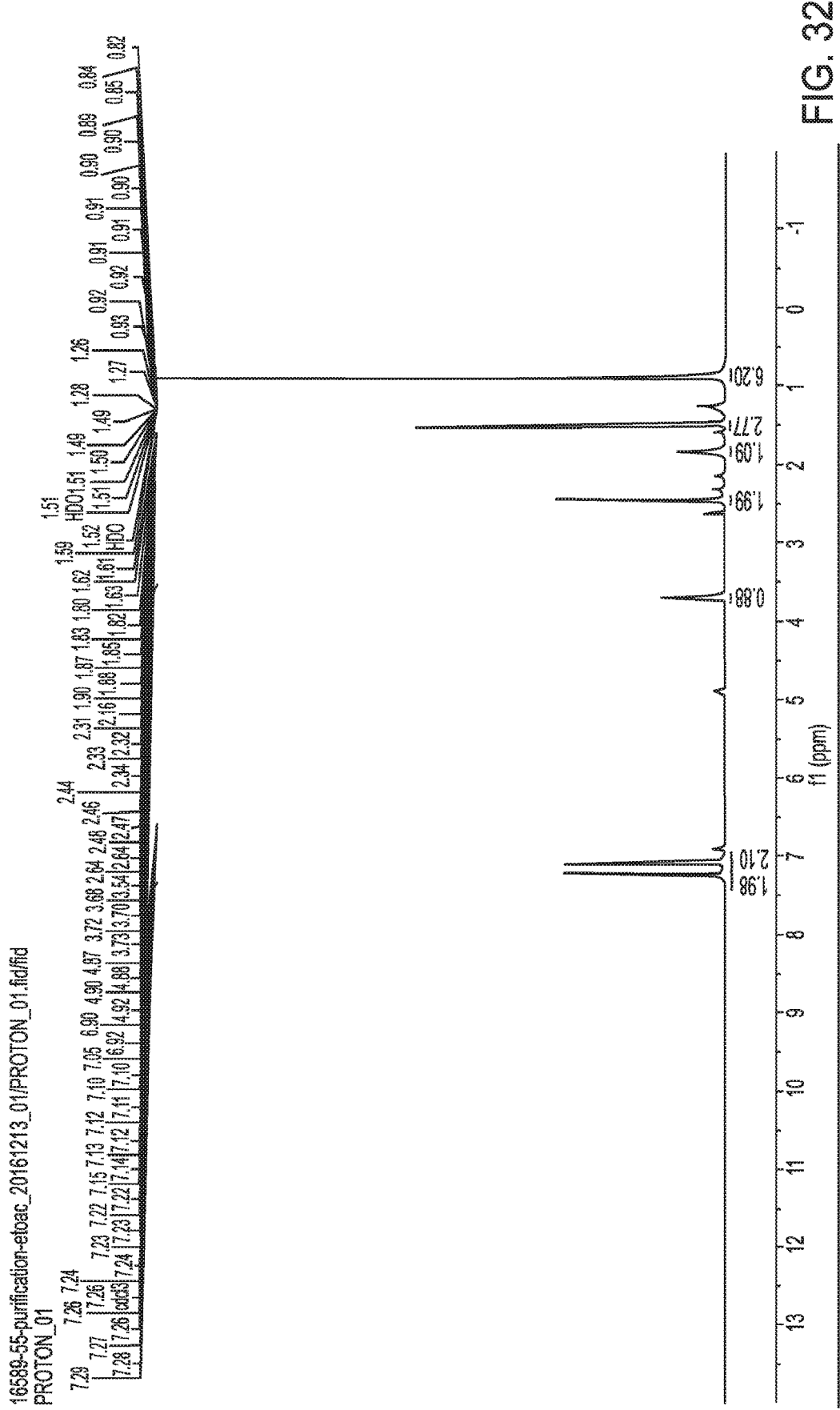
FIG. 32 shows a representative $^1$H NMR spectrum of purified ibuprofen prepared as disclosed herein.

A $^1$H NMR spectra of purified ibuprofen, prepared as described in the examples herein, is shown in FIG. 32.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for preparing a cyano compound having a structure represented by a formula:

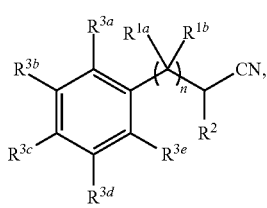

wherein n is selected from 0, 1, 2, 3, and 4;

wherein each of $R^{1a}$ and $R^{1b}$, when present, is independently selected from hydrogen and C1-C4 alkyl;

wherein $R^2$ is selected from hydrogen and C1-C4 alkyl; and wherein each of $R^{3a}$, $R^{3b}$, $R^{3c}$, $R^{3d}$, and $R^{3e}$ is independently selected from hydrogen, halogen, —OH, —NH$_2$, —NO$_2$, —CN, C1-C4 alkyl, and C1-C4 alkoxy;

or wherein any two of $R^{3a}$, $R^{3b}$, $R^{3c}$, $R^{3d}$, and $R^{3e}$ together comprise a structure represented by a formula:

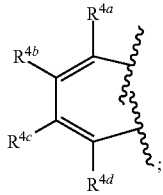

and wherein each of $R^{4a}$, $R^{4b}$, $R^{4c}$, and $R^{4d}$, when present, is independently selected from hydrogen, halogen, —OH, —NH$_2$, —NO$_2$, —CN, C1-C4 alkyl, and C1-C4 alkoxy, the method comprising the steps of:

(a) reducing a carbonyl compound having a structure represented by a formula:

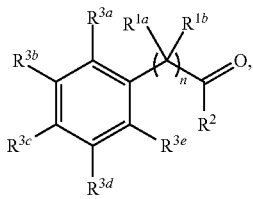

thereby producing an alcohol having a structure represented by a formula:

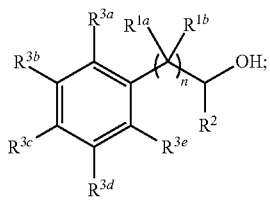

(b) converting a hydroxyl group on the alcohol to a leaving group, thereby producing a compound having a structure represented by a formula:

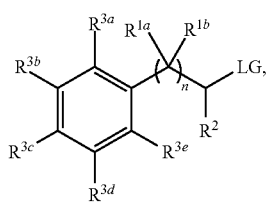

wherein LG is a leaving group; and (c) displacing the leaving group with a nucleophilic cyanide reagent, thereby producing the cyano compound, wherein step (b) is performed in flow.

2. The method of claim 1, wherein the cyano compound has a structure represented by a formula:

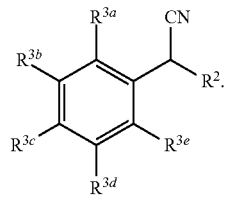

3. The method of claim 1, wherein the cyano compound has a structure represented by a formula:

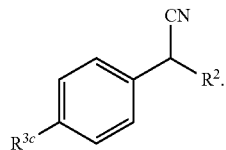

4. The method of claim 1, wherein the cyano compound has a structure represented by a formula:

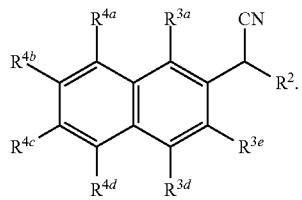

5. The method of claim 1, wherein the cyano compound has a structure represented by a formula:

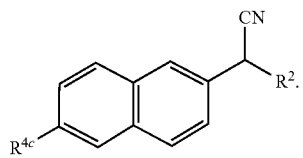

6. The method of claim 1, wherein the reducing step is an asymmetric reduction.

7. The method of claim 1, wherein displacing is via a stereospecific displacement reaction.

8. The method of claim 1, further comprising hydrolyzing the cyano compound, thereby producing a carboxylic acid having a structure represented by a formula:

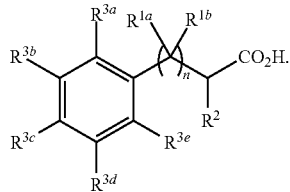

9. A method for preparing a cyano compound having a structure:

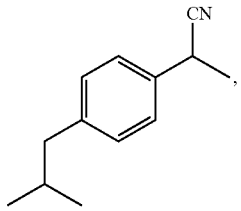

the method comprising the steps of:
(a) reducing a carbonyl compound having a structure:

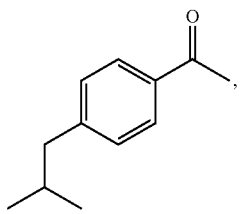

thereby producing an alcohol having a structure:

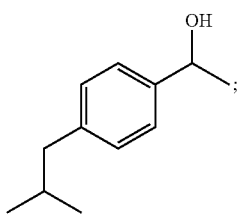

(b) converting a hydroxyl group on the alcohol to a leaving group, thereby producing a compound having a structure:

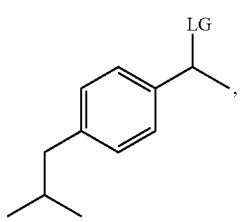

wherein LG is selected from chloro and mesyl; and
(c) displacing the leaving group with a nucleophilic cyanide reagent, thereby producing the cyano compound,
wherein steps (a), (b), and (c) are performed sequentially in flow.

10. The method of claim 9, further comprising hydrolyzing the cyano compound, thereby producing a carboxylic acid having a structure represented by a formula:

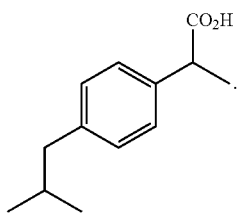

11. The method of claim 1, wherein step (a) is performed in flow.

12. The method of claim 11, wherein step (c) is performed in flow.

13. The method of claim 1, wherein step (c) is performed in flow.

14. The method of claim 1, wherein the method is performed via an automated chemical synthesis platform.

15. A method for preparing a cyano compound having a structure represented by a formula:

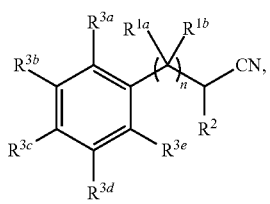

wherein n is selected from 0, 1, 2, 3, and 4;
wherein each of $R^{1a}$ and $R^{1b}$, when present, is independently selected from hydrogen and C1-C4 alkyl;
wherein $R^2$ is selected from hydrogen and C1-C4 alkyl; and
wherein each of $R^{3a}$, $R^{3b}$, $R^{3c}$, $R^{3d}$, and $R^{3e}$ is independently selected from hydrogen, halogen, —OH, —NH$_2$, —NO$_2$, —CN, C1-C4 alkyl, and C1-C4 alkoxy;
or wherein any two of $R^{3a}$, $R^{3b}$, $R^{3c}$, $R^{3d}$, and $R^{3e}$ together comprise a structure represented by a formula:

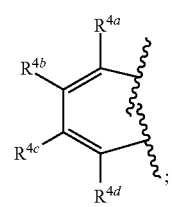

and
wherein each of $R^{4a}$, $R^{4b}$, $R^{4c}$, and $R^{4d}$, when present, is independently selected from hydrogen, halogen, —OH, —NH$_2$, —NO$_2$, —CN, C1-C4 alkyl, and C1-C4 alkoxy,
the method comprising the steps of:
(a) reducing a carbonyl compound having a structure represented by a formula:

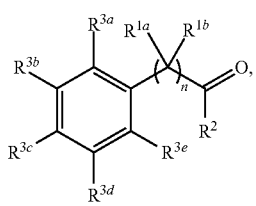

thereby producing an alcohol having a structure represented by a formula:

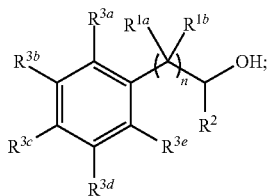

(b) converting a hydroxyl group on the alcohol to a leaving group, thereby producing a compound having a structure represented by a formula:

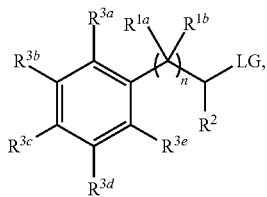

wherein LG is a leaving group; and (c) displacing the leaving group with a nucleophilic cyanide reagent, thereby producing the cyano compound, wherein step (b) is performed with no work-up.

16. The method of claim 15, wherein step (c) is performed with no work-up.

\* \* \* \* \*